(12) United States Patent
Long et al.

(10) Patent No.: US 6,541,202 B1
(45) Date of Patent: Apr. 1, 2003

(54) **TELOMERASE REVERSE TRANSCRIPTASE (TERT) GENES FROM *CANDIDA ALBICANS***

(75) Inventors: David M. Long, Livingston, MT (US); Anneke M. Metz, Bozeman, MT (US); Ruschelle A. Love, Bozeman, MT (US)

(73) Assignee: Research & Development Institute, Inc., Bozeman, MT (US)

( * ) Notice: Subject to any disclaimer, the term of this patent is extended or adjusted under 35 U.S.C. 154(b) by 0 days.

(21) Appl. No.: 09/417,485

(22) Filed: Oct. 13, 1999

(51) Int. Cl.[7] .................................................. C12Q 1/68
(52) U.S. Cl. .................... 435/6; 435/194; 435/320.1; 435/252.3; 435/419; 435/325; 435/254.11; 536/23.1; 536/23.2; 536/23.74
(58) Field of Search ............................. 536/23.1, 23.2, 536/23.74; 435/194, 6, 320.1, 252.3, 419 325, 254.11

(56) References Cited

U.S. PATENT DOCUMENTS

| | | |
|---|---|---|
| 5,489,508 A | 2/1996 | West et al. |
| 5,583,016 A | 12/1996 | Villeponteau et al. |
| 5,643,890 A | 7/1997 | Iversen et al. |
| 5,645,986 A | 7/1997 | West et al. |
| 5,686,306 A | 11/1997 | West et al. |
| 5,698,686 A | 12/1997 | Gottschling et al. |
| 5,707,795 A | 1/1998 | West et al. |
| 5,830,644 A | 11/1998 | West et al. |

FOREIGN PATENT DOCUMENTS

WO    WO97/14026    4/1997

OTHER PUBLICATIONS

Muzny et al. GenBank Accession No. AC005912, created Nov. 3, 1998.*
Johnston et al. The nucleotide sequence of *Saccharomyces cerevisiae* chromosome XII. Nature 1997; 387:87–90.*
Metz et al. Two telomerase reverse transcriptases (TERTs) expressed in *Candida albicans*. Biotechnol. Appl. Biochem. 2001 Aug.; 34(pt 1):47–54.*
Bryan et al., "Telomerase reverse transcriptase genes identified in *Tetrahymena thermophila* and *Oxytricha trifallax*," Proc. Natl. Acad. Sci. USA, 95(15): 8479–84, 1998.
Cong et al., "The human telomerase catalytic subunit hTERT: organization of the gene and characterization of the promoter," Hum. Mol. Genet., 8(1):137–142, 1999.
Greenberg et al., "Telomerase reverse transcriptase gene is direct target of c–Myc but is not functionally equivalent in cellular transformation," Oncogene, 18(5):1219–1226, 1999.

(List continued on next page.)

Primary Examiner—Ponnathapu Achutamurthy
Assistant Examiner—Kathleen Kerr
(74) Attorney, Agent, or Firm—Morgan, Lewis & Bockius

(57) ABSTRACT

The present invention pertains, in general, to the identification, isolation and use of Telomerase Reverse Transcriptase (TERT) genes and the proteins encoded by such genes. In particular, the present invention pertains to the identification, isolation and use of TERT genes and TERT proteins from several genetically diverse and economically important organisms, including two human pathogens, *Candida albicans* and *Plasmodium falciparum* and an agronomic crop species, *Oryza sativa*.

15 Claims, 7 Drawing Sheets

PLASMODIUM FALCIPARUM
PUTATIVE TELOMERASE GENE

① SANGER CENTRE CHROMOSOME 13 CONTIG 41294
② SANGER CENTRE CHROMOSOME 13 CONTIG 02431
③ TIGR DATABASE CHROMOSOME 14 CONTIG 5560 NOW 364

OTHER PUBLICATIONS

Greider et al., "A telomeric sequence in the RNA of Tetrahymena telomerase required for telomere repeat synthesis," Nature, 337(6205):331–337, 1989.

Lingner, et al., "Reverse transcriptase mofits in the catalytic subunit of telomerase," Science, 276(5312):561–567, 1997.

Lingner et al., "Telomerase RNAs of different ciliates have a common secondary structure and a permuted template," Genes & Development, 8(16):1984–1998, 1994.

McEachern et al., "Cap–prevented recombination between terminal telomeric repeat arrays (telomere CPR) maintains telomeres in *Kluyveromyces lactis* lacking telomeres," Genes & Development, 10:1822–1834, 1996.

Romero et al., "A conserved secondary structure for telomerase RNA," Cell, 67(2):343–353, 1991.

Shippen–Lentz et al., "Functional evidence for an RNA template in telomerase," Science, 247(4942): 546–552, 1990.

Singer et al., "TLC1: template RNA component of *Saccharomyces cerevisiae* telomerase," Science, 266(5184): 404–409, 1994.

Xu et al., "Suppression of telomerase reverse transcriptase (hTERT) expression in differentiated HL–60 cells: regulatory mechanisms," Br. J. Cancer, 80(8):1156–1161,1999.

Wang et al., "Telomere–telomere recombination provides an express pathway for telomere acquisition," Nature, 345:456–458, 1990.

Zakian, V. A., "Life and cancer without telomerase," Cell, 91:1–3, 1997.

Nakamura et al. (1997) *Science* vol. 277, p. 955–959.

Steinberg et al. (2001), *The Facts on File Dictionary of Biotechnology and Genetic Engineering*, New Edition, Checkmark Books, p. 108.

* cited by examiner

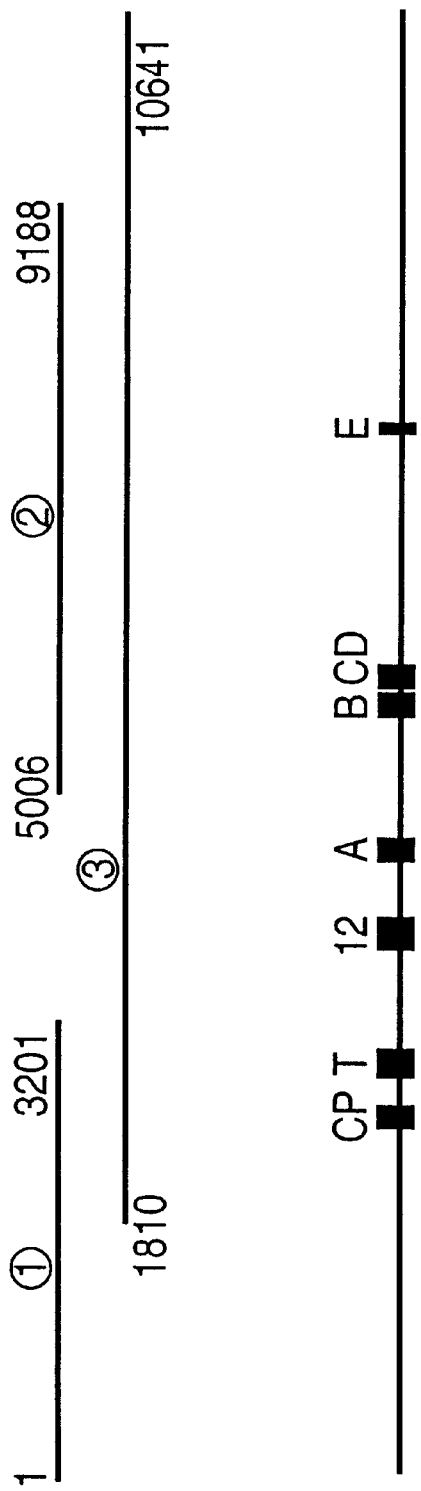

FIG. 2A

```
                                     Motif T2
h.          1  VLLKT-HCPLRA-QLLRQHSSPWQVYGFVRACLRRLVPPGLWG-RHNERRFLRNTKKFIS
m.          1  RLLRS-HCRFRT-DLLRLHSSPWQVYGFLRACLCKVVSASLWG-RHNERRFFKNLKKFIS
o.          1  YYLSK-NCPLPE-QLFEYQQDQRQISNFLTEFVANVFPKNFLE-GKNKKIFNKKMLQFVK
E.          1  YYLTK-SCPLPE-ELFSYTTDNKCVTQFINEFFYNILPKDFLT-GRNRKNFQKKVKKYVE
T.          1  YLLKK-FCKLPE-SLYDTEISYKQITNFLRQIIQNCVPNQLLG-KKNFKVFLEKLYEFVQ
Sp.         1  KVYNH-YCPYID-KILSYSLKPNQVFAFLRSILVRVFPKLIWG-QRIFEIILKDLETFLK
Plasmodium  1  DEYKQ-ICKQIK-DFLSFSFKTYKIINFMVYITKKCIPIKLLG-KHNFKIFLKNVKKFLL
Sc.         1  SDLNS-ICPPLE-SHLSRQSPKERVLKFIIVILQKLLPQEMFG-KKNKGKIIKNLNLULS
Ca.         1  KRIGT-KCNFAN-NVVSNKTEISQVIQFVLLVLGKLLPLDAWG-VSNKKIIKDRVVDFLL
consensus   1     llk  Cpl e  llsy s   qv nFlr il klvp lwg rhnkkiflknlkkfl
                                     Motif T
h.         58  LKGHAKLSLQELTWKMSVR-ILAKFLHWLMSVYVVELLRSFFYVTETTFQKN-LFFYRKS
m.         58  LGKYGKLSLQELMWKMKVE-ILATFLFWLMDTYVVQLLRSFFYITESTFQKN-LFFYRKS
o.         58  FNRFESFTKISLLNKFRVN-VFFKVLKWMFEDLAITLMRCYFYSTEKAKEYQ-LFYYRKN
E.         58  LNKHELIHKNLLLEKINTR-VLWKLLRWIFFDLVVSLTRCFFYMTEQQKSYS-TYYYRKN
T.         58  MKRFENQKVLDYICFMDVF-ILGDLIVFIINKLVIPVLRYNFYITEKHKEGS-IFYYRKP
Sp.        58  LSRYESFSLHYLMSNIKIS-IFAEFIYWLYNSFIIPILQSFFYITESSDLRN-TVYFRKD
Plasmodium 58  FNYKESFSLNQVMKNIWVK-LMNRLIYFLFNYFIMPLIRRFFFLTKSEQTLH-TIFFDRK
Sc.        58  LPLNGYLPFDSLLKKLRLK-LAICFISWLFRQLIPKIIQTFFYCTELSTVT-IVYFRHD
Ca.        58  LGANEKIHMDDLFRGIRLK-FLKGYLWWLFEHLLKNILRSFWYITETSSIVS-LNYFPQY
consensus  61  l kye lslqelm kikvr ilakflfwlfd lvv llrsffyiTett    lfyyrk
                                     Motif 1           Motif 2
h.        116  VWSKLQSI-GIRQHLK-LRELSEAEVR-SRLRFIPKPDG-LRPIMNMDYVVGARTFR-AE
m.        116  VWSKLQSI-GVRQHLE-LRELSQEEVR-CRLRFIPKPNG-LRPIMNMSYSMGTRALG-AQ
o.        116  IWNMIMRL-SIDDLLK-LKQVEKKEMR-GKLRLIPKGDT-FRPIMTFNRKIPNQVGK-MT
E.        116  IWDVIMKM-SIADLKK-LAEVQEKEVE-GKLRLIPKKTT-FRPIMTFNKKIVNSDRK-LT
T.        116  IWKLVSKL-TIVKLEE-UEKVEEKLIP-GKLRIIPKKGS-FRPIMTFLRKDKQKNIK-LN
Sp.       116  IWKLLCRP-FITSMKM-FEKINENNVR-AVIRLLPKKNT-FRLITNLRKRFLIKQMG-VS
Plasmodium 116 IWNHFTKI-FIKKMKK-LWEINKKSVR-LRINWIPKKKG-LRPLINLSTLNVPEIVK-VS
Sc.       116  TWNKLITP-FIVEYFK-LMENNVCRNH-SKMRIIPKKSN-FRIIAIPCRGADEEEFT-KN
Ca.       116  LWKELYES-WVSKYAK-LVKMPSKIQR-GKIKLIPKRSS-FRVICVPIKRSLKLLNK-LP
consensus 121  iW l ri fi  l k lrelqekevr gklrliPKk t fRpivnm rkvv r lk mt h.        171  RLTSRVKALFSVLNYE-ARRPGLLGASVLGLDDIHRAWRTFVLRVR-PELYFVKVDVTGA
m.        171  HFTQRLKTLFSMLNYE-TKHPHLMGSSVLGMNDIYRTWRAFVLRVR-PRMYFVKADVTGA
o.        171  TNNKLQTAHMMLKNLK-KMFKHSFGFAVFNYDDIMKRYENFVQKWK-PKLYFVAMDIEKC
E.        171  TNTKLLNSHLMLKTLK-RMFKDPFGFAVFNYDDVMKKYEEFVCKWK-PKLFFATMDIEKC
T.        171  LNQILMDSQLVFRNLK-DMLGQKIGYSVFDNKQISEKFAQFIEKWK-PQLYMVILDIKKC
Sp.       171  TNQTLRPVASLLKHLI-NEESSGIPFNLEVYMKLLTFKKDLLKHRM-RKKYFVRIDIKSC
Plasmodium 171 LNNICNFSLKCLGNMR-NSLFKNTLTKTGEIELKLKKWLHYLKNWF-IYAYICIGDFSNC
Sc.       171  AIQPTQKILEYLRNKR-PTSFTKIYSPTQIADRLKEFKQRLLKKFN-PELYFMKFDMKSC
Ca.       171  VGQILRLKLSKLRDTY-ESYRASVHSSSDVAEKILDYRDSLLTRLG-PKLFILKSDMKEC
consensus 181  nq  lv tl mlknlk       lg sv  ddimrrw  fv kwr pklyfkvDik c
```

FIG. 2B

|  |  | Motif A | Motif B' |
|---|---|---|---|
| h. | 229 | YDTIPQDRLTEVIASIIKPQN-SPLRDAVVIEQS- | YVQCQGIPQGSILSTLLCSLCYGDM |
| m. | 229 | YDAIPQGRLVEVVANMIRHSE-SALRNSVVIEQS- | YTQCQGIPQGSSLSTLLCSLCFGDM |
| o. | 229 | YDNVDCERVVNFLQKSDLMDK-LNMKRTIIVEQE- | YRQMKGIPQGLCVSYILSSFYYANL |
| E. | 229 | YDSVNREKLSTFLKTTKLLSS-LNAKKILIVEAK- | YRQTKGIPQGLCVSSILSSFYYATL |
| T. | 229 | YDSIDQMKLLNFFNQSDLIQD-SLYDDDQILQK- | FRQKRGIPQGLNISGVLCSFYFGKL |
| Sp. | 229 | YDRIKQDLMFRIVKKKLKDPEI-TLFVDFVDYWTK- | YLQKVGIPQGSILSSFLCHFYMEDL |
| Plasmodium | 229 | YEHINHNYLFKILKNFFDNIN-YIFADSYKSLQV- | ISNIYGLPQGFSLSNILCSLYYAYL |
| Sc. | 229 | YDSIPRMEQMRTLKDALRNEN-ELYIDNVRTVHL- | YIREDGLFQGSSLSAPIVDLVYDDL |
| Ca. | 229 | YDRLSQPVLMKRLEELFENQD-KSLVDKTKTIAL- | YKRKRGVFQGFSLLSIFCDILYSAM |
| consensus | 241 | Ydti qdrlvrvlk  ik  e sl rdsvvieq  ykq kGipQGsslstilcslyygdl |

|  |  | Motif C | Motif D |
|---|---|---|---|
| h. | 287 | E-NKLFAGIRRD-LLLRLVDDFLLVTPHLTHAKTFIRTLVR- | GVPEYGCVVNLRKTVVNF |
| m. | 287 | E-NKLFAEVQRD-LLLRFVDDFLLVTPHLDQAKTFISTLVR- | GVPEYGCMINLQKTVVNF |
| o. | 287 | E-ENALQFLRKE-LLMRLTDDYLLMTTEKNNAMLFIEKLYQ- | LSLGNFFKFHMKKLKTNF |
| E. | 287 | E-ESSLQFLRDE-LLMRLTDDYLLITTQENNAVLFIEKLIN- | VSRENGFKFNMKKLQTSF |
| T. | 287 | E-EEYTQFLKNA-LLMRLTDDYLFISDSQQNALNLIVQLQN- | CANNNGFMFNDQKITTNF |
| Sp. | 287 | I-DEYLSFTKKK-VLLRVVDDFLFITVNKKDAKKFLNLSLR- | GFEKHNFSTSLEKTVLNF |
| Plasmodium | 287 | D-EEFQNLLYSE-LILRFLDDFLFITLNKKNIKIFKNLLLK- | CKKKYIKHIKKMKYMNNF |
| Sc. | 287 | L-EFMSEFKASP-LILKLADDFLIISTDQDQVINIKKLAMG- | GFQKYNAKANRDKILAVS |
| Ca. | 287 | V-HDCFQFLWKS-LFVRLVDDFLLVTPDSNIYDQVHNLLSG- | ILESYGAFVNKDKTVVVN |
| consensus | 301 | e eey qflrrd lllrlvDDFLlit  nnak fl llvr g  ygfkvnl Ktvvnf |

|  |  | Motif E |
|---|---|---|
| h. | 344 | -QMPAHGLFPWCGLLLDTRTLE |
| m. | 344 | -QIPAHCLFPWCGLLLDTQTLE |
| o. | 344 | -DSINDDLFHWIGISIDIKTLN |
| E. | 344 | -QNIVQDYCDWIGISIDMKTLA |
| T. | 344 | -KISVQNECQWIGKSIDMNTLE |
| Sp. | 344 | -FNESKKRMPFEGFSVNMRSLD |
| Plasmodium | 344 | -NITPVTSIEWLNNSYTFDFIN |
| Sc. | 344 | -QSDDDTVIQFCAMHIFVKELE |
| Ca. | 344 | -QTTTKTSIDFVGLEVNTTDLS |
| consensus | 361 | qm  h lm wiglsidirtle |

TERT RTPCR ON TOTAL RNA OF *Plasmodium falciparum*

RT-PCR ON TOTAL RNA OF *Candida albicans*

FIG. 6

```
              10        20        30        40        50        60
Rice 129699   TTAATGAGGTTCATTGATGATTTCATATTTATCTCTTTCTCACTGGAGCATGCTCAAAAA
              ::: ::::  ::  :::::::::  :  :::  :::  :  :::  ::::    ::  ::  ::          :
Arab    -     TTACTGAGATTTATTGATGACTACATTTTTGTGTCTACCTCAAGAGATCAGGCGAGTAGC
              10        20        30        40        50        60

70        80        90       100       110       120
Rice 129699   TTCCTCAATAGGATGAGAAGAGGTTTTGTGTTCTACAATTGCTACATGAACGACAGCAAA
              :::       :   :::   :::             ::   :::      :::::   ::::   ::::::::::    :    :::
Arab    -     TTCTATCACAGGTTGAAGCATGGATTTAAAGATTACAACTGCTTCATGAACGAAACAAAA
              70        80        90       100       110       120

130       140       150       160       170
Rice 129699   TATGGCTTTAATTTCTGTGCT------GGAAATAGTGAGCCTTCCTCTAATAGACTCTAC
              :      ::   :   :   ::::::     :   :          :   :   ::::       :   :::   :   ::::::::   : :
Arab    -     TTCTGCATAAATTTTGAAGATAAAGAAGAACATAG---GTGTTCTTATAATAGAATGTTT
                       130       140       150       160       170

180       190       200       210       220       230
Rice 129699   AGGGGTGATGATGGAGTCTCATTCATGCCATGGAGTGGTTTGCTAATAAATTGTGAAACT
              ::::   :::   :::::::::   :   ::   :         :::::   ::::::::::   ::   ::::            ::
Arab    -     GTGGGCGATAATGGAGTTCCTTTTGTCAGATGGACGGGTTTGCTTATTAATTCCCGCACA
              180       190       200       210       220       230

240       250       260       270       280       290
Rice 129699   TTGGAAATTCAAGCTGATTATACGAGGTATGACTGTTGAAATTTGTTTTTAGCTCATTGG
              ::  :::   ::::::   :::   ::   ::   ::::   ::  ::                                             ::
Arab    -     TTTGAAGTTCAAGTTGACTACACAAGGTCTGCCT
```

ALIGNMENT: RICE-ARABIDOPSIS NUCLEOTIDE SEQUENCE.

SEQUENCE LISTING

```
<160> NUMBER OF SEQ ID NOS: 49

<210> SEQ ID NO 1
<211> LENGTH: 2714
<212> TYPE: DNA
<213> ORGANISM: Candida albicans
<220> FEATURE:
<221> NAME/KEY: CDS
<222> LOCATION: (50)..(2650)
<223> OTHER INFORMATION: TERT gene, strain 3153(A)
<220> FEATURE:
<221> NAME/KEY: misc_difference
<222> LOCATION: (389)..(2617)
<223> OTHER INFORMATION: Amino acids at positions 114, 452, 487, 538,
      634, 735 and 856 are translated as Ser in C. albicans, not as Leu
      (from ctg codons).

<400> SEQUENCE: 1
cgttgttatt cacgcgtatc gtgagatatc atttcaaaga accacatac atg acc gtc      58
                                                    Met Thr Val
                                                      1 aaa gta aat gag aag aag act tta ctt cag tat gtt cta gat aat aca      106
Lys Val Asn Glu Lys Lys Thr Leu Leu Gln Tyr Val Leu Asp Asn Thr
  5                  10                  15 agc aat gac gtg cca ttg cta cct agt ttg aaa gag tac atg gag acg      154
Ser Asn Asp Val Pro Leu Leu Pro Ser Leu Lys Glu Tyr Met Glu Thr
 20                  25                  30                  35 gtg ctt gta tac aaa tcc ata aaa cgg cct cta cca gcg att cga cca      202
Val Leu Val Tyr Lys Ser Ile Lys Arg Pro Leu Pro Ala Ile Arg Pro
                 40                  45                  50 caa gaa tca ttt gac gaa ttt atg aaa gag ttg gtg acc cgt tta gtt      250
Gln Glu Ser Phe Asp Glu Phe Met Lys Glu Leu Val Thr Arg Leu Val
             55                  60                  65 atg gaa aaa tcg aat aat gtt ata gct tat ggg tat aag act tct gca      298
Met Glu Lys Ser Asn Asn Val Ile Ala Tyr Gly Tyr Lys Thr Ser Ala
         70                  75                  80 atg gag agt cga agt ata ttt aca acg ttt cat tcg agt ggg aat ttt      346
Met Glu Ser Arg Ser Ile Phe Thr Thr Phe His Ser Ser Gly Asn Phe
     85                  90                  95 att tta act cac att aca agc cat aac tgg agt aca ata ttt ctg tta      394
Ile Leu Thr His Ile Thr Ser His Asn Trp Ser Thr Ile Phe Leu Leu
100                 105                 110                 115
```

```
ctc gga cct aaa aaa ttt cta gag cta tta gtt aat aat aag ggg ttt       442
Leu Gly Pro Lys Lys Phe Leu Glu Leu Leu Val Asn Asn Lys Gly Phe
            120                 125                 130 gtt agt aag gtg aat ggt gaa tct gtg caa ata ttc ggt gac gtg aac       490
Val Ser Lys Val Asn Gly Glu Ser Val Gln Ile Phe Gly Asp Val Asn
            135                 140                 145 tct cac aga aag gct gtc gtc gtt tcc aaa tac att acc aaa ttc aat       538
Ser His Arg Lys Ala Val Val Val Ser Lys Tyr Ile Thr Lys Phe Asn
            150                 155                 160 gtg ctt tac aac tcc tat tcc agg gac ttc tca cgc ttt gag atg ata       586
Val Leu Tyr Asn Ser Tyr Ser Arg Asp Phe Ser Arg Phe Glu Met Ile
        165                 170                 175 aga ccc agt att caa act ata tta cag gat att ctt tcc ttt tct ggt       634
Arg Pro Ser Ile Gln Thr Ile Leu Gln Asp Ile Leu Ser Phe Ser Gly
180                 185                 190                 195 ttg aat cct gga aga tca tct aaa aga tat cga ggc ttc aaa agt ttg       682
Leu Asn Pro Gly Arg Ser Ser Lys Arg Tyr Arg Gly Phe Lys Ser Leu
                200                 205                 210 ctc tcg aga att att gct aat gat aag aaa tgt aga tac gac att cta       730
Leu Ser Arg Ile Ile Ala Asn Asp Lys Lys Cys Arg Tyr Asp Ile Leu
            215                 220                 225 tat gct aag ttt att ggt acg tca aaa tgc aat ttt gct aat gtg gtg       778
Tyr Ala Lys Phe Ile Gly Thr Ser Lys Cys Asn Phe Ala Asn Val Val
            230                 235                 240 agt aat aag aca gaa ata tcc cag gta att caa ttt gta ctt tta gta       826
Ser Asn Lys Thr Glu Ile Ser Gln Val Ile Gln Phe Val Leu Leu Val
        245                 250                 255 ttg ggt aaa ttg tta cct ttg gat gct tgg gga ggt gtt tcc aat aaa       874
Leu Gly Lys Leu Leu Pro Leu Asp Ala Trp Gly Gly Val Ser Asn Lys
260                 265                 270                 275 aag att att aag gac cga gtg gta gat ttt ttg tta ctt ggg gca aat       922
Lys Ile Ile Lys Asp Arg Val Val Asp Phe Leu Leu Leu Gly Ala Asn
                280                 285                 290 gaa aag ata cat atg gat gat tta ttt aga gga att aga cta aaa gat       970
Glu Lys Ile His Met Asp Asp Leu Phe Arg Gly Ile Arg Leu Lys Asp
            295                 300                 305 ttc aag tgg ttg ggc aga gct cac caa att tct tcg aaa caa gat ttc      1018
Phe Lys Trp Leu Gly Arg Ala His Gln Ile Ser Ser Lys Gln Asp Phe
            310                 315                 320 gag ctc cga aca gct ttt cta aaa ggg tat cta tgg tgg ttg ttt gaa      1066
Glu Leu Arg Thr Ala Phe Leu Lys Gly Tyr Leu Trp Trp Leu Phe Glu
        325                 330                 335 cat tta ctt aaa aat att ctc cgt tct ttc tgg tac att act gaa act      1114
His Leu Leu Lys Asn Ile Leu Arg Ser Phe Trp Tyr Ile Thr Glu Thr
340                 345                 350                 355 tca agt ata gtg agt tca gag ttg aat tat ttt cct cag tat tta tgg      1162
Ser Ser Ile Val Ser Ser Glu Leu Asn Tyr Phe Pro Gln Tyr Leu Trp
                360                 365                 370 aaa gag cta tac gag tca tgg gtg tct aaa tat gca aag aat aat ctt      1210
Lys Glu Leu Tyr Glu Ser Trp Val Ser Lys Tyr Ala Lys Asn Asn Leu
            375                 380                 385 gtg aaa atg cca tca aag atc caa aga gaa caa cta cca tgt ggg aaa      1258
Val Lys Met Pro Ser Lys Ile Gln Arg Glu Gln Leu Pro Cys Gly Lys
            390                 395                 400 att aaa ctc ata ccc aag cgc tcg agc ttt cgt gtt att tgt gta cct      1306
Ile Lys Leu Ile Pro Lys Arg Ser Ser Phe Arg Val Ile Cys Val Pro
        405                 410                 415 ata aaa cga tcc ttg aaa cta ttg aac aaa aaa ttg gaa ttg gac aca      1354
Ile Lys Arg Ser Leu Lys Leu Leu Asn Lys Lys Leu Glu Leu Asp Thr
420                 425                 430                 435
```

-continued

| | | |
|---|---|---|
| ttg gaa aag gag aaa agg gaa ttt gaa agg tac aga aaa gag gtt tta<br>Leu Glu Lys Glu Lys Arg Glu Phe Glu Arg Tyr Arg Lys Glu Val Leu<br>440 445 450 | 1402 |
| ctg cca gtg gga caa ata cta cgc ttg aaa tta tcg aaa cta aga gat<br>Leu Pro Val Gly Gln Ile Leu Arg Leu Lys Leu Ser Lys Leu Arg Asp<br>455 460 465 | 1450 |
| aca tat gaa agc tat agg gct tca gta cat tcc agt tct gat gtg gct<br>Thr Tyr Glu Ser Tyr Arg Ala Ser Val His Ser Ser Ser Asp Val Ala<br>470 475 480 | 1498 |
| gaa aag ata ctg gat tat aga gac tcc ttg tta acc aga ttt ggc gaa<br>Glu Lys Ile Leu Asp Tyr Arg Asp Ser Leu Leu Thr Arg Phe Gly Glu<br>485 490 495 | 1546 |
| atc cct aag ctt ttc atc tta aag ttt gac atg aaa gaa tgt tat gat<br>Ile Pro Lys Leu Phe Ile Leu Lys Phe Asp Met Lys Glu Cys Tyr Asp<br>500 505 510 515 | 1594 |
| aga ctc agc caa cct gta ttg atg aaa aaa cta gag gaa ctt ttc gaa<br>Arg Leu Ser Gln Pro Val Leu Met Lys Lys Leu Glu Glu Leu Phe Glu<br>520 525 530 | 1642 |
| aac caa gat aat aag act ctg tat tat gtt cga tac tac gct cag ttg<br>Asn Gln Asp Asn Lys Thr Leu Tyr Tyr Val Arg Tyr Tyr Ala Gln Leu<br>535 540 545 | 1690 |
| gac gcg tca cat aaa ttg aaa aaa gtg aaa acc act ata gat acc cag<br>Asp Ala Ser His Lys Leu Lys Lys Val Lys Thr Thr Ile Asp Thr Gln<br>550 555 560 | 1738 |
| tat cac aat tta aac att ttg tcg agc tca agg cat ctc agt aat tgt<br>Tyr His Asn Leu Asn Ile Leu Ser Ser Ser Arg His Leu Ser Asn Cys<br>565 570 575 | 1786 |
| aaa tct ttg gtc gat aag acc aag aca ata gcg ttg caa aaa ggt aac<br>Lys Ser Leu Val Asp Lys Thr Lys Thr Ile Ala Leu Gln Lys Gly Asn<br>580 585 590 595 | 1834 |
| att ttg gaa gtt tgt cga agc caa atc tac gat gtt gtt ggt tca gtt<br>Ile Leu Glu Val Cys Arg Ser Gln Ile Tyr Asp Val Val Gly Ser Val<br>600 605 610 | 1882 |
| aaa gat gca cga ggg aat tta cac cta tat aaa agg aag agg ggc gtg<br>Lys Asp Ala Arg Gly Asn Leu His Leu Tyr Lys Arg Lys Arg Gly Val<br>615 620 625 | 1930 |
| ttt cag gga ttc tca ttg ctg tct ata ttt tgt gac atc ctc tat agt<br>Phe Gln Gly Phe Ser Leu Leu Ser Ile Phe Cys Asp Ile Leu Tyr Ser<br>630 635 640 | 1978 |
| gca atg gtt cat gat tgt ttt caa ttc tta tgg aag tcg aaa cag gat<br>Ala Met Val His Asp Cys Phe Gln Phe Leu Trp Lys Ser Lys Gln Asp<br>645 650 655 | 2026 |
| ttt tta ttt gta cga ttg gta gat gac ttt tta ctt gta acg ccc gat<br>Phe Leu Phe Val Arg Leu Val Asp Asp Phe Leu Leu Val Thr Pro Asp<br>660 665 670 675 | 2074 |
| tcg aat att tat gat caa gtg cac aat ata tta tca gga aaa ata ctt<br>Ser Asn Ile Tyr Asp Gln Val His Asn Ile Leu Ser Gly Lys Ile Leu<br>680 685 690 | 2122 |
| gag agc tat gga gct ttt gtt aat aaa gat aaa aca gtc gtt gtt aat<br>Glu Ser Tyr Gly Ala Phe Val Asn Lys Asp Lys Thr Val Val Val Asn<br>695 700 705 | 2170 |
| caa aca acc acg aaa aca agt ata gat ttc gtt ggg ctt gaa gtg aat<br>Gln Thr Thr Thr Lys Thr Ser Ile Asp Phe Val Gly Leu Glu Val Asn<br>710 715 720 | 2218 |
| aca aca gat cta agc atc aaa agg aac tcc ggt ctg ata agt ttg gtt<br>Thr Thr Asp Leu Ser Ile Lys Arg Asn Ser Gly Leu Ile Ser Leu Val<br>725 730 735 | 2266 |
| acg aca aac ttc aga aca ttc aag act tta gtt aaa tat tta aag act<br>Thr Thr Asn Phe Arg Thr Phe Lys Thr Leu Val Lys Tyr Leu Lys Thr | 2314 |

-continued

```
740                745                750                755
ttc tat caa ttg aat ttg gag ggg ttt ctc ttg gac tgt tct ttt ggg    2362
Phe Tyr Gln Leu Asn Leu Glu Gly Phe Leu Leu Asp Cys Ser Phe Gly
                760                765                770 gta ttg gaa aac gtg ctt gaa aat atg gga tcc ctc ctt agg ttg gtt    2410
Val Leu Glu Asn Val Leu Glu Asn Met Gly Ser Leu Leu Arg Leu Val
                775                780                785 ttg agg gaa ttc aaa aca aag ttt acc tcc att gtc aaa tat gat aca    2458
Leu Arg Glu Phe Lys Thr Lys Phe Thr Ser Ile Val Lys Tyr Asp Thr
                790                795                800 ttt cat tgt tac aaa ttt atc aaa ttt cta tat gac ata agt aat tac    2506
Phe His Cys Tyr Lys Phe Ile Lys Phe Leu Tyr Asp Ile Ser Asn Tyr
                805                810                815 aca atc gtt aaa tat gtt gaa aca aac agc gac tgg gaa ggt gca cct    2554
Thr Ile Val Lys Tyr Val Glu Thr Asn Ser Asp Trp Glu Gly Ala Pro
820                825                830                835 gaa cta ttg aat tgc att aaa cag ata att gtc aag gag ttt tcc tct    2602
Glu Leu Leu Asn Cys Ile Lys Gln Ile Ile Val Lys Glu Phe Ser Ser
                840                845                850 ttt gag agt tac ctg gaa ata gtc gag tgg gta caa aca ttg aat ata    2650
Phe Glu Ser Tyr Leu Glu Ile Val Glu Trp Val Gln Thr Leu Asn Ile
                855                860                865 taaatacact gctcatatac ccccaaacga gctttttaaa ttctcgatat ctctcaattg    2710
tcgc                                                                  2714

<210> SEQ ID NO 2
<211> LENGTH: 867
<212> TYPE: PRT
<213> ORGANISM: Candida albicans

<400> SEQUENCE: 2

Met Thr Val Lys Val Asn Glu Lys Lys Thr Leu Leu Gln Tyr Val Leu
  1               5                  10                  15

Asp Asn Thr Ser Asn Asp Val Pro Leu Leu Pro Ser Leu Lys Glu Tyr
                 20                  25                  30

Met Glu Thr Val Leu Val Tyr Lys Ser Ile Lys Arg Pro Leu Pro Ala
             35                  40                  45

Ile Arg Pro Gln Glu Ser Phe Asp Glu Phe Met Lys Glu Leu Val Thr
         50                  55                  60

Arg Leu Val Met Glu Lys Ser Asn Asn Val Ile Ala Tyr Gly Tyr Lys
 65                  70                  75                  80

Thr Ser Ala Met Glu Ser Arg Ser Ile Phe Thr Thr Phe His Ser Ser
                 85                  90                  95

Gly Asn Phe Ile Leu Thr His Ile Thr Ser His Asn Trp Ser Thr Ile
                100                 105                 110

Phe Leu Leu Leu Gly Pro Lys Lys Phe Leu Glu Leu Leu Val Asn Asn
            115                 120                 125

Lys Gly Phe Val Ser Lys Val Asn Gly Glu Ser Val Gln Ile Phe Gly
        130                 135                 140

Asp Val Asn Ser His Arg Lys Ala Val Val Ser Lys Tyr Ile Thr
145                 150                 155                 160

Lys Phe Asn Val Leu Tyr Asn Ser Tyr Ser Arg Asp Phe Ser Arg Phe
                165                 170                 175

Glu Met Ile Arg Pro Ser Ile Gln Thr Ile Leu Gln Asp Ile Leu Ser
            180                 185                 190

Phe Ser Gly Leu Asn Pro Gly Arg Ser Ser Lys Arg Tyr Arg Gly Phe
```

-continued

```
            195                 200                 205
Lys Ser Leu Leu Ser Arg Ile Ile Ala Asn Asp Lys Lys Cys Arg Tyr
            210                 215                 220
Asp Ile Leu Tyr Ala Lys Phe Ile Gly Thr Ser Lys Cys Asn Phe Ala
225                 230                 235                 240
Asn Val Val Ser Asn Lys Thr Glu Ile Ser Gln Val Ile Gln Phe Val
                    245                 250                 255
Leu Leu Val Leu Gly Lys Leu Pro Leu Asp Ala Trp Gly Gly Val
                260                 265                 270
Ser Asn Lys Lys Ile Ile Lys Asp Arg Val Val Asp Phe Leu Leu Leu
            275                 280                 285
Gly Ala Asn Glu Lys Ile His Met Asp Asp Leu Phe Arg Gly Ile Arg
            290                 295                 300
Leu Lys Asp Phe Lys Trp Leu Gly Arg Ala His Gln Ile Ser Ser Lys
305                 310                 315                 320
Gln Asp Phe Glu Leu Arg Thr Ala Phe Leu Lys Gly Tyr Leu Trp Trp
                    325                 330                 335
Leu Phe Glu His Leu Leu Lys Asn Ile Leu Arg Ser Phe Trp Tyr Ile
                340                 345                 350
Thr Glu Thr Ser Ser Ile Val Ser Ser Glu Leu Asn Tyr Phe Pro Gln
                355                 360                 365
Tyr Leu Trp Lys Glu Leu Tyr Glu Ser Trp Val Ser Lys Tyr Ala Lys
            370                 375                 380
Asn Asn Leu Val Lys Met Pro Ser Lys Ile Gln Arg Glu Gln Leu Pro
385                 390                 395                 400
Cys Gly Lys Ile Lys Leu Ile Pro Lys Arg Ser Ser Phe Arg Val Ile
                    405                 410                 415
Cys Val Pro Ile Lys Arg Ser Leu Lys Leu Asn Lys Lys Leu Glu
                420                 425                 430
Leu Asp Thr Leu Glu Lys Glu Lys Arg Glu Phe Glu Arg Tyr Arg Lys
            435                 440                 445
Glu Val Leu Leu Pro Val Gly Gln Ile Leu Arg Leu Lys Leu Ser Lys
            450                 455                 460
Leu Arg Asp Thr Tyr Glu Ser Tyr Arg Ala Ser Val His Ser Ser Ser
465                 470                 475                 480
Asp Val Ala Glu Lys Ile Leu Asp Tyr Arg Asp Ser Leu Leu Thr Arg
                    485                 490                 495
Phe Gly Glu Ile Pro Lys Leu Phe Ile Leu Lys Phe Asp Met Lys Glu
                500                 505                 510
Cys Tyr Asp Arg Leu Ser Gln Pro Val Leu Met Lys Lys Leu Glu Glu
                515                 520                 525
Leu Phe Glu Asn Gln Asp Asn Lys Thr Leu Tyr Tyr Val Arg Tyr Tyr
            530                 535                 540
Ala Gln Leu Asp Ala Ser His Lys Leu Lys Lys Val Lys Thr Thr Ile
545                 550                 555                 560
Asp Thr Gln Tyr His Asn Leu Asn Ile Leu Ser Ser Arg His Leu
                    565                 570                 575
Ser Asn Cys Lys Ser Leu Val Asp Lys Thr Lys Thr Ile Ala Leu Gln
                580                 585                 590
Lys Gly Asn Ile Leu Glu Val Cys Arg Ser Gln Ile Tyr Asp Val Val
            595                 600                 605
Gly Ser Val Lys Asp Ala Arg Gly Asn Leu His Leu Tyr Lys Arg Lys
            610                 615                 620
```

```
Arg Gly Val Phe Gln Gly Phe Ser Leu Leu Ser Ile Phe Cys Asp Ile
625                 630                 635                 640

Leu Tyr Ser Ala Met Val His Asp Cys Phe Gln Phe Leu Trp Lys Ser
            645                 650                 655

Lys Gln Asp Phe Leu Phe Val Arg Leu Val Asp Asp Phe Leu Leu Val
            660                 665                 670

Thr Pro Asp Ser Asn Ile Tyr Asp Gln Val His Asn Ile Leu Ser Gly
            675                 680                 685

Lys Ile Leu Glu Ser Tyr Gly Ala Phe Val Asn Lys Asp Lys Thr Val
690                 695                 700

Val Val Asn Gln Thr Thr Thr Lys Thr Ser Ile Asp Phe Val Gly Leu
705                 710                 715                 720

Glu Val Asn Thr Thr Asp Leu Ser Ile Lys Arg Asn Ser Gly Leu Ile
                725                 730                 735

Ser Leu Val Thr Thr Asn Phe Arg Thr Phe Lys Thr Leu Val Lys Tyr
                740                 745                 750

Leu Lys Thr Phe Tyr Gln Leu Asn Leu Glu Gly Phe Leu Leu Asp Cys
            755                 760                 765

Ser Phe Gly Val Leu Glu Asn Val Leu Glu Asn Met Gly Ser Leu Leu
770                 775                 780

Arg Leu Val Leu Arg Glu Phe Lys Thr Lys Phe Thr Ser Ile Val Lys
785                 790                 795                 800

Tyr Asp Thr Phe His Cys Tyr Lys Phe Ile Lys Phe Leu Tyr Asp Ile
                805                 810                 815

Ser Asn Tyr Thr Ile Val Lys Tyr Val Glu Thr Asn Ser Asp Trp Glu
                820                 825                 830

Gly Ala Pro Glu Leu Leu Asn Cys Ile Lys Gln Ile Ile Val Lys Glu
            835                 840                 845

Phe Ser Ser Phe Glu Ser Tyr Leu Glu Ile Val Glu Trp Val Gln Thr
850                 855                 860

Leu Asn Ile
865

<210> SEQ ID NO 3
<211> LENGTH: 2714
<212> TYPE: DNA
<213> ORGANISM: Candida albicans
<220> FEATURE:
<221> NAME/KEY: CDS
<222> LOCATION: (50)..(2650)
<223> OTHER INFORMATION: TERT gene, strain 3153(A)
<220> FEATURE:
<221> NAME/KEY: misc_difference
<222> LOCATION: (389)..(2617)
<223> OTHER INFORMATION: Amino acids at positions 114, 452, 487, 538,
      634, 735 and 856 are translated as Ser in C. albicans, not as Leu
      (from ctg codons).

<400> SEQUENCE: 3
cgttgttatt cacgcgtatc gtgagatatc atttcaaaga accacatac atg acc gtc      58
                                                      Met Thr Val
                                                        1 aaa gta aat gag aag aag act tta ctt cag tat gtt cta gat aat aca      106
Lys Val Asn Glu Lys Lys Thr Leu Leu Gln Tyr Val Leu Asp Asn Thr
    5               10                  15 agc aat gaa gtg cca ttg cta cct agt ttg aaa gag tac atg gag acg      154
Ser Asn Glu Val Pro Leu Leu Pro Ser Leu Lys Glu Tyr Met Glu Thr
20                  25                  30                  35
```

-continued

```
gtg ctt gta tac caa tcc ata aaa cgg cct cta cca gcg att cga cca      202
Val Leu Val Tyr Gln Ser Ile Lys Arg Pro Leu Pro Ala Ile Arg Pro
             40                  45                  50 caa gaa tca ttt gac gaa ttt atg aaa gag ttg gtg acc cgt tta gtt      250
Gln Glu Ser Phe Asp Glu Phe Met Lys Glu Leu Val Thr Arg Leu Val
         55                  60                  65 atg gaa aaa tcg aat aat gtt ata gct tat ggg tat aag acc tcc gca      298
Met Glu Lys Ser Asn Asn Val Ile Ala Tyr Gly Tyr Lys Thr Ser Ala
     70                  75                  80 atg gag agt cga agt ata ttt aca acg ttt cat tcg agt ggg aat ttt      346
Met Glu Ser Arg Ser Ile Phe Thr Thr Phe His Ser Ser Gly Asn Phe
 85                  90                  95 att tta act cac att aca agc cat aac tgg agt aca ata ttt ctg tta      394
Ile Leu Thr His Ile Thr Ser His Asn Trp Ser Thr Ile Phe Leu Leu
100                 105                 110                 115 ctc gga cct aaa aaa ttt cta gag cta tta gtt aat aat aag ggg ttt      442
Leu Gly Pro Lys Lys Phe Leu Glu Leu Leu Val Asn Asn Lys Gly Phe
                120                 125                 130 gtt agt aag gtg aat ggt gaa tct gtg caa ata ttc ggt gac gtg aac      490
Val Ser Lys Val Asn Gly Glu Ser Val Gln Ile Phe Gly Asp Val Asn
            135                 140                 145 tct cac aga aag gct gtc gtc gtt tcc aaa tac att acc aaa ttc aat      538
Ser His Arg Lys Ala Val Val Val Ser Lys Tyr Ile Thr Lys Phe Asn
        150                 155                 160 gtg ctt tac aac tcc tat tcc agg gac ttc tca cgc ttt gag atg ata      586
Val Leu Tyr Asn Ser Tyr Ser Arg Asp Phe Ser Arg Phe Glu Met Ile
    165                 170                 175 aga ccc agt att caa act ata tta cag gat att ctt tcc ttt tct ggt      634
Arg Pro Ser Ile Gln Thr Ile Leu Gln Asp Ile Leu Ser Phe Ser Gly
180                 185                 190                 195 ttg aat cct gga aga tca tcc aaa aga tat cga ggc ttc aaa agt ttg      682
Leu Asn Pro Gly Arg Ser Ser Lys Arg Tyr Arg Gly Phe Lys Ser Leu
                200                 205                 210 ctc tcg aga att att gct aat gat aag aaa tgt aga tac gac att cta      730
Leu Ser Arg Ile Ile Ala Asn Asp Lys Lys Cys Arg Tyr Asp Ile Leu
            215                 220                 225 tat gct aag ttt att ggt acg tca aaa tgc aat ttt gct aat gtg gtg      778
Tyr Ala Lys Phe Ile Gly Thr Ser Lys Cys Asn Phe Ala Asn Val Val
        230                 235                 240 agt aat aag aca gaa ata tcc cag gta att caa ttt gta ctt tta gta      826
Ser Asn Lys Thr Glu Ile Ser Gln Val Ile Gln Phe Val Leu Leu Val
    245                 250                 255 ttg ggt aaa ttg tta cct ttg gat gct tgg gga ggt gtt tcc aat aaa      874
Leu Gly Lys Leu Leu Pro Leu Asp Ala Trp Gly Gly Val Ser Asn Lys
260                 265                 270                 275 aag att att aag gac cga gtg gta gat ttt ttg tta ctt ggg gca aat      922
Lys Ile Ile Lys Asp Arg Val Val Asp Phe Leu Leu Leu Gly Ala Asn
                280                 285                 290 gaa aag ata cat atg gat gat tta ttt aga gga att aga cta aaa gat      970
Glu Lys Ile His Met Asp Asp Leu Phe Arg Gly Ile Arg Leu Lys Asp
            295                 300                 305 ttc aag tgg ttg ggc aga gct cac caa att tct tcg aaa caa gat ttc     1018
Phe Lys Trp Leu Gly Arg Ala His Gln Ile Ser Ser Lys Gln Asp Phe
        310                 315                 320 gag ctc cga aca gct ttt cta aaa ggg tat cta tgg tgg ttg ttt gaa     1066
Glu Leu Arg Thr Ala Phe Leu Lys Gly Tyr Leu Trp Trp Leu Phe Glu
    325                 330                 335 cat tta ctt aaa aat att ctc cgt tct ttc tgg tac att act gaa act     1114
His Leu Leu Lys Asn Ile Leu Arg Ser Phe Trp Tyr Ile Thr Glu Thr
340                 345                 350                 355
```

-continued

```
tca agt ata gtg agt tta gag ttg aat tat ttt cct cag tat tta tgg    1162
Ser Ser Ile Val Ser Leu Glu Leu Asn Tyr Phe Pro Gln Tyr Leu Trp
        360                 365                 370 aaa gag cta tac gag tca tgg gtg tct aaa tat gca aag aat aat ctt    1210
Lys Glu Leu Tyr Glu Ser Trp Val Ser Lys Tyr Ala Lys Asn Asn Leu
            375                 380                 385 gtg aaa atg cca tca aag atc caa aga gaa caa cta cca tgt ggg aaa    1258
Val Lys Met Pro Ser Lys Ile Gln Arg Glu Gln Leu Pro Cys Gly Lys
        390                 395                 400 att aaa ctc ata ccc aag cgc tcg agc ttt cgt gtt att tgt gta cct    1306
Ile Lys Leu Ile Pro Lys Arg Ser Ser Phe Arg Val Ile Cys Val Pro
        405                 410                 415 ata aaa cga tcc ttg aaa cta ttg aac aaa aaa ttg gaa ttg gac aca    1354
Ile Lys Arg Ser Leu Lys Leu Leu Asn Lys Lys Leu Glu Leu Asp Thr
420                 425                 430                 435 ttg gaa aag gag aaa agg gaa ttt gaa agg tac aga aaa gag gtt tta    1402
Leu Glu Lys Glu Lys Arg Glu Phe Glu Arg Tyr Arg Lys Glu Val Leu
                440                 445                 450 ctg cca gtg gga caa ata cta cgc ttg aaa tta tcg aaa cta aga gat    1450
Leu Pro Val Gly Gln Ile Leu Arg Leu Lys Leu Ser Lys Leu Arg Asp
                455                 460                 465 aca tat gaa agc tat agg gct tca gta cat tcc agt tct gat gtg gct    1498
Thr Tyr Glu Ser Tyr Arg Ala Ser Val His Ser Ser Asp Val Ala
        470                 475                 480 gaa aag ata ctg gat tat aga gac tcc ttg tta acc aga ttt ggc gaa    1546
Glu Lys Ile Leu Asp Tyr Arg Asp Ser Leu Leu Thr Arg Phe Gly Glu
        485                 490                 495 atc cct aag ctt ttc atc tta aag ttt gac atg aaa gaa tgt tat gat    1594
Ile Pro Lys Leu Phe Ile Leu Lys Phe Asp Met Lys Glu Cys Tyr Asp
500                 505                 510                 515 aga ctc agc caa cct gta tta atg aaa aaa cta gag gaa ctt ttc gaa    1642
Arg Leu Ser Gln Pro Val Leu Met Lys Lys Leu Glu Glu Leu Phe Glu
                520                 525                 530 aac caa gat aat aag act ctg tat tat gtt cga tac tac gct cag ttg    1690
Asn Gln Asp Asn Lys Thr Leu Tyr Tyr Val Arg Tyr Tyr Ala Gln Leu
                535                 540                 545 gac gcg tca cat aaa ttg aaa aaa gtg aaa acc act ata gat acc cag    1738
Asp Ala Ser His Lys Leu Lys Lys Val Lys Thr Thr Ile Asp Thr Gln
        550                 555                 560 tat cac aat tta aac att ttg tcg agc tca agg cat ctc agt aat tgt    1786
Tyr His Asn Leu Asn Ile Leu Ser Ser Ser Arg His Leu Ser Asn Cys
        565                 570                 575 aaa tct ttg gtc gat aag acc aag aca ata gcg ttg caa aaa ggt aac    1834
Lys Ser Leu Val Asp Lys Thr Lys Thr Ile Ala Leu Gln Lys Gly Asn
580                 585                 590                 595 att ttg gaa gtt tgt cga agc caa atc tac gat gtt gtt ggt tca gtt    1882
Ile Leu Glu Val Cys Arg Ser Gln Ile Tyr Asp Val Val Gly Ser Val
                600                 605                 610 aaa gat gca cga ggg aat tta cac cta tat aaa agg aag agg ggc gtg    1930
Lys Asp Ala Arg Gly Asn Leu His Leu Tyr Lys Arg Lys Arg Gly Val
                615                 620                 625 ttt cag gga ttc tca ttg ctg tct ata ttt tgt gac atc cta tat agt    1978
Phe Gln Gly Phe Ser Leu Leu Ser Ile Phe Cys Asp Ile Leu Tyr Ser
        630                 635                 640 gca atg gtt cat gat tgt ttt caa ttc tta tgg aag tcg aaa cag gat    2026
Ala Met Val His Asp Cys Phe Gln Phe Leu Trp Lys Ser Lys Gln Asp
645                 650                 655 ttt tta ttt gta cga ttg gta gat gac ttt tta ctt gta acg ccc gat    2074
Phe Leu Phe Val Arg Leu Val Asp Asp Phe Leu Leu Val Thr Pro Asp
```

-continued

```
                660                 665                 670                 675
tcg aat att tat gat caa gtg cac aat ata tta tca gga aaa ata ctt              2122
Ser Asn Ile Tyr Asp Gln Val His Asn Ile Leu Ser Gly Lys Ile Leu
                    680                 685                 690 gag agc tat gga gct ttt gtt aat aaa gat aaa aca gtc gtt gtt aat              2170
Glu Ser Tyr Gly Ala Phe Val Asn Lys Asp Lys Thr Val Val Val Asn
                695                 700                 705 caa aca acc acg aaa cca agt ata gat ttc gtt ggg ctc gaa gtg aat              2218
Gln Thr Thr Thr Lys Pro Ser Ile Asp Phe Val Gly Leu Glu Val Asn
            710                 715                 720 aca aca gat cta agc atc aaa agg aac tcc ggt ctg ata agt ttg gtt              2266
Thr Thr Asp Leu Ser Ile Lys Arg Asn Ser Gly Leu Ile Ser Leu Val
        725                 730                 735 acg aca aac ttc aga aca ttc aag act tta gtt aag tat tta aag act              2314
Thr Thr Asn Phe Arg Thr Phe Lys Thr Leu Val Lys Tyr Leu Lys Thr
740                 745                 750                 755 ttc tat caa ttg aat ttg gag ggg ttt ctc ttg gac tgt tct ttt ggg              2362
Phe Tyr Gln Leu Asn Leu Glu Gly Phe Leu Leu Asp Cys Ser Phe Gly
                    760                 765                 770 gta ttg gaa aac gtg ctt gaa aat atg gga tcc ctc ctt agg ttg gtt              2410
Val Leu Glu Asn Val Leu Glu Asn Met Gly Ser Leu Leu Arg Leu Val
                775                 780                 785 ttg agg gaa ttc aaa aca aag ttt acc tcc att gtc aaa tat gat aca              2458
Leu Arg Glu Phe Lys Thr Lys Phe Thr Ser Ile Val Lys Tyr Asp Thr
            790                 795                 800 ttt cat tgt tac aaa ttt atc aaa ttt cta tat gac ata agt aat tac              2506
Phe His Cys Tyr Lys Phe Ile Lys Phe Leu Tyr Asp Ile Ser Asn Tyr
        805                 810                 815 aca atc gtt aaa tat gtt gaa aca aac agc gac tgg gat ggt gca cct              2554
Thr Ile Val Lys Tyr Val Glu Thr Asn Ser Asp Trp Asp Gly Ala Pro
820                 825                 830                 835 gaa cta ttg aat tgc att aaa cag ata att gtc aag gag ttt tcc tct              2602
Glu Leu Leu Asn Cys Ile Lys Gln Ile Ile Val Lys Glu Phe Ser Ser
                    840                 845                 850 ttt gag agt tac ctg gaa ata gtc gag tgg gta caa aca ttg aat ata              2650
Phe Glu Ser Tyr Leu Glu Ile Val Glu Trp Val Gln Thr Leu Asn Ile
                855                 860                 865 taaatacact gctcatatac ccccaaacga gcttttttaaa ttctcgatat ctctcaattg           2710
tcgc                                                                         2714

<210> SEQ ID NO 4
<211> LENGTH: 867
<212> TYPE: PRT
<213> ORGANISM: Candida albicans

<400> SEQUENCE: 4

Met Thr Val Lys Val Asn Glu Lys Lys Thr Leu Leu Gln Tyr Val Leu
 1               5                  10                  15

Asp Asn Thr Ser Asn Glu Val Pro Leu Leu Pro Ser Leu Lys Glu Tyr
                20                  25                  30

Met Glu Thr Val Leu Val Tyr Gln Ser Ile Lys Arg Pro Leu Pro Ala
            35                  40                  45

Ile Arg Pro Gln Glu Ser Phe Asp Glu Phe Met Lys Glu Leu Val Thr
        50                  55                  60

Arg Leu Val Met Glu Lys Ser Asn Asn Val Ile Ala Tyr Gly Tyr Lys
    65                  70                  75                  80

Thr Ser Ala Met Glu Ser Arg Ser Ile Phe Thr Thr Phe His Ser Ser
                85                  90                  95
```

-continued

Gly Asn Phe Ile Leu Thr His Ile Thr Ser His Asn Trp Ser Thr Ile
            100                 105                 110

Phe Leu Leu Leu Gly Pro Lys Lys Phe Leu Glu Leu Val Asn Asn
            115                 120                 125

Lys Gly Phe Val Ser Lys Val Asn Gly Glu Ser Val Gln Ile Phe Gly
            130                 135             140

Asp Val Asn Ser His Arg Lys Ala Val Val Ser Lys Tyr Ile Thr
145                 150                 155                 160

Lys Phe Asn Val Leu Tyr Asn Ser Tyr Ser Arg Asp Phe Ser Arg Phe
                165                 170                 175

Glu Met Ile Arg Pro Ser Ile Gln Thr Ile Leu Gln Asp Ile Leu Ser
            180                 185                 190

Phe Ser Gly Leu Asn Pro Gly Arg Ser Ser Lys Arg Tyr Arg Gly Phe
            195                 200                 205

Lys Ser Leu Leu Ser Arg Ile Ile Ala Asn Asp Lys Lys Cys Arg Tyr
            210                 215                 220

Asp Ile Leu Tyr Ala Lys Phe Ile Gly Thr Ser Lys Cys Asn Phe Ala
225                 230                 235                 240

Asn Val Val Ser Asn Lys Thr Glu Ile Ser Gln Val Ile Gln Phe Val
                245                 250                 255

Leu Leu Val Leu Gly Lys Leu Leu Pro Leu Asp Ala Trp Gly Gly Val
            260                 265                 270

Ser Asn Lys Lys Ile Ile Lys Asp Arg Val Val Asp Phe Leu Leu Leu
            275                 280                 285

Gly Ala Asn Glu Lys Ile His Met Asp Asp Leu Phe Arg Gly Ile Arg
            290                 295                 300

Leu Lys Asp Phe Lys Trp Leu Gly Arg Ala His Gln Ile Ser Ser Lys
305                 310                 315                 320

Gln Asp Phe Glu Leu Arg Thr Ala Phe Leu Lys Gly Tyr Leu Trp Trp
                325                 330                 335

Leu Phe Glu His Leu Leu Lys Asn Ile Leu Arg Ser Phe Trp Tyr Ile
            340                 345                 350

Thr Glu Thr Ser Ser Ile Val Ser Leu Glu Leu Asn Tyr Phe Pro Gln
            355                 360                 365

Tyr Leu Trp Lys Glu Leu Tyr Glu Ser Trp Val Ser Lys Tyr Ala Lys
            370                 375                 380

Asn Asn Leu Val Lys Met Pro Ser Lys Ile Gln Arg Glu Gln Leu Pro
385                 390                 395                 400

Cys Gly Lys Ile Lys Leu Ile Pro Lys Arg Ser Ser Phe Arg Val Ile
                405                 410                 415

Cys Val Pro Ile Lys Arg Ser Leu Lys Leu Asn Lys Lys Leu Glu
            420                 425                 430

Leu Asp Thr Leu Glu Lys Glu Lys Arg Glu Phe Glu Arg Tyr Arg Lys
            435                 440                 445

Glu Val Leu Leu Pro Val Gly Gln Ile Leu Arg Leu Lys Leu Ser Lys
            450                 455                 460

Leu Arg Asp Thr Tyr Glu Ser Tyr Arg Ala Ser Val His Ser Ser Ser
465                 470                 475                 480

Asp Val Ala Glu Lys Ile Leu Asp Tyr Arg Asp Ser Leu Leu Thr Arg
                485                 490                 495

Phe Gly Glu Ile Pro Lys Leu Phe Ile Leu Lys Phe Asp Met Lys Glu
            500                 505                 510

-continued

```
Cys Tyr Asp Arg Leu Ser Gln Pro Val Leu Met Lys Lys Leu Glu Glu
            515                 520                 525

Leu Phe Glu Asn Gln Asp Asn Lys Thr Leu Tyr Tyr Val Arg Tyr Tyr
        530                 535                 540

Ala Gln Leu Asp Ala Ser His Lys Leu Lys Lys Val Lys Thr Thr Ile
545                 550                 555                 560

Asp Thr Gln Tyr His Asn Leu Asn Ile Leu Ser Ser Arg His Leu
            565                 570                 575

Ser Asn Cys Lys Ser Leu Val Asp Lys Thr Lys Thr Ile Ala Leu Gln
            580                 585                 590

Lys Gly Asn Ile Leu Glu Val Cys Arg Ser Gln Ile Tyr Asp Val Val
        595                 600                 605

Gly Ser Val Lys Asp Ala Arg Gly Asn Leu His Leu Tyr Lys Arg Lys
        610                 615                 620

Arg Gly Val Phe Gln Gly Phe Ser Leu Leu Ser Ile Phe Cys Asp Ile
625                 630                 635                 640

Leu Tyr Ser Ala Met Val His Asp Cys Phe Gln Phe Leu Trp Lys Ser
            645                 650                 655

Lys Gln Asp Phe Leu Phe Val Arg Leu Val Asp Asp Phe Leu Leu Val
            660                 665                 670

Thr Pro Asp Ser Asn Ile Tyr Asp Gln Val His Asn Ile Leu Ser Gly
            675                 680                 685

Lys Ile Leu Glu Ser Tyr Gly Ala Phe Val Asn Lys Asp Lys Thr Val
        690                 695                 700

Val Val Asn Gln Thr Thr Thr Lys Pro Ser Ile Asp Phe Val Gly Leu
705                 710                 715                 720

Glu Val Asn Thr Thr Asp Leu Ser Ile Lys Arg Asn Ser Gly Leu Ile
            725                 730                 735

Ser Leu Val Thr Thr Asn Phe Arg Thr Phe Lys Thr Leu Val Lys Tyr
            740                 745                 750

Leu Lys Thr Phe Tyr Gln Leu Asn Leu Glu Gly Phe Leu Leu Asp Cys
        755                 760                 765

Ser Phe Gly Val Leu Glu Asn Val Leu Glu Asn Met Gly Ser Leu Leu
770                 775                 780

Arg Leu Val Leu Arg Glu Phe Lys Thr Lys Phe Thr Ser Ile Val Lys
785                 790                 795                 800

Tyr Asp Thr Phe His Cys Tyr Lys Phe Ile Lys Phe Leu Tyr Asp Ile
            805                 810                 815

Ser Asn Tyr Thr Ile Val Lys Tyr Val Glu Thr Asn Ser Asp Trp Asp
            820                 825                 830

Gly Ala Pro Glu Leu Leu Asn Cys Ile Lys Gln Ile Ile Val Lys Glu
        835                 840                 845

Phe Ser Ser Phe Glu Ser Tyr Leu Glu Ile Val Glu Trp Val Gln Thr
        850                 855                 860

Leu Asn Ile
865

<210> SEQ ID NO 5
<211> LENGTH: 10640
<212> TYPE: DNA
<213> ORGANISM: Plasmodium falciparum
<220> FEATURE:
<221> NAME/KEY: CDS
<222> LOCATION: (834)..(7385)
<223> OTHER INFORMATION: TERT gene
<220> FEATURE:
```

-continued

```
<221> NAME/KEY: unsure
<222> LOCATION: (1821)..(1837)
<223> OTHER INFORMATION: m at position 1821 = a or c; w at position 1837
      = a or t.  Xaa (amino acid) at position 330 = Leu or Ile; Xaa at
      position 335 = Asp or Gly.

<400> SEQUENCE: 5
```

| | | |
|---|---|---|
| gtgtgttatc aaatatctga accgaacaaa taataagtaa gaaggataag aataaattac | 60 |
| atttaataaa tgaaataata atagatacat cattttttaa agagaattat gattttcaat | 120 |
| attttttaga aaatgtttta ttattagaag atttagtttt aaaaaagttg gataataaat | 180 |
| taaatgatga ggattttata tttaaagaaa ataaaaaagt atctataaat aattggaaag | 240 |
| aatgttatag tcatattaag aaaaaattaa atatcaaagg tatggatgaa aaagtaaga | 300 |
| tatataataa ttctatttta ttatttaatt ctactaaatt ttcctatgat gatataaatt | 360 |
| gttgtgattc tttttatggt ttacaagtat gggatatatt atttaattat gtatcattcg | 420 |
| attttttaaa ttatttattg tctaatacac ttatatttat atctgactac tttttttatca | 480 |
| atacaaataa taattttaaa acatatgtaa agtcatctta cttttattaaa attgcagaaa | 540 |
| tacaattaaa ttatcaagat gctcaaaata tagaaagaaa tattttttca aaaaaaaaaa | 600 |
| atttatatta taaaaataca aaactagtaa aattaacata tcaaaaaaaa agcatcaagg | 660 |
| atagtacaac accaaattta accatccaga aaaaagctag ataggaaag gaaaaaaaat | 720 |
| tcagtaaaaa tataagtacg aatgaacata tagatataaa tataaataat tatatatata | 780 |
| atacattaaa tcaaaacaat gaagtcaatc aatataatgt taatcatctc aat atg | 836 |
| | Met |
| | 1 |

| gat aaa aat att acc tac aaa gaa aag gag tcg cag aat tat acc atc | 884 |
|---|---|
| Asp Lys Asn Ile Thr Tyr Lys Glu Lys Glu Ser Gln Asn Tyr Thr Ile |
|         5               10             15 |

| aat aat aat tta tta aat gat caa ctt tta tat tat aat aaa aca tat | 932 |
|---|---|
| Asn Asn Asn Leu Leu Asn Asp Gln Leu Leu Tyr Tyr Asn Lys Thr Tyr |
|         20             25            30 |

| cag aat aat gta aat aca cat att tat tca aat gat aat aaa acg cct | 980 |
|---|---|
| Gln Asn Asn Val Asn Thr His Ile Tyr Ser Asn Asp Asn Lys Thr Pro |
| 35              40               45 |

| att att gct aac cag tgt ata gat ata cat aac cgt gta agt gat ccg | 1028 |
|---|---|
| Ile Ile Ala Asn Gln Cys Ile Asp Ile His Asn Arg Val Ser Asp Pro |
| 50              55             60         65 |

| aca agg aaa aat ata ttt tat cat agt ata aac agc ctt tcg tat gaa | 1076 |
|---|---|
| Thr Arg Lys Asn Ile Phe Tyr His Ser Ile Asn Ser Leu Ser Tyr Glu |
|           70             75            80 |

| gca agt ttg aat att ttt cat tat aat aat ctg aca caa cat aca aca | 1124 |
|---|---|
| Ala Ser Leu Asn Ile Phe His Tyr Asn Asn Leu Thr Gln His Thr Thr |
|           85             90            95 |

| tat ata gat aca cca aat aaa agt caa aca tgt ata aat agt cct atg | 1172 |
|---|---|
| Tyr Ile Asp Thr Pro Asn Lys Ser Gln Thr Cys Ile Asn Ser Pro Met |
| 100             105             110 |

| caa cat gaa ata gat gaa cat tca aat aat gaa ttg aaa aat caa aaa | 1220 |
|---|---|
| Gln His Glu Ile Asp Glu His Ser Asn Asn Glu Leu Lys Asn Gln Lys |
| 115             120             125 |

| tgt act caa tat gaa tat gta gat aac gta tgc aca acg aat aaa aat | 1268 |
|---|---|
| Cys Thr Gln Tyr Glu Tyr Val Asp Asn Val Cys Thr Thr Asn Lys Asn |
| 130             135             140         145 |

| ata tca aac gat aat ata agt gat aaa tgt att act act aaa aat ata | 1316 |
|---|---|
| Ile Ser Asn Asp Asn Ile Ser Asp Lys Cys Ile Thr Thr Lys Asn Ile |
|              150             155             160 |

| cct cta aaa tat cat att aat aaa aaa tat aaa tac tta tta aaa aaa | 1364 |

```
                 Pro Leu Lys Tyr His Ile Asn Lys Lys Tyr Lys Tyr Leu Leu Lys Lys
                                 165                 170                 175 aaa tac cat aca atg tac aca aat aat gat cat tca tat gga aag tat        1412
Lys Tyr His Thr Met Tyr Thr Asn Asn Asp His Ser Tyr Gly Lys Tyr
            180                 185                 190 ttg tat ctt gtt cag tgc agt ggt cga att tta aaa aat gac ttt ttt        1460
Leu Tyr Leu Val Gln Cys Ser Gly Arg Ile Leu Lys Asn Asp Phe Phe
195                 200                 205 aag gac atg aaa caa ata caa gaa gaa aga aag aaa tat aca tca aat        1508
Lys Asp Met Lys Gln Ile Gln Glu Glu Arg Lys Lys Tyr Thr Ser Asn
210                 215                 220                 225 att aag atc aac agt gaa tat acc aat aat ata ata att aac aac aac        1556
Ile Lys Ile Asn Ser Glu Tyr Thr Asn Asn Ile Ile Ile Asn Asn Asn
                230                 235                 240 aac aac aac aac aat aat aat aat aat aat aac aat aat gtg cat ggt        1604
Asn Asn Asn Asn Asn Asn Asn Asn Asn Asn Asn Asn Asn Val His Gly
            245                 250                 255 ttt gga cat ata aac aat ttg ttc tct tct aac gaa ttt cca tct tct        1652
Phe Gly His Ile Asn Asn Leu Phe Ser Ser Asn Glu Phe Pro Ser Ser
            260                 265                 270 aac att tca agc tgt act aat tac aca gaa aaa aat gat aaa tta aca        1700
Asn Ile Ser Ser Cys Thr Asn Tyr Thr Glu Lys Asn Asp Lys Leu Thr
275                 280                 285 cac ata agg gaa act tcc tta cta ata aca gaa aat tct tca aaa aaa        1748
His Ile Arg Glu Thr Ser Leu Leu Ile Thr Glu Asn Ser Ser Lys Lys
290                 295                 300                 305 gat aag ctg tta cca gaa ata gat ttc ttt tct gag gat aga aag gag        1796
Asp Lys Leu Leu Pro Glu Ile Asp Phe Phe Ser Glu Asp Arg Lys Glu
                310                 315                 320 aaa tca tca tcg gtt ggt tat gac mta aaa aaa aag aat gwt agt aat        1844
Lys Ser Ser Ser Val Gly Tyr Asp Xaa Lys Lys Lys Asn Xaa Ser Asn
            325                 330                 335 att aaa aga ttt cat aat aaa ata aac aga acg aaa gaa gaa aaa aaa        1892
Ile Lys Arg Phe His Asn Lys Ile Asn Arg Thr Lys Glu Glu Lys Lys
            340                 345                 350 aaa aaa tgg aat aaa ata ata atc aat aga aac aac att tta caa cac        1940
Lys Lys Trp Asn Lys Ile Ile Ile Asn Arg Asn Asn Ile Leu Gln His
355                 360                 365 aat aca act aat aaa tgt aaa acc ttt cta ttt aat aaa cac ata ata        1988
Asn Thr Thr Asn Lys Cys Lys Thr Phe Leu Phe Asn Lys His Ile Ile
370                 375                 380                 385 ttt gat aaa ata gaa aat aat aat att cct tta ttt att tat gat tta        2036
Phe Asp Lys Ile Glu Asn Asn Asn Ile Pro Leu Phe Ile Tyr Asp Leu
            390                 395                 400 tta aac tat ata ttt aaa tca gat caa aca tat ttt tat cat aat aat        2084
Leu Asn Tyr Ile Phe Lys Ser Asp Gln Thr Tyr Phe Tyr His Asn Asn
            405                 410                 415 ttt ata gat gaa tat aag cag aaa ata tgt aaa caa ata aaa tgt tca        2132
Phe Ile Asp Glu Tyr Lys Gln Lys Ile Cys Lys Gln Ile Lys Cys Ser
            420                 425                 430 acc aaa aaa aat gac ata tct cat ata att aca tcg agg aaa gaa aat        2180
Thr Lys Lys Asn Asp Ile Ser His Ile Ile Thr Ser Arg Lys Glu Asn
435                 440                 445 cat tta ttt cat gta caa aaa ctt gaa aat aat tat aaa cat cca aat        2228
His Leu Phe His Val Gln Lys Leu Glu Asn Asn Tyr Lys His Pro Asn
450                 455                 460                 465 ata aat aaa cag cta aga aag acg aaa atc ttg aaa tat gta tat aat        2276
Ile Asn Lys Gln Leu Arg Lys Thr Lys Ile Leu Lys Tyr Val Tyr Asn
            470                 475                 480
```

```
tat ttt aag gaa ttt att aat aat gta att aat aca aaa ttt ggt aaa      2324
Tyr Phe Lys Glu Phe Ile Asn Asn Val Ile Asn Thr Lys Phe Gly Lys
            485                 490                 495 ata tat agg aaa ttt ttt cct cga aaa cat ata tta aat aag ata cat      2372
Ile Tyr Arg Lys Phe Phe Pro Arg Lys His Ile Leu Asn Lys Ile His
        500                 505                 510 aaa ata ttt aaa att ata aga tta caa ata ata aaa aaa tat cgt att      2420
Lys Ile Phe Lys Ile Ile Arg Leu Gln Ile Ile Lys Lys Tyr Arg Ile
    515                 520                 525 ata aat ata cga atg aat cga aaa ttt att aaa caa aaa gta tat gat      2468
Ile Asn Ile Arg Met Asn Arg Lys Phe Ile Lys Gln Lys Val Tyr Asp
530                 535                 540                 545 aca ttt ttt aaa aat tat gat ttc tta tca ttt tca ttt aaa acg tat      2516
Thr Phe Phe Lys Asn Tyr Asp Phe Leu Ser Phe Ser Phe Lys Thr Tyr
                550                 555                 560 aag att att aat ttt atg gta tat ata acc aaa aaa tgt ata cct atc      2564
Lys Ile Ile Asn Phe Met Val Tyr Ile Thr Lys Lys Cys Ile Pro Ile
            565                 570                 575 aaa tta tta ggt agt aag cat aat ttc aaa ata ttt tta aaa aat gta      2612
Lys Leu Leu Gly Ser Lys His Asn Phe Lys Ile Phe Leu Lys Asn Val
        580                 585                 590 aaa aaa ttt ttg tta ttt aat tat aaa gaa agt ttt tcg tta aat caa      2660
Lys Lys Phe Leu Leu Phe Asn Tyr Lys Glu Ser Phe Ser Leu Asn Gln
    595                 600                 605 gta atg aaa aat att aag gta aaa aat ata ttt caa aaa aaa ata agt      2708
Val Met Lys Asn Ile Lys Val Lys Asn Ile Phe Gln Lys Lys Ile Ser
610                 615                 620                 625 aaa tat aat ata aaa aat aga att tta tta aag aat ata ttt gat aac      2756
Lys Tyr Asn Ile Lys Asn Arg Ile Leu Leu Lys Asn Ile Phe Asp Asn
                630                 635                 640 aac tat gaa aac aaa att tta cat aga aat aat aag gaa atc ata aca      2804
Asn Tyr Glu Asn Lys Ile Leu His Arg Asn Asn Lys Glu Ile Ile Thr
            645                 650                 655 aat ata aat gat aac ata aaa ata tat aat aaa aaa aat gat aat tta      2852
Asn Ile Asn Asp Asn Ile Lys Ile Tyr Asn Lys Lys Asn Asp Asn Leu
        660                 665                 670 aat aat tca ttt aaa ata aaa aca acg tta ttc aat aaa ttg agg aga      2900
Asn Asn Ser Phe Lys Ile Lys Thr Thr Leu Phe Asn Lys Leu Arg Arg
    675                 680                 685 aaa tat ttc aat aaa att aaa aaa att aat ata gct ata caa aaa aga      2948
Lys Tyr Phe Asn Lys Ile Lys Lys Ile Asn Ile Ala Ile Gln Lys Arg
690                 695                 700                 705 cat ctt atg aat aga tta ata tat ttc ctt ttt aat tat ttt att atg      2996
His Leu Met Asn Arg Leu Ile Tyr Phe Leu Phe Asn Tyr Phe Ile Met
                710                 715                 720 cca cta att aga aga ttt ttt ttt cta acc aaa tct gag caa acc tta      3044
Pro Leu Ile Arg Arg Phe Phe Phe Leu Thr Lys Ser Glu Gln Thr Leu
            725                 730                 735 cat aaa aca att ttc ttt gat aga aaa att tgg aat cat ttt acg aaa      3092
His Lys Thr Ile Phe Phe Asp Arg Lys Ile Trp Asn His Phe Thr Lys
        740                 745                 750 att tcg aac ttt tgt ctt tac cat caa att ttt agg aat aaa aag tta      3140
Ile Ser Asn Phe Cys Leu Tyr His Gln Ile Phe Arg Asn Lys Lys Leu
    755                 760                 765 aaa aaa aga aat gaa ccc aaa atg gat tat gta caa aat atg ttc aat      3188
Lys Lys Arg Asn Glu Pro Lys Met Asp Tyr Val Gln Asn Met Phe Asn
770                 775                 780                 785 gtg aag aaa aaa ggt gaa aaa ata aaa aca aat aaa tat ata ttt att      3236
Val Lys Lys Lys Gly Glu Lys Ile Lys Thr Asn Lys Tyr Ile Phe Ile
                790                 795                 800
```

```
aag aaa atg aaa aaa aag agc act aat aaa tgt att aat aat aaa ttt     3284
Lys Lys Met Lys Lys Lys Ser Thr Asn Lys Cys Ile Asn Asn Lys Phe
            805                 810                 815 tcc aaa aaa tgt atc cct aaa aaa aaa aaa aaa aat tta tat aac atc     3332
Ser Lys Lys Cys Ile Pro Lys Lys Lys Lys Lys Asn Leu Tyr Asn Ile
            820                 825                 830 aca cgt cat aat aat ata ttt att aaa aag gat atg gaa aaa aaa tca     3380
Thr Arg His Asn Asn Ile Phe Ile Lys Lys Asp Met Glu Lys Lys Ser
835                 840                 845 aaa act aac aat tta att aat aaa agt ata gat aat tta tac aaa tta     3428
Lys Thr Asn Asn Leu Ile Asn Lys Ser Ile Asp Asn Leu Tyr Lys Leu
850                 855                 860                 865 aag gaa att aac aaa aaa agt gtt aga cca tat att aaa aaa ttt tac     3476
Lys Glu Ile Asn Lys Lys Ser Val Arg Pro Tyr Ile Lys Lys Phe Tyr
            870                 875                 880 tat aaa ata aaa aag aaa tat ttt gct cta aaa aaa atg tat att cat     3524
Tyr Lys Ile Lys Lys Lys Tyr Phe Ala Leu Lys Lys Met Tyr Ile His
            885                 890                 895 atg aga atg gca aaa gaa gaa aaa agt aac ata aaa tta gaa aga gca     3572
Met Arg Met Ala Lys Glu Glu Lys Ser Asn Ile Lys Leu Glu Arg Ala
            900                 905                 910 ttc aaa cat ttt ttt att ttt gct caa gaa aaa gaa cac ata ttg aaa     3620
Phe Lys His Phe Phe Ile Phe Ala Gln Glu Lys Glu His Ile Leu Lys
915                 920                 925 tat ttt agt tcc cat ttt ttt caa aat aga aag ata aat tat ggt aaa     3668
Tyr Phe Ser Ser His Phe Phe Gln Asn Arg Lys Ile Asn Tyr Gly Lys
930                 935                 940                 945 cga ttt aat aaa cta ata cat cga ata aaa aat ata ata ata aag caa     3716
Arg Phe Asn Lys Leu Ile His Arg Ile Lys Asn Ile Ile Ile Lys Gln
            950                 955                 960 aac agt gga att gtt aaa aat aag gat aag aca ttt tta cat tta atc     3764
Asn Ser Gly Ile Val Lys Asn Lys Asp Lys Thr Phe Leu His Leu Ile
            965                 970                 975 aaa aat aaa agt aac aaa aat aac aat aac aag aag aag aac aaa aat     3812
Lys Asn Lys Ser Asn Lys Asn Asn Asn Lys Lys Lys Asn Lys Asn
            980                 985                 990 aat tat aac aat aat aat att aat aat aac aat aat aat aat aac aat     3860
Asn Tyr Asn Asn Asn Asn Ile Asn Asn Asn Asn Asn Asn Asn Asn Asn
995                 1000                1005 aat aat att aat aat aat aat aac aac aaa tgt aaa cta tca aat tcc     3908
Asn Asn Ile Asn Asn Asn Asn Asn Asn Lys Cys Lys Leu Ser Asn Ser
1010                1015                1020                1025 aaa agg tat aat ata aga aat aat aat aat aat aaa aag gct aaa aat     3956
Lys Arg Tyr Asn Ile Arg Asn Asn Asn Asn Asn Lys Lys Ala Lys Asn
                1030                1035                1040 aat gag aag aac aat att gat gat tcc aat tta gaa aaa aaa aaa aaa     4004
Asn Glu Lys Asn Asn Ile Asp Asp Ser Asn Leu Glu Lys Lys Lys Lys
                1045                1050                1055 aaa ata tac ata tat aaa ata aaa aat att ata gag aaa aga aat ttt     4052
Lys Ile Tyr Ile Tyr Lys Ile Lys Asn Ile Ile Glu Lys Arg Asn Phe
                1060                1065                1070 atg tta aaa tta aat tca atc aat cat ttt ata tct aaa aag tta aga     4100
Met Leu Lys Leu Asn Ser Ile Asn His Phe Ile Ser Lys Lys Leu Arg
    1075                1080                1085 att aat tgg ata cca aaa aaa aaa gga tta aga cct tta att aat ttg     4148
Ile Asn Trp Ile Pro Lys Lys Lys Gly Leu Arg Pro Leu Ile Asn Leu
1090                1095                1100                1105 tct act tta aat gtg cca gaa att gtc aag caa cga att ttt gaa att     4196
Ser Thr Leu Asn Val Pro Glu Ile Val Lys Gln Arg Ile Phe Glu Ile
```

-continued

|  | 1110 |  |  |  | 1115 |  |  |  | 1120 |  |  |  |  |
|---|---|---|---|---|---|---|---|---|---|---|---|---|---|
| ttg | aaa | agt | aaa | aaa | agc | agt | gaa | ttt | tat | ttc | cat | aat | att | ttg | aat | 4244 |
| Leu | Lys | Ser | Lys | Lys | Ser | Ser | Glu | Phe | Tyr | Phe | His | Asn | Ile | Leu | Asn |  |
|  |  | 1125 |  |  |  |  | 1130 |  |  |  |  | 1135 |  |  |  |  | aat tta gaa aga gaa aag aaa gat aaa aat ata aag aaa agg aaa aaa    4292
Asn Leu Glu Arg Glu Lys Lys Asp Lys Asn Ile Lys Lys Arg Lys Lys
        1140                1145                1150 tat aat aaa aaa aat ttt aac cct gta tca tta aac aat ata tgt aat    4340
Tyr Asn Lys Lys Asn Phe Asn Pro Val Ser Leu Asn Asn Ile Cys Asn
    1155                1160                1165 ttt tcc ctt aaa tgt tta ggt aat atg aga cat aat aat aat tcc tta    4388
Phe Ser Leu Lys Cys Leu Gly Asn Met Arg His Asn Asn Asn Ser Leu
1170                1175                1180                1185 ttt aaa aat aca tta acg aaa aca gga gaa ata gaa tta aaa tta aaa    4436
Phe Lys Asn Thr Leu Thr Lys Thr Gly Glu Ile Glu Leu Lys Leu Lys
        1190                1195                1200 aaa tgg tta cat tat tta aaa aat tgg ttt tat aaa aaa aaa aga atg    4484
Lys Trp Leu His Tyr Leu Lys Asn Trp Phe Tyr Lys Lys Lys Arg Met
            1205                1210                1215 aaa aag tat att aaa aat aaa tta aaa aac aat aaa aag ata tat gca    4532
Lys Lys Tyr Ile Lys Asn Lys Leu Lys Asn Asn Lys Lys Ile Tyr Ala
        1220                1225                1230 tat ata tgt att gga gat ttc tca aac tgt tat gaa cat ata aat cat    4580
Tyr Ile Cys Ile Gly Asp Phe Ser Asn Cys Tyr Glu His Ile Asn His
    1235                1240                1245 aat tat tta ttc aag att tta aaa aat ttc ttt gat aat ata aat aat    4628
Asn Tyr Leu Phe Lys Ile Leu Lys Asn Phe Phe Asp Asn Ile Asn Asn
1250                1255                1260                1265 ttt gaa ttt att tat tta ttt aaa aga tct ttt aga tta tat aat aaa    4676
Phe Glu Phe Ile Tyr Leu Phe Lys Arg Ser Phe Arg Leu Tyr Asn Lys
        1270                1275                1280 aat tta aat aat tcc ttt tta tcc tat tac cca gtt aat gta aaa tct    4724
Asn Leu Asn Asn Ser Phe Leu Ser Tyr Tyr Pro Val Asn Val Lys Ser
    1285                1290                1295 ttt ggt tta cat tat ata aga aac tta cga gag ctt ata ata aag tca    4772
Phe Gly Leu His Tyr Ile Arg Asn Leu Arg Glu Leu Ile Ile Lys Ser
        1300                1305                1310 cat ctg aat gat aat cat cac ttt tta tta aat caa atg ttt aaa acc    4820
His Leu Asn Asp Asn His His Phe Leu Leu Asn Gln Met Phe Lys Thr
1315                1320                1325 aaa tca aaa tcg gat tta tac att ttt gcc gat tca tat aaa agt ctg    4868
Lys Ser Lys Ser Asp Leu Tyr Ile Phe Ala Asp Ser Tyr Lys Ser Leu
1330                1335                1340                1345 caa gtg gac aaa agg gat att ttc atg act ata ata act gtt att aga    4916
Gln Val Asp Lys Arg Asp Ile Phe Met Thr Ile Ile Thr Val Ile Arg
        1350                1355                1360 tat tac tac ctc aat ata tat ttt agt ata aaa gaa ttt aaa ctt aat    4964
Tyr Tyr Tyr Leu Asn Ile Tyr Phe Ser Ile Lys Glu Phe Lys Leu Asn
    1365                1370                1375 agg aaa aat att ttc tat ttt caa ata ttt cag gaa aat caa atg aag    5012
Arg Lys Asn Ile Phe Tyr Phe Gln Ile Phe Gln Glu Asn Gln Met Lys
        1380                1385                1390 ggt gtt tat ttg agt gtc cgt gat aag aaa agg gtt gaa aat att aaa    5060
Gly Val Tyr Leu Ser Val Arg Asp Lys Lys Arg Val Glu Asn Ile Lys
    1395                1400                1405 aaa tgg tat tta aac agc atg aaa aaa ata aat cac gac gaa ata cta    5108
Lys Trp Tyr Leu Asn Ser Met Lys Lys Ile Asn His Asp Glu Ile Leu
1410                1415                1420                1425 gaa agt tta aaa aat tca tcc ata aat ata aat aat aaa aac ttt atg    5156

```
Glu Ser Leu Lys Asn Ser Ser Ile Asn Ile Asn Asn Lys Asn Phe Met
            1430                1435                1440 ata tgt acc aat cat gag caa gat aca gaa gaa aaa gga aat aca caa        5204
Ile Cys Thr Asn His Glu Gln Asp Thr Glu Glu Lys Gly Asn Thr Gln
        1445                1450                1455 aat aag gag aag cat gat att tat att gga cca ata tat aat aat tcg        5252
Asn Lys Glu Lys His Asp Ile Tyr Ile Gly Pro Ile Tyr Asn Asn Ser
    1460                1465                1470 ttc gac agt aca aca aca aca cat agt agt aat aat tat aaa ggg aat        5300
Phe Asp Ser Thr Thr Thr Thr His Ser Ser Asn Asn Tyr Lys Gly Asn
1475                1480                1485 aat atc cat gtg agt ggg gat tat aag aat gat ggg cta tta cat aaa        5348
Asn Ile His Val Ser Gly Asp Tyr Lys Asn Asp Gly Leu Leu His Lys
1490                1495                1500                1505 ggt aat aat agt atg aat gaa tgt tat gtg aag gac ata aaa tgt aat        5396
Gly Asn Asn Ser Met Asn Glu Cys Tyr Val Lys Asp Ile Lys Cys Asn
        1510                1515                1520 aat aat aat aat aat aat aat aat aac aac aac aat aat att aat aat        5444
Asn Asn Asn Asn Asn Asn Asn Asn Asn Asn Asn Asn Asn Ile Asn Asn
    1525                1530                1535 agt tat aat aaa tta aat tgt gtt acg aat aat agc aaa aat gac ata        5492
Ser Tyr Asn Lys Leu Asn Cys Val Thr Asn Asn Ser Lys Asn Asp Ile
        1540                1545                1550 att aaa tac cac aaa act atc gac aca gat aat agt aaa aat cat aca        5540
Ile Lys Tyr His Lys Thr Ile Asp Thr Asp Asn Ser Lys Asn His Thr
1555                1560                1565 tac ttt aaa aat aaa ttc cta aat ttt ttg gat aaa aaa att att agt        5588
Tyr Phe Lys Asn Lys Phe Leu Asn Phe Leu Asp Lys Lys Ile Ile Ser
1570                1575                1580                1585 aat ata tat ggc tta cca caa ggt ttt agc tta tct aat ata ttg tgc        5636
Asn Ile Tyr Gly Leu Pro Gln Gly Phe Ser Leu Ser Asn Ile Leu Cys
        1590                1595                1600 tcc cta tat tat gca tat tta gat aaa aat gaa gaa ttt caa aat tta        5684
Ser Leu Tyr Tyr Ala Tyr Leu Asp Lys Asn Glu Glu Phe Gln Asn Leu
        1605                1610                1615 tta tat tca gaa aaa caa atc aat aat aaa tat ttc tta gca aat gga        5732
Leu Tyr Ser Glu Lys Gln Ile Asn Asn Lys Tyr Phe Leu Ala Asn Gly
    1620                1625                1630 act tgt aat tat ttc aat tta aat tca ctc ata ctc cga ttt att gat        5780
Thr Cys Asn Tyr Phe Asn Leu Asn Ser Leu Ile Leu Arg Phe Ile Asp
1635                1640                1645 gac ttt tta ttt ata act ctt aat aaa aaa aat att aaa ata ttt aaa        5828
Asp Phe Leu Phe Ile Thr Leu Asn Lys Lys Asn Ile Lys Ile Phe Lys
1650                1655                1660                1665 aac tta cta tta aaa aaa aaa ata tgg gga agt aat att aat tca tcc        5876
Asn Leu Leu Leu Lys Lys Lys Ile Trp Gly Ser Asn Ile Asn Ser Ser
        1670                1675                1680 aaa acc aaa atc ttc aaa ata cca ctt ata tat aaa aat gat tta cta        5924
Lys Thr Lys Ile Phe Lys Ile Pro Leu Ile Tyr Lys Asn Asp Leu Leu
        1685                1690                1695 ata tat aat ttt caa aat aaa tac caa aaa aaa aaa tac aaa ata aaa        5972
Ile Tyr Asn Phe Gln Asn Lys Tyr Gln Lys Lys Lys Tyr Lys Ile Lys
    1700                1705                1710 aat aaa aaa aaa ata caa agt gtg agg aac aaa cgg ata cat aat cag        6020
Asn Lys Lys Lys Ile Gln Ser Val Arg Asn Lys Arg Ile His Asn Gln
1715                1720                1725 cta gtc aat gct aat aaa aaa aaa cac aca tct gta caa aaa gat aaa        6068
Leu Val Asn Ala Asn Lys Lys Lys His Thr Ser Val Gln Lys Asp Lys
1730                1735                1740                1745
```

```
ata aat aaa tat ata aat ctc ata cat cca aca ata caa aaa aat gat    6116
Ile Asn Lys Tyr Ile Asn Leu Ile His Pro Thr Ile Gln Lys Asn Asp
        1750                1755                1760 tct gtc ttg tct tct aat tct att atg aat ttt gaa agg ata tat att    6164
Ser Val Leu Ser Ser Asn Ser Ile Met Asn Phe Glu Arg Ile Tyr Ile
        1765                1770                1775 aaa gaa agt cat aaa agt aac agt tca ata cgt acg gat att ccg aat    6212
Lys Glu Ser His Lys Ser Asn Ser Ser Ile Arg Thr Asp Ile Pro Asn
        1780                1785                1790 agt gtt gta aat gac gat ata gaa tat aat caa aaa agt gat aat aat    6260
Ser Val Val Asn Asp Asp Ile Glu Tyr Asn Gln Lys Ser Asp Asn Asn
    1795                1800                1805 tct tac agt act aat aat tta tac aac aat ata aat atg act caa aat    6308
Ser Tyr Ser Thr Asn Asn Leu Tyr Asn Asn Ile Asn Met Thr Gln Asn
1810                1815                1820                1825 ggt gat aat aat aat gtt aat att ttt aaa cat gta caa aat gat tct    6356
Gly Asp Asn Asn Asn Val Asn Ile Phe Lys His Val Gln Asn Asp Ser
        1830                1835                1840 ttt caa tgt ttt aat agt aac aac tta tat att gaa aag gat ata aaa    6404
Phe Gln Cys Phe Asn Ser Asn Asn Leu Tyr Ile Glu Lys Asp Ile Lys
        1845                1850                1855 gaa aat aat att tca caa atc aac aga aag tta tgt tct aaa aga aat    6452
Glu Asn Asn Ile Ser Gln Ile Asn Arg Lys Leu Cys Ser Lys Arg Asn
        1860                1865                1870 ttt aca aaa aaa agt aga aaa ata aat act ttg aca tat tta caa att    6500
Phe Thr Lys Lys Ser Arg Lys Ile Asn Thr Leu Thr Tyr Leu Gln Ile
        1875                1880                1885 gat aaa gtt ata aaa atc cta aaa tgt aag aag aaa tat ata aaa cat    6548
Asp Lys Val Ile Lys Ile Leu Lys Cys Lys Lys Lys Tyr Ile Lys His
1890                1895                1900                1905 ata aaa aag atg aag tat atg aat aat ttt caa aat ttt aaa aaa tta    6596
Ile Lys Lys Met Lys Tyr Met Asn Asn Phe Gln Asn Phe Lys Lys Leu
        1910                1915                1920 aaa aaa tta caa aaa ttt cat aat gcc tct ttt gaa tta aaa att aat    6644
Lys Lys Leu Gln Lys Phe His Asn Ala Ser Phe Glu Leu Lys Ile Asn
        1925                1930                1935 aaa att aat aaa aat att aga cga ttg aat aaa tta aaa aaa cgt aaa    6692
Lys Ile Asn Lys Asn Ile Arg Arg Leu Asn Lys Leu Lys Lys Arg Lys
        1940                1945                1950 aat cat tct ata aac att act cct gtt act tct ata gaa tgg tta aat    6740
Asn His Ser Ile Asn Ile Thr Pro Val Thr Ser Ile Glu Trp Leu Asn
        1955                1960                1965 aat tca tac aca ttt gat ttt ata aat aat tct ata caa agc act tca    6788
Asn Ser Tyr Thr Phe Asp Phe Ile Asn Asn Ser Ile Gln Ser Thr Ser
1970                1975                1980                1985 tat cca tgg aaa aat aaa tgt gat gct act att aga aat cat tta cat    6836
Tyr Pro Trp Lys Asn Lys Cys Asp Ala Thr Ile Arg Asn His Leu His
        1990                1995                2000 cta cat aat gtt att ata gat aaa aat aat aaa act tat ttt atg aaa    6884
Leu His Asn Val Ile Ile Asp Lys Asn Asn Lys Thr Tyr Phe Met Lys
        2005                2010                2015 aac cta gtt gaa aat aga att gta cga aat att ata tcc aaa caa aaa    6932
Asn Leu Val Glu Asn Arg Ile Val Arg Asn Ile Ile Ser Lys Gln Lys
        2020                2025                2030 aaa tgt caa tcc tta tat aag aat aag caa aat gta tat ttc tgt tat    6980
Lys Cys Gln Ser Leu Tyr Lys Asn Lys Gln Asn Val Tyr Phe Cys Tyr
        2035                2040                2045 aaa aat aat ttt agc tta tta aaa tca tct ata tta aaa ttc atc tgt    7028
Lys Asn Asn Phe Ser Leu Leu Lys Ser Ser Ile Leu Lys Phe Ile Cys
2050                2055                2060                2065
```

```
tgt att aaa aca ctc aaa aaa atg ttt aat gca ttt aca aat tct aca    7076
Cys Ile Lys Thr Leu Lys Lys Met Phe Asn Ala Phe Thr Asn Ser Thr
        2070              2075                 2080 tat aac aca aaa ttt ata tta ttt ctc ata tcg tat atg aat aaa atg    7124
Tyr Asn Thr Lys Phe Ile Leu Phe Leu Ile Ser Tyr Met Asn Lys Met
            2085              2090                 2095 tta ata aaa aat aaa aaa ctc aaa ttt gtc aaa ttg ttt tta att caa    7172
Leu Ile Lys Asn Lys Lys Leu Lys Phe Val Lys Leu Phe Leu Ile Gln
        2100              2105                 2110 aca gca atc gaa gcc ttc cgt tat gcc aga att ttt aat cag cag gat    7220
Thr Ala Ile Glu Ala Phe Arg Tyr Ala Arg Ile Phe Asn Gln Gln Asp
            2115              2120                 2125 tcc ttt tat ccg tgt ctc caa cat ttc agg aaa atc aaa aaa aga tta    7268
Ser Phe Tyr Pro Cys Leu Gln His Phe Arg Lys Ile Lys Lys Arg Leu
2130                 2135              2140                 2145 att aac aaa tac aaa att gga cat aac aaa aat tta ttg cga gaa ttt    7316
Ile Asn Lys Tyr Lys Ile Gly His Asn Lys Asn Leu Leu Arg Glu Phe
                2150              2155                 2160 ttt ttc ctg ttt aat ttt atc aag aaa gag ttg tat aat tca tgg cct    7364
Phe Phe Leu Phe Asn Phe Ile Lys Lys Glu Leu Tyr Asn Ser Trp Pro
            2165              2170                 2175 tac atg ttc aaa ata aaa aat taaaaaaaaa aaaaaaaaaa aaaaaatata       7415
Tyr Met Phe Lys Ile Lys Asn
        2180 tatatatata tatatataag taaaacgtt gtttatatta atatgtccaa              7475 cttataaagt tatataatta ttaattttgt tcatatttta cttaatatta atttttataca 7535 ttctattatt ttttttttt tttgcatttg tatttgtttt taaatatata ttgattttgg   7595 attgacatat ttttttttta ttttttcttt tttttttataa tcttggcttg gtgtccaaac 7655 atagattgga tattttttc agagcctgca actttccacg tgaacctacc ctaatattta   7715 ccaatccttt tttattaata ttataaaggg tatgtgatat attcttgtaa taatttggct  7775 tgaaaccata ctgataagaa cttggttctc cagatttttt ataaagcaaa aatggatatg  7835 gttcgagaac tcttgaagct ctccatttga atggtctaat attactataa taatttttat  7895 atttctcttct tataattcca tgatatttt taaatgaaat tttattatgc cttctacaaa  7955 aataaataac attagatggt atttctaata atcttctatt aaccatattc caatattttg  8015 gtgcaggcat tactttttta tgtggtaaat aatttcttga aacttcttca agagcctcac  8075 tatatatttt acatgtattg taatctttat caacaaatga tatagaattt atattatata  8135 atggaatggt acttcttagt tgtaataatg attcaacaca ttcctcaagt aatatattac  8195 tagattgatt cggactatat ccatatatac ctgctgagat atccggtaat attatagaag  8255 atatacataa ctcattcaat tgttttaaag cattagaaaa gcaatatctt aacttatttg  8315 atgaaatata tgaattaccc tgccatacat atggcattat taaaaatgct ataaatttca  8375 cttttttact aacattatgt ggtttactta atataatatc accaatttgt aatgttttg   8435 atccttcata taattcttta aatttttgtt ctccatttat ttctaaagat gattgtacat  8495 attcttcctt atgctcattc aatatatcaa ttcttctttt tattaaattt ttaattgata  8555 gaattatctc tttaactaat tcgggaccc ctttatttaa tataaacgaa ccaaaaccac   8615 tcataggtat gaaattagaa accataggta ttaacataca atctgcttct tcatctataa  8675 tatcattatg tattattta atattaccaa attcttctaa agtcatattt ttcatttcat   8735 attcatattt atccttaatt ttatttatat ctaatatttc catatcttct tctaataaac  8795
```

-continued

```
ctttattctc atcattctcc ttattattta aaaaaaacat atcatttatc tcacttttca    8855
tgttaggaaa tatttctttc attacacttc tattcttccc ttctaatata tcgagagatt    8915
tcgtataatc tatatgatat tttaatgctc tttcgtttat tgttttcaac ctcttggtta    8975
aataggaact accaaaataa cgtttcccca taaaaaaaaa tcttaacatt tttatatata    9035
cccataataa tatacaaata aataaatata tatatatata tatatatgta tcagtcaata    9095
ctacatgggg ttaattatag aaaaatatat taaaaatata tttatatatt attataaata    9155
ctatatatat attattttga tctaaaatga caggacatta tatataggta cattgtatct    9215
actaataata aacagaatta caatattttt ttatatatta tatcttagca tatattatta    9275
ttattcgctt ttgtaacctc gaaaatatgg ttaaaaaaaa aaaaaaattc atattatata    9335
tatatgtaag tagtatattt ttaatatgtt tattgattta tttttttttt tttttttttt    9395 ttttatatt tattcatttt tcttttgata tttatccaaa agaaatatac tatatatata    9455
tgtgtagtgc ttaatttatt atgtgcatga tatatacaaa gatggtatca ttttagatat    9515
tttattccaa aatgtatatg taaatatata atattatata tatataatat atttatatat    9575
atgtccataa aaaaaaaaaa aaaatacata catatatata tatatatata tatatataca    9635
tatatgtact actaaaatgt aaatacatat tatatgaaaa taaaattaat gtactaaaca    9695
tatgataaaa aaaaaaaaat taaattaata tgttcagtta tacaaaaaag ggttattata    9755
tagtatcaca gattcatta tacattagta atatatttat actataatat attgagaagt    9815
ttaccataat attaatatac ctatattata catataaaaa attttccacc catttatatt    9875
taaattactt ttaattatct aacattttcc tatatccatt taattcaaac acttttatta    9935
tatcttttac aaaattatta tctaagtctt ttactccatg ttttgaaaaa acaagcgata    9995
gatcaattga taaattatcc attcctcctt caatatcggt aatattatat tcagggttaa    10055
tgtctggatt atttttttaat aaatttctta ataaagcttc atctataaaa aataaaaaaa    10115
tatataaatt atatttaatc ccgtcagaat tgtataagaa catattatta aaattatttt    10175
tattatgtta tgttatattt ttttttttttt tttttatgct taccttcttt tttaaaatgt    10235
atactttcgt ctgtcttcct gttattatcc aagaattta caccaccaaa attttgatta    10295
cacataaatt ttaccttaat tgttacatta tcacttattt tgttcttaac aaatatcttt    10355
cttgtaatag ctggtaccat attttctata gatatgtatg aatgcttta taataataa    10415 aacaatatat aaaattaaga aaaaaaaaa aaaaaaaaa aaactaattt actatcaata    10475
cgatacaaag atactaaata ataaaaaaat atatataaat catatatata ttatttaat    10535 tataaatttt tatttttaatt cgaaaaaata tccatgtgaa ttattatatt tccagtgaaa    10595
ttatataaat aatatagaaa taaataaagt atgatactta gaaaa                    10640
```

<210> SEQ ID NO 6
<211> LENGTH: 2184
<212> TYPE: PRT
<213> ORGANISM: Plasmodium falciparum
<220> FEATURE:
<221> NAME/KEY: unsure
<222> LOCATION: (330)..(335)
<223> OTHER INFORMATION: Xaa at position 330 = Leu or Ile;
     Xaa at position 335 = Asp or Gly.

<400> SEQUENCE: 6

```
Met Asp Lys Asn Ile Thr Tyr Lys Glu Lys Glu Ser Gln Asn Tyr Thr
 1               5                  10                  15

Ile Asn Asn Asn Leu Leu Asn Asp Gln Leu Leu Tyr Tyr Asn Lys Thr
```

-continued

```
                20                  25                  30
Tyr Gln Asn Asn Val Asn Thr His Ile Tyr Ser Asn Asp Asn Lys Thr
            35                  40                  45
Pro Ile Ile Ala Asn Gln Cys Ile Asp Ile His Asn Arg Val Ser Asp
        50                  55                  60
Pro Thr Arg Lys Asn Ile Phe Tyr His Ser Ile Asn Ser Leu Ser Tyr
65                  70                  75                  80
Glu Ala Ser Leu Asn Ile Phe His Tyr Asn Asn Leu Thr Gln His Thr
                85                  90                  95
Thr Tyr Ile Asp Thr Pro Asn Lys Ser Gln Thr Cys Ile Asn Ser Pro
            100                 105                 110
Met Gln His Glu Ile Asp Glu His Ser Asn Asn Glu Leu Lys Asn Gln
        115                 120                 125
Lys Cys Thr Gln Tyr Glu Tyr Val Asp Asn Val Cys Thr Thr Asn Lys
    130                 135                 140
Asn Ile Ser Asn Asp Asn Ile Ser Asp Lys Cys Ile Thr Thr Lys Asn
145                 150                 155                 160
Ile Pro Leu Lys Tyr His Ile Asn Lys Lys Tyr Lys Tyr Leu Leu Lys
                165                 170                 175
Lys Lys Tyr His Thr Met Tyr Thr Asn Asn Asp His Ser Tyr Gly Lys
            180                 185                 190
Tyr Leu Tyr Leu Val Gln Cys Ser Gly Arg Ile Leu Lys Asn Asp Phe
        195                 200                 205
Phe Lys Asp Met Lys Gln Ile Gln Glu Glu Arg Lys Lys Tyr Thr Ser
    210                 215                 220
Asn Ile Lys Ile Asn Ser Glu Tyr Thr Asn Asn Ile Ile Ile Asn Asn
225                 230                 235                 240
Asn Asn Asn Asn Asn Asn Asn Asn Asn Asn Asn Asn Asn Asn Val His
                245                 250                 255
Gly Phe Gly His Ile Asn Asn Leu Phe Ser Ser Asn Glu Phe Pro Ser
            260                 265                 270
Ser Asn Ile Ser Ser Cys Thr Asn Tyr Thr Glu Lys Asn Asp Lys Leu
        275                 280                 285
Thr His Ile Arg Glu Thr Ser Leu Leu Ile Thr Glu Asn Ser Ser Lys
    290                 295                 300
Lys Asp Lys Leu Leu Pro Glu Ile Asp Phe Phe Ser Glu Asp Arg Lys
305                 310                 315                 320
Glu Lys Ser Ser Ser Val Gly Tyr Asp Xaa Lys Lys Asn Xaa Ser
                325                 330                 335
Asn Ile Lys Arg Phe His Asn Lys Ile Asn Arg Thr Lys Glu Glu Lys
            340                 345                 350
Lys Lys Lys Trp Asn Lys Ile Ile Ile Asn Arg Asn Asn Ile Leu Gln
        355                 360                 365
His Asn Thr Thr Asn Lys Cys Lys Thr Phe Leu Phe Asn Lys His Ile
    370                 375                 380
Ile Phe Asp Lys Ile Glu Asn Asn Asn Ile Pro Leu Phe Ile Tyr Asp
385                 390                 395                 400
Leu Leu Asn Tyr Ile Phe Lys Ser Asp Gln Thr Tyr Phe Tyr His Asn
                405                 410                 415
Asn Phe Ile Asp Glu Tyr Lys Gln Lys Ile Cys Lys Gln Ile Lys Cys
            420                 425                 430
Ser Thr Lys Lys Asn Asp Ile Ser His Ile Ile Thr Ser Arg Lys Glu
        435                 440                 445
```

-continued

```
Asn His Leu Phe His Val Gln Lys Leu Glu Asn Tyr Lys His Pro
450                     455                 460
Asn Ile Asn Lys Gln Leu Arg Lys Thr Lys Ile Leu Lys Tyr Val Tyr
465                 470                 475                 480
Asn Tyr Phe Lys Glu Phe Ile Asn Asn Val Ile Asn Thr Lys Phe Gly
                485                 490                 495
Lys Ile Tyr Arg Lys Phe Phe Pro Arg Lys His Ile Leu Asn Lys Ile
                500                 505                 510
His Lys Ile Phe Lys Ile Ile Arg Leu Gln Ile Ile Lys Lys Tyr Arg
            515                 520                 525
Ile Ile Asn Ile Arg Met Asn Arg Lys Phe Ile Lys Gln Lys Val Tyr
        530                 535                 540
Asp Thr Phe Phe Lys Asn Tyr Asp Phe Leu Ser Phe Ser Phe Lys Thr
545                 550                 555                 560
Tyr Lys Ile Ile Asn Phe Met Val Tyr Ile Thr Lys Lys Cys Ile Pro
                565                 570                 575
Ile Lys Leu Leu Gly Ser Lys His Asn Phe Lys Ile Phe Leu Lys Asn
            580                 585                 590
Val Lys Lys Phe Leu Leu Phe Asn Tyr Lys Glu Ser Phe Ser Leu Asn
        595                 600                 605
Gln Val Met Lys Asn Ile Lys Val Lys Asn Ile Phe Gln Lys Lys Ile
    610                 615                 620
Ser Lys Tyr Asn Ile Lys Asn Arg Ile Leu Leu Lys Asn Ile Phe Asp
625                 630                 635                 640
Asn Asn Tyr Glu Asn Lys Ile Leu His Arg Asn Asn Lys Glu Ile Ile
                645                 650                 655
Thr Asn Ile Asn Asp Asn Ile Lys Ile Tyr Asn Lys Lys Asn Asp Asn
            660                 665                 670
Leu Asn Asn Ser Phe Lys Ile Lys Thr Thr Leu Phe Asn Lys Leu Arg
        675                 680                 685
Arg Lys Tyr Phe Asn Lys Ile Lys Ile Asn Ile Ala Ile Gln Lys
    690                 695                 700
Arg His Leu Met Asn Arg Leu Ile Tyr Phe Leu Phe Asn Tyr Phe Ile
705                 710                 715                 720
Met Pro Leu Ile Arg Arg Phe Phe Leu Thr Lys Ser Glu Gln Thr
                725                 730                 735
Leu His Lys Thr Ile Phe Phe Asp Arg Lys Ile Trp Asn His Phe Thr
            740                 745                 750
Lys Ile Ser Asn Phe Cys Leu Tyr His Gln Ile Phe Arg Asn Lys Lys
        755                 760                 765
Leu Lys Lys Arg Asn Glu Pro Lys Met Asp Tyr Val Gln Asn Met Phe
    770                 775                 780
Asn Val Lys Lys Lys Gly Glu Lys Ile Lys Thr Asn Lys Tyr Ile Phe
785                 790                 795                 800
Ile Lys Lys Met Lys Lys Lys Ser Thr Asn Lys Cys Ile Asn Asn Lys
                805                 810                 815
Phe Ser Lys Lys Cys Ile Pro Lys Lys Lys Lys Asn Leu Tyr Asn
            820                 825                 830
Ile Thr Arg His Asn Asn Ile Phe Ile Lys Lys Asp Met Glu Lys Lys
        835                 840                 845
Ser Lys Thr Asn Asn Leu Ile Asn Lys Ser Ile Asp Asn Leu Tyr Lys
    850                 855                 860
```

-continued

```
Leu Lys Glu Ile Asn Lys Lys Ser Val Arg Pro Tyr Ile Lys Lys Phe
865                 870                 875                 880

Tyr Tyr Lys Ile Lys Lys Tyr Phe Ala Leu Lys Lys Met Tyr Ile
            885                 890                 895

His Met Arg Met Ala Lys Glu Glu Lys Ser Asn Ile Lys Leu Glu Arg
            900                 905                 910

Ala Phe Lys His Phe Phe Ile Phe Ala Gln Lys Glu His Ile Leu
            915                 920                 925

Lys Tyr Phe Ser Ser His Phe Phe Gln Asn Arg Lys Ile Asn Tyr Gly
            930                 935                 940

Lys Arg Phe Asn Lys Leu Ile His Arg Ile Lys Asn Ile Ile Lys
945                 950                 955                 960

Gln Asn Ser Gly Ile Val Lys Asn Lys Asp Lys Thr Phe Leu His Leu
            965                 970                 975

Ile Lys Asn Lys Ser Asn Lys Asn Asn Asn Lys Lys Lys Asn Lys
            980                 985                 990

Asn Asn Tyr Asn Asn Asn Ile Asn Asn Asn Asn Asn Asn Asn
            995                 1000                1005

Asn Asn Asn Ile Asn Asn Asn Asn Asn Lys Cys Lys Leu Ser Asn
    1010                1015                1020

Ser Lys Arg Tyr Asn Ile Arg Asn Asn Asn Asn Lys Lys Ala Lys
1025                1030                1035                1040

Asn Asn Glu Lys Asn Asn Ile Asp Asp Ser Asn Leu Glu Lys Lys Lys
            1045                1050                1055

Lys Lys Ile Tyr Ile Tyr Lys Ile Lys Asn Ile Ile Glu Lys Arg Asn
            1060                1065                1070

Phe Met Leu Lys Leu Asn Ser Ile Asn His Phe Ile Ser Lys Lys Leu
            1075                1080                1085

Arg Ile Asn Trp Ile Pro Lys Lys Gly Leu Arg Pro Leu Ile Asn
            1090                1095                1100

Leu Ser Thr Leu Asn Val Pro Glu Ile Val Lys Gln Arg Ile Phe Glu
1105                1110                1115                1120

Ile Leu Lys Ser Lys Lys Ser Ser Glu Phe Tyr Phe His Asn Ile Leu
            1125                1130                1135

Asn Asn Leu Glu Arg Glu Lys Lys Asp Lys Asn Ile Lys Lys Arg Lys
            1140                1145                1150

Lys Tyr Asn Lys Lys Asn Phe Asn Pro Val Ser Leu Asn Asn Ile Cys
            1155                1160                1165

Asn Phe Ser Leu Lys Cys Leu Gly Asn Met Arg His Asn Asn Ser
    1170                1175                1180

Leu Phe Lys Asn Thr Leu Thr Lys Thr Gly Glu Ile Glu Leu Lys Leu
1185                1190                1195                1200

Lys Lys Trp Leu His Tyr Leu Lys Asn Trp Phe Tyr Lys Lys Arg
            1205                1210                1215

Met Lys Lys Tyr Ile Lys Asn Lys Leu Lys Asn Asn Lys Lys Ile Tyr
            1220                1225                1230

Ala Tyr Ile Cys Ile Gly Asp Phe Ser Asn Cys Tyr Glu His Ile Asn
            1235                1240                1245

His Asn Tyr Leu Phe Lys Ile Leu Lys Asn Phe Phe Asp Asn Ile Asn
    1250                1255                1260

Asn Phe Glu Phe Ile Tyr Leu Phe Lys Arg Ser Phe Arg Leu Tyr Asn
1265                1270                1275                1280

Lys Asn Leu Asn Asn Ser Phe Leu Ser Tyr Tyr Pro Val Asn Val Lys
```

-continued

```
                1285                1290                1295
Ser Phe Gly Leu His Tyr Ile Arg Asn Leu Arg Glu Leu Ile Ile Lys
        1300                1305                1310
Ser His Leu Asn Asp Asn His His Phe Leu Leu Asn Gln Met Phe Lys
        1315                1320                1325
Thr Lys Ser Lys Ser Asp Leu Tyr Ile Phe Ala Asp Ser Tyr Lys Ser
        1330                1335                1340
Leu Gln Val Asp Lys Arg Asp Ile Phe Met Thr Ile Thr Val Ile
1345                1350                1355                1360
Arg Tyr Tyr Tyr Leu Asn Ile Tyr Phe Ser Ile Lys Glu Phe Lys Leu
                1365                1370                1375
Asn Arg Lys Asn Ile Phe Tyr Phe Gln Ile Phe Gln Glu Asn Gln Met
        1380                1385                1390
Lys Gly Val Tyr Leu Ser Val Arg Asp Lys Lys Arg Val Glu Asn Ile
        1395                1400                1405
Lys Lys Trp Tyr Leu Asn Ser Met Lys Lys Ile Asn His Asp Glu Ile
        1410                1415                1420
Leu Glu Ser Leu Lys Asn Ser Ser Ile Asn Ile Asn Asn Lys Asn Phe
1425                1430                1435                1440
Met Ile Cys Thr Asn His Glu Gln Asp Thr Glu Glu Lys Gly Asn Thr
                1445                1450                1455
Gln Asn Lys Glu Lys His Asp Ile Tyr Ile Gly Pro Ile Tyr Asn Asn
        1460                1465                1470
Ser Phe Asp Ser Thr Thr Thr Thr His Ser Ser Asn Asn Tyr Lys Gly
        1475                1480                1485
Asn Asn Ile His Val Ser Gly Asp Tyr Lys Asn Asp Gly Leu Leu His
        1490                1495                1500
Lys Gly Asn Asn Ser Met Asn Glu Cys Tyr Val Lys Asp Ile Lys Cys
1505                1510                1515                1520
Asn Asn Asn Asn Asn Asn Asn Asn Asn Asn Asn Asn Asn Asn Ile Asn
                1525                1530                1535
Asn Ser Tyr Asn Lys Leu Asn Cys Val Thr Asn Asn Ser Lys Asn Asp
        1540                1545                1550
Ile Ile Lys Tyr His Lys Thr Ile Asp Thr Asp Asn Ser Lys Asn His
        1555                1560                1565
Thr Tyr Phe Lys Asn Lys Phe Leu Asn Phe Leu Asp Lys Lys Ile Ile
    1570                1575                1580
Ser Asn Ile Tyr Gly Leu Pro Gln Gly Phe Ser Leu Ser Asn Ile Leu
1585                1590                1595                1600
Cys Ser Leu Tyr Tyr Ala Tyr Leu Asp Lys Asn Glu Glu Phe Gln Asn
                1605                1610                1615
Leu Leu Tyr Ser Glu Lys Gln Ile Asn Asn Lys Tyr Phe Leu Ala Asn
        1620                1625                1630
Gly Thr Cys Asn Tyr Phe Asn Leu Asn Ser Leu Ile Leu Arg Phe Ile
        1635                1640                1645
Asp Asp Phe Leu Phe Ile Thr Leu Asn Lys Lys Asn Ile Lys Ile Phe
    1650                1655                1660
Lys Asn Leu Leu Leu Lys Lys Lys Ile Trp Gly Ser Asn Ile Asn Ser
1665                1670                1675                1680
Ser Lys Thr Lys Ile Phe Lys Ile Pro Leu Ile Tyr Lys Asn Asp Leu
        1685                1690                1695
Leu Ile Tyr Asn Phe Gln Asn Lys Tyr Gln Lys Lys Tyr Lys Ile
        1700                1705                1710
```

-continued

```
Lys Asn Lys Lys Lys Ile Gln Ser Val Arg Asn Lys Arg Ile His Asn
    1715                1720                1725

Gln Leu Val Asn Ala Asn Lys Lys Lys His Thr Ser Val Gln Lys Asp
    1730                1735                1740

Lys Ile Asn Lys Tyr Ile Asn Leu Ile His Pro Thr Ile Gln Lys Asn
1745                1750                1755                1760

Asp Ser Val Leu Ser Ser Asn Ser Ile Met Asn Phe Glu Arg Ile Tyr
            1765                1770                1775

Ile Lys Glu Ser His Lys Ser Asn Ser Ser Ile Arg Thr Asp Ile Pro
                1780                1785                1790

Asn Ser Val Val Asn Asp Asp Ile Glu Tyr Asn Gln Lys Ser Asp Asn
    1795                1800                1805

Asn Ser Tyr Ser Thr Asn Asn Leu Tyr Asn Asn Ile Asn Met Thr Gln
    1810                1815                1820

Asn Gly Asp Asn Asn Asn Val Asn Ile Phe Lys His Val Gln Asn Asp
1825                1830                1835                1840

Ser Phe Gln Cys Phe Asn Ser Asn Asn Leu Tyr Ile Glu Lys Asp Ile
            1845                1850                1855

Lys Glu Asn Asn Ile Ser Gln Ile Asn Arg Lys Leu Cys Ser Lys Arg
        1860                1865                1870

Asn Phe Thr Lys Lys Ser Arg Lys Ile Asn Thr Leu Thr Tyr Leu Gln
        1875                1880                1885

Ile Asp Lys Val Ile Lys Ile Leu Lys Cys Lys Lys Lys Tyr Ile Lys
    1890                1895                1900

His Ile Lys Lys Met Lys Tyr Met Asn Phe Gln Asn Phe Lys Lys
1905                1910                1915                1920

Leu Lys Lys Leu Gln Lys Phe His Asn Ala Ser Phe Glu Leu Lys Ile
            1925                1930                1935

Asn Lys Ile Asn Lys Asn Ile Arg Arg Leu Asn Lys Leu Lys Lys Arg
                1940                1945                1950

Lys Asn His Ser Ile Asn Ile Thr Pro Val Thr Ser Ile Glu Trp Leu
        1955                1960                1965

Asn Asn Ser Tyr Thr Phe Asp Phe Ile Asn Asn Ser Ile Gln Ser Thr
    1970                1975                1980

Ser Tyr Pro Trp Lys Asn Lys Cys Asp Ala Thr Ile Arg Asn His Leu
1985                1990                1995                2000

His Leu His Asn Val Ile Ile Asp Lys Asn Asn Lys Thr Tyr Phe Met
            2005                2010                2015

Lys Asn Leu Val Glu Asn Arg Ile Val Arg Asn Ile Ile Ser Lys Gln
        2020                2025                2030

Lys Lys Cys Gln Ser Leu Tyr Lys Asn Lys Gln Asn Val Tyr Phe Cys
        2035                2040                2045

Tyr Lys Asn Asn Phe Ser Leu Leu Lys Ser Ser Ile Leu Lys Phe Ile
    2050                2055                2060

Cys Cys Ile Lys Thr Leu Lys Lys Met Phe Asn Ala Phe Thr Asn Ser
2065                2070                2075                2080

Thr Tyr Asn Thr Lys Phe Ile Leu Phe Leu Ile Ser Tyr Met Asn Lys
            2085                2090                2095

Met Leu Ile Lys Asn Lys Lys Leu Lys Phe Val Lys Leu Phe Leu Ile
        2100                2105                2110

Gln Thr Ala Ile Glu Ala Phe Arg Tyr Ala Arg Ile Phe Asn Gln Gln
        2115                2120                2125
```

```
Asp Ser Phe Tyr Pro Cys Leu Gln His Phe Arg Lys Ile Lys Lys Arg
    2130                2135                2140

Leu Ile Asn Lys Tyr Lys Ile Gly His Asn Lys Asn Leu Leu Arg Glu
2145                2150                2155                2160

Phe Phe Phe Leu Phe Asn Phe Ile Lys Lys Glu Leu Tyr Asn Ser Trp
                2165                2170                2175

Pro Tyr Met Phe Lys Ile Lys Asn
            2180

<210> SEQ ID NO 7
<211> LENGTH: 4185
<212> TYPE: DNA
<213> ORGANISM: Plasmodium falciparum
<220> FEATURE:
<221> NAME/KEY: CDS
<222> LOCATION: (1)..(2382)
<223> OTHER INFORMATION: Partial TERT gene

<400> SEQUENCE: 7
```

| | | | | | | | | | | | | | | | | |
|---|---|---|---|---|---|---|---|---|---|---|---|---|---|---|---|---|
| atg | aag | ggt | gtt | tat | ttg | ggt | gcc | cgt | gat | aag | aaa | agg | gtt | gaa | aat | 48 |
| Met | Lys | Gly | Val | Tyr | Leu | Gly | Ala | Arg | Asp | Lys | Lys | Arg | Val | Glu | Asn | |
| 1 | | | | 5 | | | | | 10 | | | | | 15 | | |

```
att aaa aaa tgg tat tta aac agc atg aaa aaa ata aat cac gac gaa      96
Ile Lys Lys Trp Tyr Leu Asn Ser Met Lys Lys Ile Asn His Asp Glu
             20                  25                  30 ata cta gaa agt tta aaa aat tca tcc ata aat ata aat aat aaa aac     144
Ile Leu Glu Ser Leu Lys Asn Ser Ser Ile Asn Ile Asn Asn Lys Asn
         35                  40                  45 ttt atg ata tgt acc aat cat gag caa gat aca gaa gaa aaa gga aat     192
Phe Met Ile Cys Thr Asn His Glu Gln Asp Thr Glu Glu Lys Gly Asn
     50                  55                  60 aca caa aat aag gag aag cat gat att tat att gga cca ata tat aat     240
Thr Gln Asn Lys Glu Lys His Asp Ile Tyr Ile Gly Pro Ile Tyr Asn
 65                  70                  75                  80 aat tcg ttc gac agt aca aca aca aca cat agt agt aat aat tat aaa     288
Asn Ser Phe Asp Ser Thr Thr Thr Thr His Ser Ser Asn Asn Tyr Lys
                 85                  90                  95 ggg aat aat atc cat gtg agt ggg gat tat aag aat gat ggg cta tta     336
Gly Asn Asn Ile His Val Ser Gly Asp Tyr Lys Asn Asp Gly Leu Leu
            100                 105                 110 cat aaa ggt aat aat agt atg aat gaa tgt tat gtg aag gac ata aaa     384
His Lys Gly Asn Asn Ser Met Asn Glu Cys Tyr Val Lys Asp Ile Lys
        115                 120                 125 tgt aat aat aat aat aat aat aat aat aat aac aac aac aat aat att     432
Cys Asn Asn Asn Asn Asn Asn Asn Asn Asn Asn Asn Asn Asn Asn Ile
    130                 135                 140 aat aat agt tat aat aaa tta aat tgt gtt acg aat aat agc aaa aat     480
Asn Asn Ser Tyr Asn Lys Leu Asn Cys Val Thr Asn Asn Ser Lys Asn
145                 150                 155                 160 gac ata att aaa tac cac aaa act atc gac aca gat aat agt aaa aat     528
Asp Ile Ile Lys Tyr His Lys Thr Ile Asp Thr Asp Asn Ser Lys Asn
                165                 170                 175 cat aca tac ttt aaa aat aaa ttc cta aat ttt ttg gat aaa aaa att     576
His Thr Tyr Phe Lys Asn Lys Phe Leu Asn Phe Leu Asp Lys Lys Ile
            180                 185                 190 att agt aat ata tat ggc tta cca caa ggt ttt agc tta tct aat ata     624
Ile Ser Asn Ile Tyr Gly Leu Pro Gln Gly Phe Ser Leu Ser Asn Ile
        195                 200                 205 ttg tgc tcc cta tat tat gca tat cta gat aaa aat gaa gaa tct caa     672
Leu Cys Ser Leu Tyr Tyr Ala Tyr Leu Asp Lys Asn Glu Glu Ser Gln
    210                 215                 220
```

```
aat tta tta tat tca gaa aaa caa atc aat aat aaa tat ttc tta gca    720
Asn Leu Leu Tyr Ser Glu Lys Gln Ile Asn Asn Lys Tyr Phe Leu Ala
225             230                 235                 240 aat gga act tgt aat tat ttc aat tta aat tca ctc ata ctc cga ttt    768
Asn Gly Thr Cys Asn Tyr Phe Asn Leu Asn Ser Leu Ile Leu Arg Phe
                245                 250                 255 att gat gac ttt tta ttt ata act ctt aat aaa aaa aat att aaa ata    816
Ile Asp Asp Phe Leu Phe Ile Thr Leu Asn Lys Lys Asn Ile Lys Ile
                260                 265                 270 ttt aaa aac tta cta tta aaa aaa aaa ata tgg gga agt aat att aat    864
Phe Lys Asn Leu Leu Leu Lys Lys Lys Ile Trp Gly Ser Asn Ile Asn
            275                 280                 285 tca tcc aaa acc aaa atc ttc aaa ata cca ctt ata tat aaa aat gat    912
Ser Ser Lys Thr Lys Ile Phe Lys Ile Pro Leu Ile Tyr Lys Asn Asp
        290                 295                 300 tta cta ata tat aat ttt caa aat aaa tac caa caa aaa aaa aaa tac    960
Leu Leu Ile Tyr Asn Phe Gln Asn Lys Tyr Gln Gln Lys Lys Lys Tyr
305             310                 315                 320 aaa ata aaa aat aaa aaa aaa ata caa agt gtg agg aac aaa cgg ata   1008
Lys Ile Lys Asn Lys Lys Lys Ile Gln Ser Val Arg Asn Lys Arg Ile
                325                 330                 335 cat aat cag cta gtc aat gct aat aaa aaa aaa cac aca tct gta caa   1056
His Asn Gln Leu Val Asn Ala Asn Lys Lys Lys His Thr Ser Val Gln
                340                 345                 350 aaa gat aaa ata aat aaa tat ata aat ctc ata cat cca aca ata caa   1104
Lys Asp Lys Ile Asn Lys Tyr Ile Asn Leu Ile His Pro Thr Ile Gln
            355                 360                 365 aaa aat gat tct gtc ttg tct tct aat tct att atg aat ttt gaa agg   1152
Lys Asn Asp Ser Val Leu Ser Ser Asn Ser Ile Met Asn Phe Glu Arg
        370                 375                 380 ata tat aat aaa gaa agt cat aaa agt aac agt tca ata cgt acg gat   1200
Ile Tyr Asn Lys Glu Ser His Lys Ser Asn Ser Ser Ile Arg Thr Asp
385             390                 395                 400 att ccg aat agt gtt gta aat gac gat ata gaa tat aat caa aaa agt   1248
Ile Pro Asn Ser Val Val Asn Asp Asp Ile Glu Tyr Asn Gln Lys Ser
                405                 410                 415 gat aat aat tct tac agt act aat aat tta tac aac aat ata aat atg   1296
Asp Asn Asn Ser Tyr Ser Thr Asn Asn Leu Tyr Asn Asn Ile Asn Met
                420                 425                 430 act caa aat ggt gat aat aat aat gtt aat att ttt aaa cat gta caa   1344
Thr Gln Asn Gly Asp Asn Asn Asn Val Asn Ile Phe Lys His Val Gln
            435                 440                 445 aat gat tct ttt caa tgt ttt aat agt aac aac tta tat att gaa aag   1392
Asn Asp Ser Phe Gln Cys Phe Asn Ser Asn Asn Leu Tyr Ile Glu Lys
        450                 455                 460 gat ata aaa gaa aat aat att tca caa atc aac aga aag tta tgt act   1440
Asp Ile Lys Glu Asn Asn Ile Ser Gln Ile Asn Arg Lys Leu Cys Thr
465             470                 475                 480 aaa aga aat ttt aca aaa aaa agt aga aaa ata aat act gtg aca tat   1488
Lys Arg Asn Phe Thr Lys Lys Ser Arg Lys Ile Asn Thr Val Thr Tyr
                485                 490                 495 cta caa att gat aaa gtt ata aaa atc cta aaa tgt aag aag aaa tat   1536
Leu Gln Ile Asp Lys Val Ile Lys Ile Leu Lys Cys Lys Lys Lys Tyr
                500                 505                 510 ata aaa cat ata aaa aag atg aag tat atg aat aat ttt caa aat ttt   1584
Ile Lys His Ile Lys Lys Met Lys Tyr Met Asn Asn Phe Gln Asn Phe
            515                 520                 525 aaa aaa tta aaa aaa tta caa aaa ttt caa aat gcc tct ttt gaa tta   1632
Lys Lys Leu Lys Lys Leu Gln Lys Phe Gln Asn Ala Ser Phe Glu Leu
```

```
                  530                 535                 540
aaa att aat aaa att aat aaa aat att aga cga ttg aat aaa tta aaa       1680
Lys Ile Asn Lys Ile Asn Lys Asn Ile Arg Arg Leu Asn Lys Leu Lys
545                 550                 555                 560 aaa cgt aaa aat cat tct ata aac att act cct gtt act tct ata gaa       1728
Lys Arg Lys Asn His Ser Ile Asn Ile Thr Pro Val Thr Ser Ile Glu
                565                 570                 575 tgg tta aat aat tca tac aca ttt gat ttt ata aat aat tct ata caa       1776
Trp Leu Asn Asn Ser Tyr Thr Phe Asp Phe Ile Asn Asn Ser Ile Gln
                    580                 585                 590 agc act tca tat cca tgg aaa aat aaa tgt gat gct act att aga aat       1824
Ser Thr Ser Tyr Pro Trp Lys Asn Lys Cys Asp Ala Thr Ile Arg Asn
                595                 600                 605 cat tta cat cta cat aat gtt att ata gat aaa aat aat aaa act tat       1872
His Leu His Leu His Asn Val Ile Ile Asp Lys Asn Asn Lys Thr Tyr
610                 615                 620 ttt atg aaa aac cta gtt gaa aat aga att gta cga aat att ata tcc       1920
Phe Met Lys Asn Leu Val Glu Asn Arg Ile Val Arg Asn Ile Ile Ser
625                 630                 635                 640 aaa caa aaa aaa tgt caa tcc tta tat aag aat aag caa aat gta tat       1968
Lys Gln Lys Lys Cys Gln Ser Leu Tyr Lys Asn Lys Gln Asn Val Tyr
                    645                 650                 655 ttc tgt tat aaa aat aat ttt agc tta tta aaa tca tct ata tta aaa       2016
Phe Cys Tyr Lys Asn Asn Phe Ser Leu Leu Lys Ser Ser Ile Leu Lys
                660                 665                 670 ttc atc tgt tgt att aaa aca ctc aaa aaa atg ttt aat gca ttt aca       2064
Phe Ile Cys Cys Ile Lys Thr Leu Lys Lys Met Phe Asn Ala Phe Thr
            675                 680                 685 aat tct aca tat aac aca aaa ttt ata tta ttt ctc ata tcg tat atg       2112
Asn Ser Thr Tyr Asn Thr Lys Phe Ile Leu Phe Leu Ile Ser Tyr Met
690                 695                 700 aat aaa atg tta ata aaa aat aaa aaa ctc aaa ttt gtc aaa ttg ttt       2160
Asn Lys Met Leu Ile Lys Asn Lys Lys Leu Lys Phe Val Lys Leu Phe
705                 710                 715                 720 tta att caa aca gca atc gaa gcc ttc cgt tat gcc aga att ttt aat       2208
Leu Ile Gln Thr Ala Ile Glu Ala Phe Arg Tyr Ala Arg Ile Phe Asn
                    725                 730                 735 cag cag gat tcc ttt tat ccg tgt ctc caa cat ttc agg aaa atc aaa       2256
Gln Gln Asp Ser Phe Tyr Pro Cys Leu Gln His Phe Arg Lys Ile Lys
                740                 745                 750 aaa aga tta att aac aaa tac aaa att gga cat aac aaa aat tta ttg       2304
Lys Arg Leu Ile Asn Lys Tyr Lys Ile Gly His Asn Lys Asn Leu Leu
            755                 760                 765 cga gaa ttt ttt ttc ctg ttt aat ttt atc aag aaa gag ttg tat aat       2352
Arg Glu Phe Phe Phe Leu Phe Asn Phe Ile Lys Lys Glu Leu Tyr Asn
770                 775                 780 tca tgg cct tac atg ttc aaa ata aaa aat taaaaaaaaa aaaaaaaaa          2402
Ser Trp Pro Tyr Met Phe Lys Ile Lys Asn
785                 790 aaaaaaatat atatatatat atatatatat atatatataa gtataaacgt tgtttatatt     2462
aatatgtcca acttataaag ttatataatt attaattttg ttcatatttt acttaatatt     2522
aattttatac attctattat tttttttttt ttttgcattt gtatttgttt ttaaatatat     2582
attgattttg gattgacata ttttttttt atttttctt tttttttata atcttggctt       2642
ggtgtccaaa catagattgg atattttttt cagagcctgc aactttccac gtgaacctac     2702
cctaatattt accaatcctt ttttattaat attataaagg gtatgtgata tattcttgta     2762
ataatttggc ttgaaaccat actgataaga acttggttct ccagattttt tataaagcaa     2822
```

```
aaatggatat ggttcgagaa ctcttgaagc tctccatttg aatggtctaa tattactata   2882 ataatttta tattttcttc ttataattcc atgatatttt ttaaatgaaa ttttattatg   2942
ccttctacaa aaataaataa cattagatgg tatttctaat aatcttctat taaccatatt   3002
ccaatatttt ggtgcaggca ttactttttt atgtggtaaa taatttcttg aaacttcttc   3062
aagagcctca ctatatattt tacatgtatt gtaatcttta tcaacaaatg atatagaatt   3122
tatattatat aatggaatgg tacttcttag ttgtaataat gattcaacac attcctcaag   3182
taatatatta ctagattgat tcggactata tccatatata cctgctgaga tatccggtaa   3242
tattatagaa gatatacata actcattcaa ttgttttaaa gcattagaaa agcaatatct   3302
taacttattt gatgaaatat atgaattacc ctgccataca tatggcatta ttaaaaatgc   3362
taataatttc acttttttac taacattatg tggtttactt aatataatat caccaatttg   3422
taatgttttt gatccttcat ataattcttt aaatttttgt tctccattta tttctaaaga   3482
tgattgtaca tattcttcct tatgctcatt caatatatca attcttcttt ttattaaatt   3542
tttaattgat agaattatct ctttaactaa ttcgggaccc cctttatta atataaacga   3602 accaaaacca ctcataggta tgaaattaga aaccataggt attaacatac aatctgcttc   3662
ttcatctata atatcattat gtattatttt aatattacca aattcttcta aagtcatatt   3722
tttcatttca tattcatatt tatccttaat tttatttata tctaatatat ccatatcttc   3782
ttctaataaa ccttattct catcattctc cttattattt aaaaaaaaca tatcatttat   3842 ctcactttc atgttaggaa atatttcttt cattcacttt ctattcttcc gttctaatat   3902
atcgagagat ttcgtataat ctatatgata tttaatgct ctttcgttta ttgttttcaa   3962
cctcttggtt aaataggaac taccaaaata acgtttcccc ataaaaaaaa atcttaacat   4022
ttttatatat acccataata atatacaaat aaataaatat atatatatat atatatatgt   4082
atcagtctat actacatggg gttaatgata gaaaaatata ttaaaaatat atttatatac   4142
ttttataaat aggatatata gattattttg atctaaaatg aca                    4185
```

<210> SEQ ID NO 8
<211> LENGTH: 794
<212> TYPE: PRT
<213> ORGANISM: Plasmodium falciparum

<400> SEQUENCE: 8

```
Met Lys Gly Val Tyr Leu Gly Ala Arg Asp Lys Lys Arg Val Glu Asn
 1               5                  10                  15

Ile Lys Lys Trp Tyr Leu Asn Ser Met Lys Lys Ile Asn His Asp Glu
            20                  25                  30

Ile Leu Glu Ser Leu Lys Asn Ser Ser Ile Asn Ile Asn Asn Lys Asn
        35                  40                  45

Phe Met Ile Cys Thr Asn His Glu Gln Asp Thr Glu Glu Lys Gly Asn
    50                  55                  60

Thr Gln Asn Lys Glu Lys His Asp Ile Tyr Ile Gly Pro Ile Tyr Asn
65                  70                  75                  80

Asn Ser Phe Asp Ser Thr Thr Thr His Ser Ser Asn Asn Tyr Lys
                85                  90                  95

Gly Asn Asn Ile His Val Ser Gly Asp Tyr Lys Asn Asp Gly Leu Leu
            100                 105                 110

His Lys Gly Asn Asn Ser Met Asn Glu Cys Tyr Val Lys Asp Ile Lys
        115                 120                 125
```

```
Cys Asn Asn Asn Asn Asn Asn Asn Asn Asn Asn Asn Asn Ile
    130                 135                 140

Asn Asn Ser Tyr Asn Lys Leu Asn Cys Val Thr Asn Ser Lys Asn
145                 150                 155                 160

Asp Ile Ile Lys Tyr His Lys Thr Ile Asp Thr Asp Asn Ser Lys Asn
                165                 170                 175

His Thr Tyr Phe Lys Asn Lys Phe Leu Asn Phe Leu Asp Lys Lys Ile
                180                 185                 190

Ile Ser Asn Ile Tyr Gly Leu Pro Gln Gly Phe Ser Leu Ser Asn Ile
        195                 200                 205

Leu Cys Ser Leu Tyr Tyr Ala Tyr Leu Asp Lys Asn Glu Glu Ser Gln
    210                 215                 220

Asn Leu Leu Tyr Ser Glu Lys Gln Ile Asn Asn Lys Tyr Phe Leu Ala
225                 230                 235                 240

Asn Gly Thr Cys Asn Tyr Phe Asn Leu Asn Ser Leu Ile Leu Arg Phe
                245                 250                 255

Ile Asp Asp Phe Leu Phe Ile Thr Leu Asn Lys Lys Asn Ile Lys Ile
                260                 265                 270

Phe Lys Asn Leu Leu Leu Lys Lys Ile Trp Gly Ser Asn Ile Asn
        275                 280                 285

Ser Ser Lys Thr Lys Ile Phe Lys Ile Pro Leu Ile Tyr Lys Asn Asp
290                 295                 300

Leu Leu Ile Tyr Asn Phe Gln Asn Lys Tyr Gln Gln Lys Lys Lys Tyr
305                 310                 315                 320

Lys Ile Lys Asn Lys Lys Ile Gln Ser Val Arg Asn Lys Arg Ile
                325                 330                 335

His Asn Gln Leu Val Asn Ala Asn Lys Lys His Thr Ser Val Gln
        340                 345                 350

Lys Asp Lys Ile Asn Lys Tyr Ile Asn Leu Ile His Pro Thr Ile Gln
                355                 360                 365

Lys Asn Asp Ser Val Leu Ser Ser Asn Ser Ile Met Asn Phe Glu Arg
370                 375                 380

Ile Tyr Asn Lys Glu Ser His Lys Ser Asn Ser Ser Ile Arg Thr Asp
385                 390                 395                 400

Ile Pro Asn Ser Val Val Asn Asp Asp Ile Glu Tyr Asn Gln Lys Ser
                405                 410                 415

Asp Asn Asn Ser Tyr Ser Thr Asn Asn Leu Tyr Asn Asn Ile Asn Met
                420                 425                 430

Thr Gln Asn Gly Asp Asn Asn Val Asn Ile Phe Lys His Val Gln
        435                 440                 445

Asn Asp Ser Phe Gln Cys Phe Asn Ser Asn Asn Leu Tyr Ile Glu Lys
450                 455                 460

Asp Ile Lys Glu Asn Asn Ile Ser Gln Ile Asn Arg Lys Leu Cys Thr
465                 470                 475                 480

Lys Arg Asn Phe Thr Lys Lys Ser Arg Lys Ile Asn Thr Val Thr Tyr
                485                 490                 495

Leu Gln Ile Asp Lys Val Ile Lys Ile Leu Lys Cys Lys Lys Lys Tyr
                500                 505                 510

Ile Lys His Ile Lys Lys Met Lys Tyr Met Asn Asn Phe Gln Asn Phe
        515                 520                 525

Lys Lys Leu Lys Lys Leu Gln Lys Phe Gln Asn Ala Ser Phe Glu Leu
530                 535                 540

Lys Ile Asn Lys Ile Asn Lys Asn Ile Arg Arg Leu Asn Lys Leu Lys
```

```
545                 550                 555                 560
Lys Arg Lys Asn His Ser Ile Asn Ile Thr Pro Val Thr Ser Ile Glu
                565                 570                 575

Trp Leu Asn Asn Ser Tyr Thr Phe Asp Phe Ile Asn Asn Ser Ile Gln
                580                 585                 590

Ser Thr Ser Tyr Pro Trp Lys Asn Lys Cys Asp Ala Thr Ile Arg Asn
                595                 600                 605

His Leu His Leu His Asn Val Ile Ile Asp Lys Asn Lys Thr Tyr
                610                 615                 620

Phe Met Lys Asn Leu Val Glu Asn Arg Ile Val Arg Asn Ile Ile Ser
625                 630                 635                 640

Lys Gln Lys Lys Cys Gln Ser Leu Tyr Lys Asn Lys Gln Asn Val Tyr
                645                 650                 655

Phe Cys Tyr Lys Asn Asn Phe Ser Leu Leu Lys Ser Ser Ile Leu Lys
                660                 665                 670

Phe Ile Cys Cys Ile Lys Thr Leu Lys Lys Met Phe Asn Ala Phe Thr
                675                 680                 685

Asn Ser Thr Tyr Asn Thr Lys Phe Ile Leu Phe Leu Ile Ser Tyr Met
                690                 695                 700

Asn Lys Met Leu Ile Lys Asn Lys Lys Leu Lys Phe Val Lys Leu Phe
705                 710                 715                 720

Leu Ile Gln Thr Ala Ile Glu Ala Phe Arg Tyr Ala Arg Ile Phe Asn
                725                 730                 735

Gln Gln Asp Ser Phe Tyr Pro Cys Leu Gln His Phe Arg Lys Ile Lys
                740                 745                 750

Lys Arg Leu Ile Asn Lys Tyr Lys Ile Gly His Asn Lys Asn Leu Leu
                755                 760                 765

Arg Glu Phe Phe Phe Leu Phe Asn Phe Ile Lys Lys Glu Leu Tyr Asn
                770                 775                 780

Ser Trp Pro Tyr Met Phe Lys Ile Lys Asn
785                 790

<210> SEQ ID NO 9
<211> LENGTH: 294
<212> TYPE: DNA
<213> ORGANISM: Oryza sativa
<220> FEATURE:
<221> NAME/KEY: CDS
<222> LOCATION: (1)..(270)
<223> OTHER INFORMATION: Fragment of rice TERT gene

<400> SEQUENCE: 9 tta atg agg ttc att gat gat ttc ata ttt atc tct ttc tca ctg gag    48
Leu Met Arg Phe Ile Asp Asp Phe Ile Phe Ile Ser Phe Ser Leu Glu
  1               5                  10                  15 cat gct caa aaa ttc ctc aat agg atg aga aga ggt ttt gtg ttc tac    96
His Ala Gln Lys Phe Leu Asn Arg Met Arg Arg Gly Phe Val Phe Tyr
             20                  25                  30 aat tgc tac atg aac gac agc aaa tat ggc ttt aat ttc tgt gct gga   144
Asn Cys Tyr Met Asn Asp Ser Lys Tyr Gly Phe Asn Phe Cys Ala Gly
         35                  40                  45 aat agt gag cct tcc tct aat aga ctc tac agg ggt gat gat gga gtc   192
Asn Ser Glu Pro Ser Ser Asn Arg Leu Tyr Arg Gly Asp Asp Gly Val
     50                  55                  60 tca ttc atg cca tgg agt ggt ttg cta ata aat tgt gaa act ttg gaa   240
Ser Phe Met Pro Trp Ser Gly Leu Leu Ile Asn Cys Glu Thr Leu Glu
 65                  70                  75                  80
```

```
att caa gct gat tat acg agg tat gac tgt tgaaatttgt ttttagctca    290
Ile Gln Ala Asp Tyr Thr Arg Tyr Asp Cys
                85                  90 ttgg                                                              294
```

<210> SEQ ID NO 10
<211> LENGTH: 90
<212> TYPE: PRT
<213> ORGANISM: Oryza sativa

<400> SEQUENCE: 10

```
Leu Met Arg Phe Ile Asp Asp Phe Ile Phe Ile Ser Phe Ser Leu Glu
 1               5                  10                  15

His Ala Gln Lys Phe Leu Asn Arg Met Arg Arg Gly Phe Val Phe Tyr
            20                  25                  30

Asn Cys Tyr Met Asn Asp Ser Lys Tyr Gly Phe Asn Phe Cys Ala Gly
        35                  40                  45

Asn Ser Glu Pro Ser Ser Asn Arg Leu Tyr Arg Gly Asp Asp Gly Val
    50                  55                  60

Ser Phe Met Pro Trp Ser Gly Leu Leu Ile Asn Cys Glu Thr Leu Glu
65                  70                  75                  80

Ile Gln Ala Asp Tyr Thr Arg Tyr Asp Cys
                85                  90
```

<210> SEQ ID NO 11
<211> LENGTH: 44
<212> TYPE: PRT
<213> ORGANISM: Schizosaccharomyces pombe
<220> FEATURE:
<223> OTHER INFORMATION: T motif of TERT protein

<400> SEQUENCE: 11

```
Trp Leu Tyr Asn Ser Phe Ile Ile Pro Ile Leu Gln Ser Phe Phe Tyr
 1               5                  10                  15

Ile Thr Glu Ser Ser Asp Leu Arg Asn Arg Thr Val Tyr Phe Arg Lys
            20                  25                  30

Asp Ile Trp Lys Leu Leu Cys Arg Pro Phe Ile Thr
        35                  40
```

<210> SEQ ID NO 12
<211> LENGTH: 27
<212> TYPE: PRT
<213> ORGANISM: Schizosaccharomyces pombe
<220> FEATURE:
<223> OTHER INFORMATION: Portion of C motif of TERT protein

<400> SEQUENCE: 12

```
Leu Leu Arg Val Val Asp Asp Phe Leu Phe Ile Thr Val Asn Lys Lys
 1               5                  10                  15

Asp Ala Lys Lys Phe Leu Asn Leu Ser Leu Arg
            20                  25
```

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence:RT-PCR
      primer used with C. albicans sequences

<400> SEQUENCE: 13

```
cagggggtat tgaagagata gaagcagcg                                   29
```

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence:RT-PCR
      primer used with C. albicans sequences

<400> SEQUENCE: 14
tcgttgttat tcacgcgtat cg					22

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence:RT-PCR
      primer used with C. albicans sequences

<400> SEQUENCE: 15
gcgacaattg agagatatcg ag					22

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence:RT-PCR
      primer used with C. albicans sequences

<400> SEQUENCE: 16
gcacttgatc ataaatattc gaatcggggc g				31

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence:RT-PCR
      primer used with C. albicans sequences

<400> SEQUENCE: 17
ttatggaaag agctatacg					19

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence:RT-PCR
      primer used with C. albicans sequences

<400> SEQUENCE: 18
tgagaatccc tgaaacacg					19

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence:RT-PCR
      primer used with C. albicans sequences

<400> SEQUENCE: 19
caatttatgt gaacgcgtcc aactgagcgt ag				32

```
<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence:RT-PCR
      primer used with C. albicans sequences

<400> SEQUENCE: 20
gatacgacat tctatatgc                                                    19

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence:RT-PCR
      primer used with C. albicans sequences

<400> SEQUENCE: 21
tcaatacagg ttggctgag                                                    19

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:C. albicans
      sequencing primer

<400> SEQUENCE: 22
tatttctgtt actcggacca                                                   20

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence:C. albicans
      sequencing primer

<400> SEQUENCE: 23
agagactcct tgttaacc                                                     18

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence:C. albicans
      sequencing primer

<400> SEQUENCE: 24
cagttaaaga tgcacgagg                                                    19

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence:C. albicans
      sequencing primer

<400> SEQUENCE: 25
tgaataacaa cagatctaag c                                                 21
```

```
<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence:C. albicans
      sequencing primer

<400> SEQUENCE: 26
cagcgactgg gatggtgc                                                 18

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence:C. albicans
      sequencing primer

<400> SEQUENCE: 27
attcttgtgg tcgaatcgc                                                19

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence:C. albicans
      sequencing primer

<400> SEQUENCE: 28
taaagcacat tgaatttgg                                                19

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence:C. albicans
      sequencng primer

<400> SEQUENCE: 29
taaatcatcc atatgtatc                                                19

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence:C. albicans
      sequencing primer

<400> SEQUENCE: 30
taacacgaaa gctcgagcg                                                19

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence:C. albicans
      sequencing primer

<400> SEQUENCE: 31
aaacttatca gaccggag                                                 18

<210> SEQ ID NO 32
```

```
<211> LENGTH: 26
<212> TYPE: DNA
<213> ORGANISM: Artificial Sequence
<220> FEATURE:
<223> OTHER INFORMATION: Description of Artificial Sequence:RT-PCR
      primer used with P. falciparum sequences

<400> SEQUENCE: 32
gtcatcaata aatcggagta tgagtg                                        26

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence:RT-PCR
      primer used with P. falciparum sequences

<400> SEQUENCE: 33
ttctaaccaa atctgagc                                                 18

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence:RT-PCR
      primer used with P. falciparum sequences

<400> SEQUENCE: 34
tgcataatat agggagcac                                                19

<210> SEQ ID NO 35
<211> LENGTH: 26
<212> TYPE: DNA
<213> ORGANISM: Artificial Sequence
<220> FEATURE:
<223> OTHER INFORMATION: Description of Artificial Sequence:RT-PCR
      primer used with P. falciparum sequences

<400> SEQUENCE: 35
cttttgccat tctcatatga atatac                                        26

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence:RT-PCR
      primer used with P. falciparum sequences

<400> SEQUENCE: 36
attattatga cgtgtgatg                                                19

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence:RT-PCR
      primer used with P. falciparum sequences

<400> SEQUENCE: 37
catataatta catcgagg                                                 18

<210> SEQ ID NO 38
<211> LENGTH: 21
```

```
<212> TYPE: DNA
<213> ORGANISM: Artificial Sequence
<220> FEATURE:
<223> OTHER INFORMATION: Description of Artificial Sequence: Primer for
      sequencing rice DNA
<220> FEATURE:
<221> NAME/KEY: variation
<222> LOCATION: (4)..(21)
<223> OTHER INFORMATION: k at positions 4, 12, 18, 20 and 21 = g or t.

<400> SEQUENCE: 38
cctkaatatt tkttaatkak k                                              21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Primer for
      sequencing rice DNA
<220> FEATURE:
<221> NAME/KEY: variation
<222> LOCATION: (1)..(20)
<223> OTHER INFORMATION: k at positions 1, 11 and 20 = g or t.

<400> SEQUENCE: 39
ktcatacctc ktataatcak c                                              21

<210> SEQ ID NO 40
<211> LENGTH: 364
<212> TYPE: PRT
<213> ORGANISM: Homo sapiens
<220> FEATURE:
<223> OTHER INFORMATION: Partial TERT sequence

<400> SEQUENCE: 40
```

| Val | Leu | Leu | Lys | Thr | His | Cys | Pro | Leu | Arg | Ala | Gln | Leu | Leu | Arg | Gln |
|---|---|---|---|---|---|---|---|---|---|---|---|---|---|---|---|
| 1 | | | | 5 | | | | | 10 | | | | | 15 | |

| His | Ser | Ser | Pro | Trp | Gln | Val | Tyr | Gly | Phe | Val | Arg | Ala | Cys | Leu | Arg |
|---|---|---|---|---|---|---|---|---|---|---|---|---|---|---|---|
| | | | 20 | | | | | 25 | | | | | 30 | | |

| Arg | Leu | Val | Pro | Pro | Gly | Leu | Trp | Gly | Arg | His | Asn | Glu | Arg | Arg | Phe |
|---|---|---|---|---|---|---|---|---|---|---|---|---|---|---|---|
| | 35 | | | | | 40 | | | | | 45 | | | | |

| Leu | Arg | Asn | Thr | Lys | Lys | Phe | Ile | Ser | Leu | Gly | Lys | His | Ala | Lys | Leu |
|---|---|---|---|---|---|---|---|---|---|---|---|---|---|---|---|
| 50 | | | | | 55 | | | | | 60 | | | | | |

| Ser | Leu | Gln | Glu | Leu | Thr | Trp | Lys | Met | Ser | Val | Arg | Ile | Leu | Ala | Lys |
|---|---|---|---|---|---|---|---|---|---|---|---|---|---|---|---|
| 65 | | | | | 70 | | | | | 75 | | | | | 80 |

| Phe | Leu | His | Trp | Leu | Met | Ser | Val | Tyr | Val | Val | Glu | Leu | Leu | Arg | Ser |
|---|---|---|---|---|---|---|---|---|---|---|---|---|---|---|---|
| | | | | 85 | | | | | 90 | | | | | 95 | |

| Phe | Phe | Tyr | Val | Thr | Glu | Thr | Thr | Phe | Gln | Lys | Asn | Leu | Phe | Phe | Tyr |
|---|---|---|---|---|---|---|---|---|---|---|---|---|---|---|---|
| | | | 100 | | | | | 105 | | | | | 110 | | |

| Arg | Lys | Ser | Val | Trp | Ser | Lys | Leu | Gln | Ser | Ile | Gly | Ile | Arg | Gln | His |
|---|---|---|---|---|---|---|---|---|---|---|---|---|---|---|---|
| | 115 | | | | | 120 | | | | | 125 | | | | |

| Leu | Lys | Leu | Arg | Glu | Leu | Ser | Glu | Ala | Glu | Val | Arg | Ser | Arg | Leu | Arg |
|---|---|---|---|---|---|---|---|---|---|---|---|---|---|---|---|
| 130 | | | | | 135 | | | | | 140 | | | | | |

| Phe | Ile | Pro | Lys | Pro | Asp | Gly | Leu | Arg | Pro | Ile | Met | Asn | Met | Asp | Tyr |
|---|---|---|---|---|---|---|---|---|---|---|---|---|---|---|---|
| 145 | | | | | 150 | | | | | 155 | | | | | 160 |

| Val | Val | Gly | Ala | Arg | Thr | Phe | Arg | Ala | Glu | Arg | Leu | Thr | Ser | Arg | Val |
|---|---|---|---|---|---|---|---|---|---|---|---|---|---|---|---|
| | | | | 165 | | | | | 170 | | | | | 175 | |

| Lys | Ala | Leu | Phe | Ser | Val | Leu | Asn | Tyr | Glu | Ala | Arg | Arg | Pro | Gly | Leu |
|---|---|---|---|---|---|---|---|---|---|---|---|---|---|---|---|
| | | | 180 | | | | | 185 | | | | | 190 | | |

| Leu | Gly | Ala | Ser | Val | Leu | Gly | Leu | Asp | Asp | Ile | His | Arg | Ala | Trp | Arg |
|---|---|---|---|---|---|---|---|---|---|---|---|---|---|---|---|
| | 195 | | | | | 200 | | | | | 205 | | | | |

```
Thr Phe Val Leu Arg Val Arg Pro Glu Leu Tyr Phe Val Lys Val Asp
    210                 215                 220

Val Thr Gly Ala Tyr Asp Thr Ile Pro Gln Asp Arg Leu Thr Glu Val
225                 230                 235                 240

Ile Ala Ser Ile Ile Lys Pro Gln Asn Ser Pro Leu Arg Asp Ala Val
                245                 250                 255

Val Ile Glu Gln Ser Tyr Val Gln Cys Gln Gly Ile Pro Gln Gly Ser
                260                 265                 270

Ile Leu Ser Thr Leu Leu Cys Ser Leu Cys Tyr Gly Asp Met Glu Asn
                275                 280                 285

Lys Leu Phe Ala Gly Ile Arg Arg Asp Leu Leu Arg Leu Val Asp
    290                 295                 300

Asp Phe Leu Leu Val Thr Pro His Leu Thr His Ala Lys Thr Phe Ile
305                 310                 315                 320

Arg Thr Leu Val Arg Gly Val Pro Glu Tyr Gly Cys Val Val Asn Leu
                325                 330                 335

Arg Lys Thr Val Val Asn Phe Gln Met Pro Ala His Gly Leu Phe Pro
                340                 345                 350

Trp Cys Gly Leu Leu Asp Thr Arg Thr Leu Glu
                355                 360

<210> SEQ ID NO 41
<211> LENGTH: 364
<212> TYPE: PRT
<213> ORGANISM: Mus musculus
<220> FEATURE:
<223> OTHER INFORMATION: Partial TERT sequence

<400> SEQUENCE: 41

Arg Leu Leu Arg Ser His Cys Arg Phe Arg Thr Asp Leu Leu Arg Leu
1               5                   10                  15

His Ser Ser Pro Trp Gln Val Tyr Gly Phe Leu Arg Ala Cys Leu Cys
                20                  25                  30

Lys Val Val Ser Ala Ser Leu Trp Gly Arg His Asn Glu Arg Arg Phe
            35                  40                  45

Phe Lys Asn Leu Lys Lys Phe Ile Ser Leu Gly Lys Tyr Gly Lys Leu
    50                  55                  60

Ser Leu Gln Glu Leu Met Trp Lys Met Lys Val Glu Ile Leu Ala Thr
65                  70                  75                  80

Phe Leu Phe Trp Leu Met Asp Thr Tyr Val Val Gln Leu Leu Arg Ser
                85                  90                  95

Phe Phe Tyr Ile Thr Glu Ser Thr Phe Gln Lys Asn Leu Phe Phe Tyr
                100                 105                 110

Arg Lys Ser Val Trp Ser Lys Leu Gln Ser Ile Gly Val Arg Gln His
            115                 120                 125

Leu Glu Leu Arg Glu Leu Ser Gln Glu Glu Val Arg Cys Arg Leu Arg
    130                 135                 140

Phe Ile Pro Lys Pro Asn Gly Leu Arg Pro Ile Met Asn Met Ser Tyr
145                 150                 155                 160

Ser Met Gly Thr Arg Ala Leu Gly Ala Gln His Phe Thr Gln Arg Leu
                165                 170                 175

Lys Thr Leu Phe Ser Met Leu Asn Tyr Glu Thr Lys His Pro His Leu
            180                 185                 190

Met Gly Ser Ser Val Leu Gly Met Asn Asp Ile Tyr Arg Thr Trp Arg
    195                 200                 205
```

```
Ala Phe Val Leu Arg Val Arg Pro Arg Met Tyr Phe Val Lys Ala Asp
    210                 215                 220

Val Thr Gly Ala Tyr Asp Ala Ile Pro Gln Gly Arg Leu Val Glu Val
225                 230                 235                 240

Val Ala Asn Met Ile Arg His Ser Glu Ser Ala Leu Arg Asn Ser Val
                245                 250                 255

Val Ile Glu Gln Ser Tyr Thr Gln Cys Gln Gly Ile Pro Gln Gly Ser
            260                 265                 270

Ser Leu Ser Thr Leu Leu Cys Ser Leu Cys Phe Gly Asp Met Glu Asn
        275                 280                 285

Lys Leu Phe Ala Glu Val Gln Arg Asp Leu Leu Arg Phe Val Asp
    290                 295                 300

Asp Phe Leu Leu Val Thr Pro His Leu Asp Gln Ala Lys Thr Phe Ile
305                 310                 315                 320

Ser Thr Leu Val Arg Gly Val Pro Glu Tyr Gly Cys Met Ile Asn Leu
                325                 330                 335

Gln Lys Thr Val Val Asn Phe Gln Ile Pro Ala His Cys Leu Phe Pro
            340                 345                 350

Trp Cys Gly Leu Leu Leu Asp Thr Gln Thr Leu Glu
            355                 360

<210> SEQ ID NO 42
<211> LENGTH: 364
<212> TYPE: PRT
<213> ORGANISM: Oxytricha trifallax
<220> FEATURE:
<223> OTHER INFORMATION: Partial TERT sequence

<400> SEQUENCE: 42

Tyr Tyr Leu Ser Lys Asn Cys Pro Leu Pro Glu Gln Leu Phe Glu Tyr
  1               5                  10                  15

Gln Gln Asp Gln Arg Gln Ile Ser Asn Phe Leu Thr Glu Phe Val Ala
             20                  25                  30

Asn Val Phe Pro Lys Asn Phe Leu Glu Gly Lys Asn Lys Lys Ile Phe
         35                  40                  45

Asn Lys Lys Met Leu Gln Phe Val Lys Phe Asn Arg Phe Glu Ser Phe
     50                  55                  60

Thr Lys Ile Ser Leu Leu Asn Lys Phe Arg Val Asn Val Phe Phe Lys
 65                  70                  75                  80

Val Leu Lys Trp Met Phe Glu Asp Leu Ala Ile Thr Leu Met Arg Cys
                 85                  90                  95

Tyr Phe Tyr Ser Thr Glu Lys Ala Lys Glu Tyr Gln Leu Phe Tyr Tyr
            100                 105                 110

Arg Lys Asn Ile Trp Asn Met Ile Met Arg Leu Ser Ile Asp Asp Leu
        115                 120                 125

Leu Lys Leu Lys Gln Val Glu Lys Lys Glu Met Arg Gly Lys Leu Arg
    130                 135                 140

Leu Ile Pro Lys Gly Asp Thr Phe Arg Pro Ile Met Thr Phe Asn Arg
145                 150                 155                 160

Lys Ile Pro Asn Gln Val Gly Lys Met Thr Thr Asn Asn Lys Leu Gln
                165                 170                 175

Thr Ala His Met Met Leu Lys Asn Leu Lys Lys Met Phe Lys His Ser
            180                 185                 190

Phe Gly Phe Ala Val Phe Asn Tyr Asp Asp Ile Met Lys Arg Tyr Glu
        195                 200                 205
```

```
Asn Phe Val Gln Lys Trp Lys Pro Lys Leu Tyr Phe Val Ala Met Asp
    210                 215                 220

Ile Glu Lys Cys Tyr Asp Asn Val Asp Cys Glu Arg Val Val Asn Phe
225                 230                 235                 240

Leu Gln Lys Ser Asp Leu Met Asp Lys Leu Asn Met Lys Arg Thr Ile
            245                 250                 255

Ile Val Glu Gln Glu Tyr Arg Gln Met Lys Gly Ile Pro Gln Gly Leu
        260                 265                 270

Cys Val Ser Tyr Ile Leu Ser Ser Phe Tyr Ala Asn Leu Glu Glu
        275                 280                 285

Asn Ala Leu Gln Phe Leu Arg Lys Glu Leu Leu Met Arg Leu Thr Asp
    290                 295                 300

Asp Tyr Leu Leu Met Thr Thr Glu Lys Asn Asn Ala Met Leu Phe Ile
305                 310                 315                 320

Glu Lys Leu Tyr Gln Leu Ser Leu Gly Asn Phe Phe Lys Phe His Met
                325                 330                 335

Lys Lys Leu Lys Thr Asn Phe Asp Ser Ile Asn Asp Leu Phe His
            340                 345                 350

Trp Ile Gly Ile Ser Ile Asp Ile Lys Thr Leu Asn
            355                 360

<210> SEQ ID NO 43
<211> LENGTH: 364
<212> TYPE: PRT
<213> ORGANISM: Euplotes aediculatus
<220> FEATURE:
<223> OTHER INFORMATION: Partial TERT sequence

<400> SEQUENCE: 43

Tyr Tyr Leu Thr Lys Ser Cys Pro Leu Pro Glu Glu Leu Phe Ser Tyr
  1               5                  10                  15

Thr Thr Asp Asn Lys Cys Val Thr Gln Phe Ile Asn Glu Phe Phe Tyr
             20                  25                  30

Asn Ile Leu Pro Lys Asp Phe Leu Thr Gly Arg Asn Arg Lys Asn Phe
         35                  40                  45

Gln Lys Lys Val Lys Lys Tyr Val Glu Leu Asn Lys His Glu Leu Ile
     50                  55                  60

His Lys Asn Leu Leu Glu Lys Ile Asn Thr Arg Val Leu Trp Lys
 65                  70                  75                  80

Leu Leu Arg Trp Ile Phe Phe Asp Leu Val Val Ser Leu Thr Arg Cys
                 85                  90                  95

Phe Phe Tyr Met Thr Glu Gln Gln Lys Ser Tyr Ser Thr Tyr Tyr Tyr
                100                 105                 110

Arg Lys Asn Ile Trp Asp Val Ile Met Lys Met Ser Ile Ala Asp Leu
            115                 120                 125

Lys Lys Leu Ala Glu Val Gln Glu Lys Glu Val Glu Gly Lys Leu Arg
130                 135                 140

Leu Ile Pro Lys Lys Thr Thr Phe Arg Pro Ile Met Thr Phe Asn Lys
145                 150                 155                 160

Lys Ile Val Asn Ser Asp Arg Lys Leu Thr Thr Asn Thr Lys Leu Leu
                165                 170                 175

Asn Ser His Leu Met Leu Lys Thr Leu Lys Arg Met Phe Lys Asp Pro
            180                 185                 190

Phe Gly Phe Ala Val Phe Asn Tyr Asp Asp Val Met Lys Lys Tyr Glu
        195                 200                 205
```

```
Glu Phe Val Cys Lys Trp Lys Pro Lys Leu Phe Phe Ala Thr Met Asp
    210                 215                 220

Ile Glu Lys Cys Tyr Asp Ser Val Asn Arg Glu Lys Leu Ser Thr Phe
225                 230                 235                 240

Leu Lys Thr Thr Lys Leu Leu Ser Ser Leu Asn Ala Lys Lys Thr Leu
                245                 250                 255

Ile Val Glu Ala Lys Tyr Arg Gln Thr Lys Gly Ile Pro Gln Gly Leu
            260                 265                 270

Cys Val Ser Ser Ile Leu Ser Ser Phe Tyr Tyr Ala Thr Leu Glu Glu
        275                 280                 285

Ser Ser Leu Gly Phe Leu Arg Asp Glu Leu Leu Met Arg Leu Thr Asp
    290                 295                 300

Asp Tyr Leu Leu Ile Thr Thr Gln Glu Asn Asn Ala Val Leu Phe Ile
305                 310                 315                 320

Glu Lys Leu Ile Asn Val Ser Arg Glu Asn Gly Phe Lys Phe Asn Met
                325                 330                 335

Lys Lys Leu Gln Thr Ser Phe Gln Asn Ile Val Gln Asp Tyr Cys Asp
                340                 345                 350

Trp Ile Gly Ile Ser Ile Asp Met Lys Thr Leu Ala
                355                 360

<210> SEQ ID NO 44
<211> LENGTH: 364
<212> TYPE: PRT
<213> ORGANISM: Tetrahymena thermophila
<220> FEATURE:
<223> OTHER INFORMATION: Partial TERT sequence

<400> SEQUENCE: 44

Tyr Leu Leu Lys Lys Phe Cys Lys Leu Pro Glu Ser Leu Tyr Asp Thr
  1               5                  10                  15

Glu Ile Ser Tyr Lys Gln Ile Thr Asn Phe Leu Arg Gln Ile Ile Gln
                20                  25                  30

Asn Cys Val Pro Asn Gln Leu Leu Gly Lys Lys Asn Phe Lys Val Phe
            35                  40                  45

Leu Glu Lys Leu Tyr Glu Phe Val Gln Met Lys Arg Phe Glu Asn Gln
        50                  55                  60

Lys Val Leu Asp Tyr Ile Cys Phe Met Asp Val Phe Ile Leu Gly Asp
65                  70                  75                  80

Leu Ile Val Phe Ile Ile Asn Lys Leu Val Ile Pro Val Leu Arg Tyr
                85                  90                  95

Asn Phe Tyr Ile Thr Glu Lys His Lys Glu Gly Ser Ile Phe Tyr Tyr
            100                 105                 110

Arg Lys Pro Ile Trp Lys Leu Val Ser Lys Leu Thr Ile Val Lys Leu
        115                 120                 125

Glu Glu Leu Glu Lys Val Glu Glu Lys Leu Ile Pro Gly Lys Leu Arg
    130                 135                 140

Ile Ile Pro Lys Lys Gly Ser Phe Arg Pro Ile Met Thr Phe Leu Arg
145                 150                 155                 160

Lys Asp Lys Gln Lys Asn Ile Lys Leu Asn Leu Asn Gln Ile Leu Met
                165                 170                 175

Asp Ser Gln Leu Val Phe Arg Asn Leu Lys Asp Met Leu Gly Gln Lys
            180                 185                 190

Ile Gly Tyr Ser Val Phe Asp Asn Lys Gln Ile Ser Glu Lys Phe Ala
        195                 200                 205
```

```
Gln Phe Ile Glu Lys Trp Lys Pro Gln Leu Tyr Met Val Thr Leu Asp
    210                 215                 220

Ile Lys Lys Cys Tyr Asp Ser Ile Asp Gln Met Lys Leu Leu Asn Phe
225                 230                 235                 240

Phe Asn Gln Ser Asp Leu Ile Gln Asp Ser Leu Tyr Asp Asp Asp Asp
            245                 250                 255

Gln Ile Leu Gln Lys Phe Arg Gln Lys Arg Gly Ile Pro Gln Gly Leu
                260                 265                 270

Asn Ile Ser Gly Val Leu Cys Ser Phe Tyr Phe Gly Lys Leu Glu Glu
            275                 280                 285

Glu Tyr Thr Gln Phe Leu Lys Asn Ala Leu Leu Met Arg Leu Thr Asp
    290                 295                 300

Asp Tyr Leu Phe Ile Ser Asp Ser Gln Gln Asn Ala Leu Asn Leu Ile
305                 310                 315                 320

Val Gln Leu Gln Asn Cys Ala Asn Asn Asn Gly Phe Met Phe Asn Asp
                325                 330                 335

Gln Lys Ile Thr Thr Asn Phe Lys Ile Ser Val Gln Asn Glu Cys Gln
            340                 345                 350

Trp Ile Gly Lys Ser Ile Asp Met Asn Thr Leu Glu
                355                 360

<210> SEQ ID NO 45
<211> LENGTH: 364
<212> TYPE: PRT
<213> ORGANISM: Schizosaccharomyces pombe
<220> FEATURE:
<223> OTHER INFORMATION: Partial TERT sequence

<400> SEQUENCE: 45

Lys Val Tyr Asn His Tyr Cys Pro Tyr Ile Asp Lys Ile Leu Ser Tyr
  1               5                  10                  15

Ser Leu Lys Pro Asn Gln Val Phe Ala Phe Leu Arg Ser Ile Leu Val
                 20                  25                  30

Arg Val Phe Pro Lys Leu Ile Trp Gly Gln Arg Ile Phe Glu Ile Ile
             35                  40                  45

Leu Lys Asp Leu Glu Thr Phe Leu Lys Leu Ser Arg Tyr Glu Ser Phe
         50                  55                  60

Ser Leu His Tyr Leu Met Ser Asn Ile Lys Ile Ser Ile Phe Ala Glu
 65                  70                  75                  80

Phe Ile Tyr Trp Leu Tyr Asn Ser Phe Ile Pro Ile Leu Gln Ser
                 85                  90                  95

Phe Phe Tyr Ile Thr Glu Ser Ser Asp Leu Arg Asn Thr Val Tyr Phe
            100                 105                 110

Arg Lys Asp Ile Trp Lys Leu Leu Cys Arg Pro Phe Ile Thr Ser Met
        115                 120                 125

Lys Met Phe Glu Lys Ile Asn Glu Asn Asn Val Arg Ala Val Ile Arg
    130                 135                 140

Leu Leu Pro Lys Lys Asn Thr Phe Arg Leu Ile Thr Asn Leu Arg Lys
145                 150                 155                 160

Arg Phe Leu Ile Lys Gln Met Gly Val Ser Thr Asn Gln Thr Leu Arg
                165                 170                 175

Pro Val Ala Ser Leu Leu Lys His Leu Ile Asn Glu Glu Ser Ser Gly
            180                 185                 190

Ile Pro Phe Asn Leu Glu Val Tyr Met Lys Leu Leu Thr Phe Lys Lys
        195                 200                 205
```

```
Asp Leu Leu Lys His Arg Met Arg Lys Lys Tyr Phe Val Arg Ile Asp
        210                 215                 220

Ile Lys Ser Cys Tyr Asp Arg Ile Lys Gln Asp Leu Met Phe Arg Ile
225                 230                 235                 240

Val Lys Lys Lys Leu Lys Asp Pro Glu Thr Leu Phe Val Asp Phe Val
                245                 250                 255

Asp Tyr Trp Thr Lys Tyr Leu Gln Lys Val Gly Ile Pro Gln Gly Ser
            260                 265                 270

Ile Leu Ser Ser Phe Leu Cys His Phe Tyr Met Glu Asp Leu Ile Asp
        275                 280                 285

Glu Tyr Leu Ser Phe Thr Lys Lys Val Leu Leu Arg Val Val Asp
        290                 295                 300

Asp Phe Leu Phe Ile Thr Val Asn Lys Lys Asp Ala Lys Lys Phe Leu
305                 310                 315                 320

Asn Leu Ser Leu Arg Gly Phe Glu Lys His Asn Phe Ser Thr Ser Leu
                325                 330                 335

Glu Lys Thr Val Leu Asn Phe Phe Asn Glu Ser Lys Lys Arg Met Pro
            340                 345                 350

Phe Phe Gly Phe Ser Val Asn Met Arg Ser Leu Asp
            355                 360

<210> SEQ ID NO 46
<211> LENGTH: 364
<212> TYPE: PRT
<213> ORGANISM: Saccharomyces cerevisiae
<220> FEATURE:
<223> OTHER INFORMATION: Partial TERT sequence

<400> SEQUENCE: 46

Ser Asp Leu Asn Ser Ile Cys Pro Pro Leu Glu Ser His Leu Ser Arg
  1               5                  10                  15

Gln Ser Pro Lys Glu Arg Val Leu Lys Phe Ile Ile Val Ile Leu Gln
             20                  25                  30

Lys Leu Leu Pro Gln Glu Met Phe Gly Lys Lys Asn Lys Gly Lys Ile
         35                  40                  45

Ile Lys Asn Leu Asn Leu Leu Ser Leu Pro Leu Asn Gly Tyr Leu
     50                  55                  60

Pro Phe Asp Ser Leu Leu Lys Lys Leu Arg Leu Lys Leu Ala Ile Cys
 65                  70                  75                  80

Phe Ile Ser Trp Leu Phe Arg Gln Leu Ile Pro Lys Ile Ile Gln Thr
                 85                  90                  95

Phe Phe Tyr Cys Thr Glu Ile Ser Ser Thr Val Thr Ile Val Tyr Phe
            100                 105                 110

Arg His Asp Thr Trp Asn Lys Leu Ile Thr Pro Phe Ile Val Glu Tyr
        115                 120                 125

Phe Lys Leu Val Glu Asn Asn Val Cys Arg Asn His Ser Lys Met Arg
130                 135                 140

Ile Ile Pro Lys Lys Ser Asn Phe Arg Ile Ala Ile Pro Cys Arg
145                 150                 155                 160

Gly Ala Asp Glu Glu Glu Phe Thr Lys Asn Ala Ile Gln Pro Thr Gln
                165                 170                 175

Lys Ile Leu Glu Tyr Leu Arg Asn Lys Arg Pro Thr Ser Phe Thr Lys
            180                 185                 190

Ile Tyr Ser Pro Thr Gln Ile Ala Asp Arg Ile Lys Glu Phe Lys Gln
        195                 200                 205
```

```
Arg Leu Leu Lys Lys Phe Asn Pro Glu Leu Tyr Phe Met Lys Phe Asp
    210                 215                 220

Met Lys Ser Cys Tyr Asp Ser Ile Pro Arg Met Glu Cys Met Arg Thr
225                 230                 235                 240

Leu Lys Asp Ala Leu Arg Asn Glu Asn Glu Leu Tyr Ile Asp Asn Val
                245                 250                 255

Arg Thr Val His Leu Tyr Ile Arg Glu Asp Gly Leu Phe Gln Gly Ser
                260                 265                 270

Ser Leu Ser Ala Pro Ile Val Asp Leu Val Tyr Asp Asp Leu Leu Glu
            275                 280                 285

Phe Tyr Ser Glu Phe Lys Ala Ser Pro Leu Ile Leu Lys Leu Ala Asp
    290                 295                 300

Asp Phe Leu Ile Ile Ser Thr Asp Gln Gln Gln Val Ile Asn Ile Lys
305                 310                 315                 320

Lys Leu Ala Met Gly Gly Phe Gln Lys Tyr Asn Ala Lys Ala Asn Arg
                325                 330                 335

Asp Lys Ile Leu Ala Val Ser Gln Ser Asp Asp Asp Thr Val Ile Gln
                340                 345                 350

Phe Cys Ala Met His Ile Phe Val Lys Glu Leu Glu
            355                 360

<210> SEQ ID NO 47
<211> LENGTH: 381
<212> TYPE: PRT
<213> ORGANISM: Artificial Sequence
<220> FEATURE:
<223> OTHER INFORMATION: Description of Artificial Sequence:  Consensus
      sequence for TERT protein
<220> FEATURE:
<221> NAME/KEY: VARIANT
<222> LOCATION: (1)..(369)
<223> OTHER INFORMATION: X at positions 1, 5- 7, 11, 13, 14, 19, 21-23,
      26, 31, 34, 39, 40, 44, 60, 62, 66, 74, 80, 92, 96, 109-113, 120,
      123, 124, 126, 129, 132, 133, 135, 137, 148, 158 = any naturally
      occurring amino acid.
<220> FEATURE:
<221> NAME/KEY: VARIANT
<222> LOCATION: (1)..(369)
<223> OTHER INFORMATION: X at positions 160, 168, 173, 175, 178, 181,
      184, 187, 190, 197-203, 206, 209-211, 219, 220, 223, 227, 239,
      245, 255, 256, 259, 260, 262, 265, 274, 275, 279, 302, 306, 313 =
      any naturally occurring amino acid.
<220> FEATURE:
<221> NAME/KEY: VARIANT
<222> LOCATION: (1)..(369)
<223> OTHER INFORMATION: X at positions 327-327, 334, 337, 342, 344-346,
      354, 363, 364, 366, 369 = any naturally occurring amino acid.

<400> SEQUENCE: 47

Xaa Leu Leu Lys Xaa Xaa Xaa Cys Pro Leu Xaa Glu Xaa Xaa Leu Leu
 1                   5                  10                  15

Ser Tyr Xaa Ser Xaa Xaa Xaa Gln Val Xaa Asn Phe Leu Arg Xaa Ile
                20                  25                  30

Leu Xaa Lys Leu Val Pro Xaa Xaa Leu Trp Gly Xaa Arg His Asn Lys
        35                  40                  45

Lys Ile Phe Leu Lys Asn Leu Lys Lys Phe Leu Xaa Leu Xaa Lys Tyr
    50                  55                  60

Glu Xaa Leu Ser Leu Gln Glu Leu Met Xaa Lys Ile Lys Val Arg Xaa
65                  70                  75                  80

Ile Leu Ala Lys Phe Leu Phe Trp Leu Phe Asp Xaa Leu Val Val Xaa
                85                  90                  95
```

-continued

```
Leu Leu Arg Ser Phe Phe Tyr Ile Thr Glu Thr Thr Xaa Xaa Xaa Xaa
            100                 105                 110

Xaa Leu Phe Tyr Tyr Arg Lys Xaa Ile Trp Xaa Xaa Leu Xaa Arg Ile
        115                 120                 125

Xaa Phe Ile Xaa Xaa Leu Xaa Lys Xaa Leu Arg Glu Leu Gln Glu Lys
    130                 135                 140

Glu Val Arg Xaa Gly Lys Leu Arg Leu Ile Pro Lys Lys Xaa Thr Xaa
145                 150                 155                 160

Phe Arg Pro Ile Val Asn Met Xaa Arg Lys Val Val Xaa Arg Xaa Leu
                165                 170                 175

Lys Xaa Met Thr Xaa Asn Gln Xaa Leu Val Xaa Thr Leu Xaa Met Leu
        180                 185                 190

Lys Asn Leu Lys Xaa Xaa Xaa Xaa Xaa Xaa Leu Gly Xaa Ser Val
        195                 200                 205

Xaa Xaa Xaa Asp Asp Ile Met Arg Arg Trp Xaa Xaa Phe Val Xaa Lys
    210                 215                 220

Trp Arg Xaa Pro Lys Leu Tyr Phe Val Lys Val Asp Ile Lys Xaa Cys
225                 230                 235                 240

Tyr Asp Thr Ile Xaa Gln Asp Arg Leu Val Arg Val Leu Lys Xaa Xaa
                245                 250                 255

Ile Lys Xaa Xaa Glu Xaa Ser Leu Xaa Arg Asp Ser Val Val Ile Glu
        260                 265                 270

Gln Xaa Xaa Tyr Lys Gln Xaa Lys Gly Ile Pro Gln Gly Ser Ser Leu
    275                 280                 285

Ser Thr Ile Leu Cys Ser Leu Tyr Tyr Gly Asp Leu Glu Xaa Glu Glu
    290                 295                 300

Tyr Xaa Gln Phe Leu Arg Arg Asp Xaa Leu Leu Leu Arg Leu Val Asp
305                 310                 315                 320

Asp Phe Leu Leu Ile Thr Xaa Xaa Xaa Asn Asn Ala Lys Xaa Phe Leu
                325                 330                 335

Xaa Leu Leu Val Arg Xaa Gly Xaa Xaa Xaa Tyr Gly Phe Lys Val Asn
        340                 345                 350

Leu Xaa Lys Thr Val Val Asn Phe Gln Met Xaa Xaa His Xaa Leu Met
        355                 360                 365

Xaa Trp Ile Gly Leu Ser Ile Asp Ile Arg Thr Leu Glu
    370                 375                 380
```

<210> SEQ ID NO 48
<211> LENGTH: 271
<212> TYPE: DNA
<213> ORGANISM: Arabidopsis thaliana
<220> FEATURE:
<223> OTHER INFORMATION: Segment of TERT gene

<400> SEQUENCE: 48

```
ttactgagat ttattgatga ctacattttt gtgtctacct caagagatca ggcgagtagc    60
ttctatcaca ggttgaagca tggatttaaa gattacaact gcttcatgaa cgaaacaaaa   120
ttctgcataa attttgaaga taaagaagaa cataggtgtt cttataatag aatgtttgtg   180
ggcgataatg gagttccttt tgtcagatgg acgggtttgc ttattaattc ccgcacattt   240
gaagttcaag ttgactacac aaggtctgcc t                                  271
```

<210> SEQ ID NO 49
<211> LENGTH: 364
<212> TYPE: PRT
<213> ORGANISM: Candida albicans

```
<220> FEATURE:
<223> OTHER INFORMATION: Partial TERT sequence

<400> SEQUENCE: 49

Lys Phe Ile Gly Thr Lys Cys Asn Phe Ala Asn Asn Val Val Ser Asn
  1               5                  10                  15

Lys Thr Glu Ile Ser Gln Val Ile Gln Phe Val Leu Leu Val Leu Gly
             20                  25                  30

Lys Leu Leu Pro Leu Asp Ala Trp Gly Val Ser Asn Asn Lys Ile Ile
             35                  40                  45

Lys Asp Arg Val Val Asp Phe Leu Leu Leu Gly Ala Asn Glu Lys Ile
         50                  55                  60

His Met Asp Asp Leu Phe Arg Gly Ile Arg Leu Lys Phe Leu Lys Gly
 65                  70                  75                  80

Tyr Leu Trp Trp Leu Phe Glu His Leu Leu Lys Asn Ile Leu Arg Ser
                 85                  90                  95

Phe Trp Tyr Ile Thr Glu Thr Ser Ser Ile Val Ser Leu Asn Tyr Phe
                100                 105                 110

Pro Gln Tyr Leu Trp Lys Glu Leu Tyr Glu Ser Trp Val Ser Lys Tyr
            115                 120                 125

Ala Lys Leu Val Lys Met Pro Ser Lys Ile Gln Arg Gly Lys Ile Lys
130                 135                 140

Leu Ile Pro Lys Arg Ser Ser Phe Arg Val Ile Cys Val Pro Ile Lys
145                 150                 155                 160

Arg Ser Leu Lys Leu Leu Asn Lys Leu Pro Val Gly Gln Ile Leu Arg
                165                 170                 175

Leu Lys Leu Ser Lys Leu Arg Asp Thr Tyr Glu Ser Tyr Arg Ala Ser
                180                 185                 190

Val His Ser Ser Asp Val Ala Glu Lys Ile Leu Asp Tyr Arg Asp
                195                 200                 205

Ser Leu Leu Thr Arg Leu Gly Pro Lys Leu Phe Ile Leu Lys Ser Asp
210                 215                 220

Met Lys Glu Cys Tyr Asp Arg Leu Ser Gln Pro Val Leu Met Lys Lys
225                 230                 235                 240

Leu Glu Glu Leu Phe Glu Asn Gln Asp Lys Ser Leu Val Asp Lys Thr
                245                 250                 255

Lys Thr Ile Ala Leu Tyr Lys Arg Lys Arg Gly Val Phe Gln Gly Phe
                260                 265                 270

Ser Leu Leu Ser Ile Phe Cys Asp Ile Leu Tyr Ser Ala Met Val His
                275                 280                 285

Asp Cys Phe Gln Phe Leu Trp Lys Ser Leu Phe Val Arg Leu Val Asp
        290                 295                 300

Asp Phe Leu Leu Val Thr Pro Asp Ser Asn Ile Tyr Asp Gln Val His
305                 310                 315                 320

Asn Ile Leu Ser Gly Ile Leu Glu Ser Tyr Gly Ala Phe Val Asn Lys
                325                 330                 335

Asp Lys Thr Val Val Asn Gln Thr Thr Lys Thr Ser Ile Asp
                340                 345                 350

Phe Val Gly Leu Glu Val Asn Thr Thr Asp Leu Ser
            355                 360
```

TELOMERASE REVERSE TRANSCRIPTASE (TERT) GENES FROM *CANDIDA ALBICANS*

FIELD OF THE INVENTION

The present invention pertains, in general, to the identification and use of Telomerase Reverse Transcriptase (TERT) genes and the proteins encoded by such genes. In particular, the present invention pertains to the identification and use of TERT genes and TERT proteins from several genetically diverse and economically important organisms, including two human pathogens and an agronomic crop species.

BACKGROUND OF THE INVENTION

All publications and patent applications herein are incorporated by reference to the same extent as if each individual publication or patent application was specifically and individually indicated to be incorporated by reference.

TERT genes have been identified in mammals (mouse and human), yeasts (*Saccharomyces cerevisiae, Schizosaccharomyces pombe*) and ciliated protozoans (*Tetrahymena thermophila, Oxytricha trifallax* and *Euplotes aediculatus*) (Ligner, J. et al., 1997; Bryan, T. M. et al., 1998; Nakamura, T. M. at al., 1997; Greenberg, R. A. et al., 1999). Telomerase RNA has been cloned from bovine testis (Tsao et al., 1998) and from approximately twenty other organisms.

The protein encoded by the TERT gene, together with an RNA subunit, comprise telomerase, an enzyme required for the maintenance of telomeres. Telomeres, which are long stretches of short DNA sequence repeats located on the ends of linear chromosomes, are an essential component of the eukaryotic genome. They serve as "caps" on chromosomal termini, preventing loss of terminal sequence information and degradation of chromosomal DNA, as well as regulating expression of nearby genes. Telomerase has been shown to be responsible for maintenance of telomere length, as cells lacking this enzyme experience a shortening and eventual loss of telomeric sequence. For a recent review, see Bryan and Cech, 1999.

Telomere length and telomerase activity have been implicated in studies of both aging and cancer. Telomeres are believed to function as a molecular clock, gradually shortening as a cell ages and signaling cell death when the telomeres decay down to a critical length. It has been observed that in many immortal cells, telomerase appears to be overactive, resulting in telomeres that are maintained indefinitely. These observations have led to great interest in research programs attempting to develop pharmaceuticals that either ameliorate or activate telomerase activity, as well as diagnostic tools to detect telomerase activity. For reviews, see Raymond, 1996 and Holt and Shay, 1999.

We have identified TERT genes from three economically important and genetically diverse organisms: *Plasmodium falciparum, Candida albicans* and *Oryza sativa. P. falciparum* and *C. albicans* are the causative agents of serious medical conditions of humans while *O. sativa* is food staple of people throughout the world, especially those of third world countries. The discovery of these genes will have a profound effect on our ability to genetically manipulate and control the growth of these important organisms.

SUMMARY OF THE INVENTION

This invention comprises compositions and methods for the identification and use of novel TERT genes. In particular, this invention provides comprises compositions and methods for the identification and use of TERT genes of *Plasmodium falciparum, Candida albicans* and *Oryza sativa*.

The present invention provides isolated nucleic acid molecules coding for TERT genes and TERT gene fragments wherein the isolated nucleic acid molecules include: (a) isolated nucleic acid molecules that encode the amino acid sequence of SEQ ID NO.2, SEQ ID NO.4, SEQ ID NO.6, SEQ ID NO.8 or SEQ ID NO.10; (b) isolated nucleic acid molecules that encode a fragment of at least 6 amino acids of SEQ ID NO.2, SEQ ID NO.4, SEQ ID NO.6, SEQ ID NO.8 or SEQ ID NO.10; (c) isolated nucleic acid molecules which hybridize to the complement of a nucleic acid molecule comprising SEQ ID NO.1, SEQ ID NO.3, SEQ ID NO.5, SEQ ID NO.7 or SEQ ID NO.9 under conditions of sufficient stringency to produce a clear signal; and (d) isolated nucleic acid molecules which hybridize to a nucleic acid molecule that encodes the amino acid sequence of SEQ ID NO.2, SEQ ID NO.4, SEQ ID NO.6, SEQ ID NO.8 or SEQ ID NO.10 under conditions of sufficient stringency to produce a clear signal. In particular, this invention provides nucleic acid molecules with the nucleic acid sequences of SEQ ID NO.1, SEQ ID NO.3, SEQ ID NO.5, SEQ ID NO.7 and SEQ ID NO.9.

This invention also provides such isolated nucleic acid molecules coding for TERT genes or gene fragments operably linked to one or more expression control elements.

This invention also provides vectors comprising such isolated nucleic acid molecules coding for TERT genes and TERT gene fragments.

This invention also provides host cells, tissues, organs and organisms transformed to contain such nucleic acid molecules coding for TERT genes and TERT gene fragments. This invention further provides host cells, tissues, organs and organisms comprising vectors comprising such isolated nucleic acid molecules coding for TERT genes and TERT gene fragments.

This invention also provides methods for producing a polypeptide comprising the step of culturing a host cell transformed with such nucleic acid molecules coding for TERT genes and gene fragments under conditions in which the protein encoded by these nucleic acid molecules are expressed. This invention further provides isolated polypeptides produced by such methods.

This invention also provides isolated TERT polypeptides and TERT polypeptide fragments wherein the polypeptides include: (a) those coded by the amino acid sequence of SEQ ID NO.2, SEQ ID NO.4, SEQ ID NO.6, SEQ ID NO.8 or SEQ ID NO.10; (b) those comprising a fragment of at least 6 amino acids of SEQ ID NO.2, SEQ ID NO.4, SEQ ID NO.6, SEQ ID NO.8 or SEQ ID NO.10; (c) conservative amino acid substitutions of SEQ ID NO.2, SEQ ID NO.4, SEQ ID NO.6, SEQ ID NO.8 or SEQ ID NO.10; and (d) naturally occurring amino acid sequence variants of SEQ ID NO.2, SEQ ID NO.4, SEQ ID NO.6, SEQ ID NO.8 or SEQ ID NO.10.

The invention also provides isolated antibodies that bind to such TERT polypeptides and TERT polypeptide fragments. The invention further provides such antibodies wherein the antibodies are monoclonal or polyclonal antibodies.

The invention also provides methods of identifying an agents which modulate the expression of a nucleic acid encoding the protein having the sequence of SEQ ID NO.2, SEQ ID NO.4, SEQ ID NO.6, SEQ ID NO.8 or SEQ ID NO.10 comprising the steps of:

exposing cells which express the nucleic acid to the agent; and determining whether the agent modulates expression of said nucleic acid, thereby identifying an agent which modulates the expression of a nucleic acid encoding the protein having the sequence of SEQ ID NO.2, SEQ ID NO.4, SEQ ID NO.6, SEQ ID NO.8 or SEQ ID NO.10.

The invention also provides methods of identifying agents which modulate at least one activity of a protein comprising the sequence of SEQ ID NO.2, SEQ ID NO.4, SEQ ID NO.6, SEQ ID NO.8 or SEQ ID NO.10 comprising the steps of:

exposing cells which express the protein to the agent;

determining whether the agent modulates at least one activity of said protein, thereby identifying an agent which modulates at least one activity of a protein comprising the sequence of SEQ ID NO.2, SEQ ID NO.4, SEQ ID NO.6, SEQ ID NO.8 or SEQ ID NO.10.

The invention also provides methods of identifying binding partners for a protein comprising the sequence of SEQ ID NO.2, SEQ ID NO.4, SEQ ID NO.6, SEQ ID NO.8 or SEQ ID NO.10, comprising the steps of:

exposing said protein to a potential binding partner; and determining if the potential binding partner binds to said protein, thereby identifying binding partners for a protein comprising the sequence of SEQ ID NO.2, SEQ ID NO.4, SEQ ID NO.6, SEQ ID NO.8 or SEQ ID NO.10.

The invention also provides methods of modulating the expression of a nucleic acid encoding the protein having the sequence of SEQ ID NO.2, SEQ ID NO.4, SEQ ID NO.6, SEQ ID NO.8 or SEQ ID NO.10 comprising the step of:

administering an effective amount of an agent which modulates the expression of a nucleic acid encoding the protein having the sequence of SEQ ID NO.2, SEQ ID NO.4, SEQ ID NO.6, SEQ ID NO.8 or SEQ ID NO.10.

This invention also provides methods of modulating at least one activity of a protein comprising the sequence of SEQ ID NO.2, SEQ ID NO.4, SEQ ID NO.6, SEQ ID NO.8 or SEQ ID NO.10 comprising the step of:

administering an effective amount of an agent which modulates at least one activity of a protein comprising the sequence of SEQ ID NO.2, SEQ ID NO.4, SEQ ID NO.6, SEQ ID NO.8 or SEQ ID NO.10.

This invention also provides methods for diagnosing *Plasmodium falciparum* infection in a patient comprising the steps of:

obtaining a cell sample from the patient;

determining whether the nucleic acid of SEQ ID NO.5 or SEQ ID NO.7 or the protein of SEQ ID NO.6 or SEQ ID NO.8 is present within the cell sample; and correlating the presence of the nucleic acid of SEQ ID NO.5 or SEQ ID NO.7 or the protein of SEQ ID NO.6 or SEQ ID NO.8 with the presence of *Plasmodium falciparum*.

This invention also provides methods for diagnosing *Candida albicans* infection in a patient comprising the steps of:

obtaining a cell sample from the patient;

determining whether the nucleic acid of SEQ ID NO.1 or SEQ ID NO.3 or the protein of SEQ ID NO.2 or SEQ ID NO.4 is present within the cell sample; and correlating the presence of the nucleic acid of SEQ ID NO.1 or SEQ ID NO.3 or the protein of SEQ ID NO.2 or SEQ ID NO.4 with the presence of *Candida albicans*.

One skilled in the art can easily make any necessary adjustments in accordance with the necessities of the particular situation.

Further objects and advantages of the present invention will be clear from the description that follows.

BRIEF DESCRIPTION OF THE DRAWINGS

FIG. 1. Identification of the TERT gene for *P. falciparum*.
① Sanger Centre chromosome 13 contig 41294.
② Sanger Centre chromosome 13 contig 02431.
③ TIGR Database chromosome 14 contig 5560 (now #364).
④ *P. falciparum* Putative Telomerase Gene. Letters indicate motifs.

FIG. 2. Sequence alignment of the *P. falciparum* TERT gene and the TERT genes of other organisms. Organism codes are as follows:
h.=Human (SEQ ID NO: 40).
m.=Mouse (SEQ ID NO: 41).
o.=*Oxytricha trifallax* (SEQ ID NO: 42).
E.=*Euplotes aediculatus* (SEQ ID NO: 43).
T.=*Tetrahymena thermophila* (SEQ ID NO: 44).
Sp.=*Schizosaccharomyces pombe* (SEQ ID NO: 45).
Sc.=*Saccharomyces cerevisiae* (SEQ ID NO: 46).
Ca.=*Candida albicans* (SEQ ID NO: 49). The consensus sequence (SEQ ID NO:47) appears as the last line in this set of compared sequences.

Lane 6 No template control. All other conditions as in Lane 4.

Figure 5:
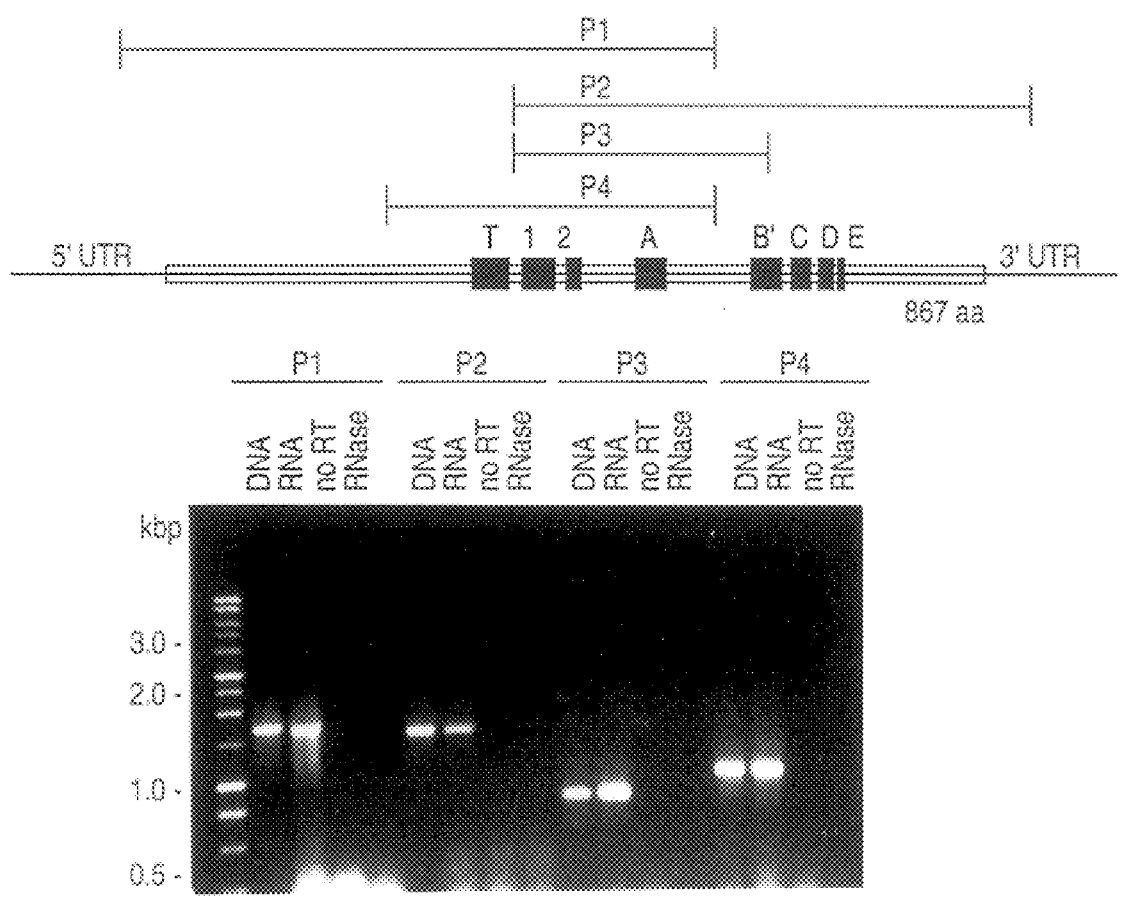

FIG. 5. TERT RT-PCR Gel on Total RNA of *C. albicans*.

Product 1 (P1) was amplified with RT3 and FOR1; product 2 (P2) with RT1 and FOR2; product 3 (P3) with RT2 and FOR2; and product 4 (P4) with RT3 and FOR3.

Figure 4:
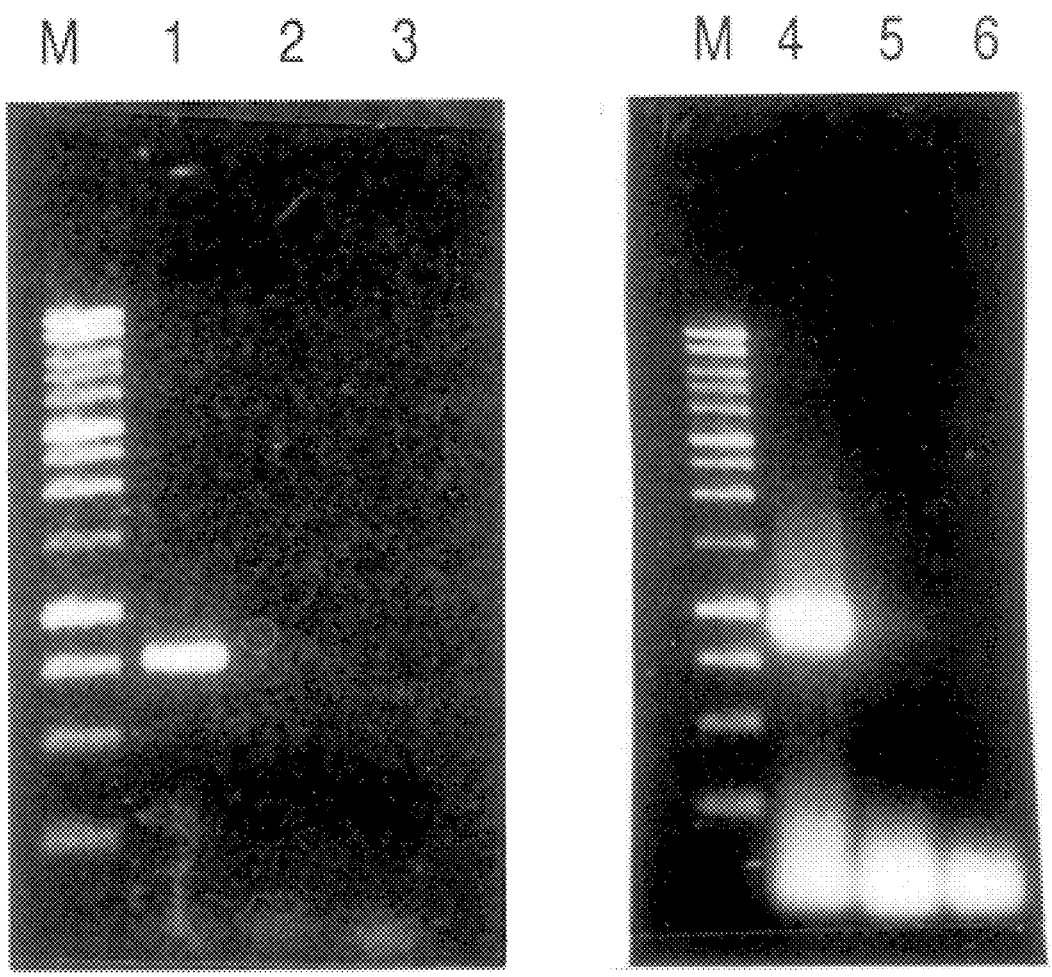
FIG. 4. TERT RT-PCR Gel on Total RNA of *C. albicans*.
Lane 1 RT PCR on 5 µg *Candida albicans* total RNA with primers CaFor2 and CaRT2 (45 min at 48 C. followed by 40 cycles of 1 min at 94 C., 1 min at 52 C., 2 min at 68 C.). Nested PCR of 3 µl product (20 cycles of 1 min at 94 C., 1 min at 52 C., 4 min at 68 C.) with primers CaFor2 and CaNest2. 1 µl sample loaded on 0.8% agarose gel.
Lane 2 No AMV-reverse transcriptase control. All other conditions as in Lane 1.
Lane 3 No template control. All other conditions as in Lane 1.
Lane 4 RT PCR on 0.85 µg *Candida albicans* total RNA with primers CaRT3 and CaFor3 (45 min at 48 C. followed by 40 cycles of 1 min at 94 C., 1 min at 52 C., 2 min at 68 C.). 10 µl product electrophoresed on 0.8% agarose gel.
Lane 5 No AMV-reverse transcriptase control. All other conditions as in Lane 4.

Products 2 and 4 were not visible on agarose gel after 40 cycles, and 3 μl PCR product was reamplified with NEST1 and FOR2 (P2) or NEST2 and FOR2 (P4) for another 12 cycles of PCR as described for FIG. 4.

FIG. 6. Sequence alignment of the i O. sativa(SEQ ID NO: 9) TERT gene and the *Arabidopsis thaliana* (SEQ ID NO: 48) TERT genes.

DETAILED DESCRIPTION OF THE INVENTION

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

Definitions

"Allele" or "allelomorph" refers to any of the forms of the same gene that occur at the same locus on a homologous chromosome but differ in base sequence. Two or more alleles are said to be allelic or allelomorphic to each other, and if more than two alleles exist in a population, the locus is said to show multiple allelism.

"Apoptosis" refers to cell death that may occur by accident, cell necrosis, or by an intracellular controlled process characterized by a condensation and, subsequent, fragmentation of the cell nucleus during which the plasma membrane remains intact.

"Modulate" refers to the inhibition, induction, agonism and/or antagonism of the expression or function of a TERT gene or TERT gene product.

"Nucleic acid" includes DNA and RNA molecules and is used synonymously with the terms "nucleic acid sequence" and "polynucleotide."

"Polypeptide" refers to an amino acid sequence including, but not limited to, proteins and protein fragments, naturally derived or synthetically produced.

"Senescence" refers to the process of growing old or aging.

"Telomerase" refers to a ribonucleoprotein, telomere specific reverse transcriptase, which contains some protein components and telomerase RNA components. Telomerase can synthesize the tandem repeat units of telomere to the 3' end of telomeric primers without a template. The RNA component of the enzyme contains the complementary sequence of the telomeric repeats it synthesizes.

"Telomere-specific repeats" refers to simple DNA repeat sequences found at the ends of chromosomes. These sequences are sometimes referred to as "telomeric DNA" by those skilled in the art.

"Telomerase enzyme subunit" refers to any domain, or region or discrete part of a polypeptide sequence that can be equated with telomerase enzyme function.

"Telomere" refers to the specialized DNA sequence found at the end of the chromosome that provides stability to the chromosome, prevents fusion with other natural or broken ends, and allows replication without loss.

"TERT" refers to Telomerase Reverse Transcriptase. TERT, as it is used herein, can refer to either the gene encoding the enzyme or to the enzyme (i.e., protein) itself. TERT refers to the nucleoprotein, or enzyme, portion of telomerase. TERT genes have also been called "Ever Shorter Telomeres" or "EST" genes.

"Transcriptional factors" refers to a class of proteins that bind to a promoter or to a nearby sequence of DNA to facilitate or prevent transcription initiation.

"Transcriptional profiling" refers to any assay method or technique which is capable of analyzing, quantitatively and/or qualitatively, one or more mRNA species found in a cell or a nucleic acid sample. For example, such assays include, but are not limited to, RT-PCR, quantitative PCR (Q-PCR), RNase protection assays, subtractive hybridization, READS and Northern blots.

Overview of the Invention

The present invention is based in part on the identification of new TERT genes and the TERT proteins encoded by these genes found in three economically important organisms.

The newly identified TERT proteins can serve as targets for agents that can be used to modulate the expression or activity of the enzyme. For example, agents may be identified which modulate biological processes associated with telomerase, such as but not limited to: the maintenance of telomeres, replicative senescence, cell multiplication, mitotic clock functioning, aging, proliferative capacity, tumorigenesis, tumor progression, cellular immortilization, cellular senescence, apoptosis and cell death.

Agents identified by the methods of the present invention can inhibit or promote the growth of specific organisms by modulating the expression or activity of the TERT proteins specific to the organisms. Thus, agents can be identified which are useful in the prevention, treatment or eradication of infection by pathogens, including infection by parasitic protozoans and pathogenic yeasts. Agents may also be identified which modulate the biological processes associated with recovery from various types of cancer.

Agents identified by the methods of the present invention can modulate the biological processes of plants, thereby controlling plant growth ability and rate. The agents identified by the methods of the present invention can be used in various agricultural chemicals, including growth regulators, herbicides and fertilizers.

The present invention is further based on the development of methods for isolating binding partners that bind to the TERT proteins. Probes based on the proteins are used as capture probes to isolate potential binding partners, such as other proteins. Dominant negative proteins, DNAs encoding these proteins, antibodies to these proteins, peptide fragments of these proteins or mimics of these proteins may be introduced into cells to affect function. Additionally, these proteins provide a novel target for screening of synthetic small molecules and combinatorial or naturally occurring compound libraries to discover novel therapeutics to regulate various cellular processes or diseases such as cell cycle, cell death and tumor progression.

*Plasmodium falciparum* TERT Gene and TERT Protein

We have identified a TERT gene from the parasite *Plasmodium falciparum* and performed experiments that indicate that the TERT gene product is expressed in vivo. This is the first identification of this essential gene and protein in this important human pathogen.

*P. falciparum* is a protozoan which is the causative agent of malaria. Malaria is the world's most important tropical parasitic disease, presenting 300–500 million clinical cases per year and causing over 1 million deaths per year (WHO, 1998). Thus, identification of the TERT gene product from Plasmodium, which is a vital component of cell viability, is an important contribution to research towards eradication of this disease.

Our discovery of the TERT gene and TERT protein of *Plasmodium falciparum* makes possible avenues of research aimed at understanding the structure and function of the TERT gene and its effects on the Plasmodium life cycle and pathogenicity. Possible utility includes but is not limited to development of natural or artificial compounds that affect TERT activity, or screening procedures to aid in detection of this pathogen.

*Candida albicans* TERT Genes and TERT Proteins

We have identified TERT genes and TERT proteins from the yeast *Candida albicans,* and performed experiments that indicate that the TERT gene product is expressed in vivo. This is the first identification of these essential genes and proteins in this important human pathogen. The *C. albicans* proteins are the smallest TERT homologues discovered to date. Their compact size makes them an attractive target for gene analysis and for protein crystallization.

*C. albicans* is the cause of vaginal candidiasis (commonly known as yeast infections) in women. Additionally, Candida can cause severe, life threatening infections in the respiratory tract and major organs of immunocompromised patients, such as persons suffering from HIV disease, patients undergoing immunosuppresive therapy or the elderly (McCullough et al., 1996). Thus, identification of the TERT genes and TERT proteins from Candida, which is a vital component of cell viability, is an important contribution to research towards eradication of disease caused by this pathogen.

Our discovery of the TERT genes and TERT proteins of *Candida albicans* makes possible avenues of research aimed at understanding the structure and function of the TERT genes and its effects on the *C. albicans* life cycle and pathogenicity. Possible utility includes but is not limited to development of natural or artificial compounds that affect TERT activity, or screening procedures to aid in detection of this pathogen.

The National Institutes of Health is currently researching fungal virulence genes using a gene disruption approach. At least four *C. albicans* genes involved in human pathogenicity have been identified by this method to date (Kwon-Chun, 1998). The identification of the TERT genes thus makes possible studies to determine the effects of these genes on the pathogenicity of the organism. Similar studies of the function of the TERT gene/catalytic subunit of the TERT protein have been carried out in the ciliate *Euplotes aediculatus* and in the fission yeast *Schizosaccharomyces pombe* (Nakamura et al., 1997).

*Oryza sativa* TERT Gene Fragment and TERT Protein Fragment

We have identified a TERT gene fragment and TERT protein fragment from rice, *Oryza sativa.* This is the first identification of a fragment of this essential gene in an important crop plant.

Our discovery of the TERT gene fragment of *O. sativa* makes possible avenues of research aimed at understanding the structure and function of the TERT gene and its effects on the life cycle of the rice plant. Potential interest in this discovery include implications for plant cell proliferative capacity by, for example, by down-regulating telomerase expression (i.e., prevent growth of roots and flowers in weeds) or by up-regulating telomerase expression leading to a larger endosperm and thus improved grain yield.

Telomeres and Telomerase

Telomeres

A large fraction of the deoxyribonucleic acid (DNA) of most higher eukaryotes is made up of repeat sequences ranging from a few copies up to millions of copies. Repeat functional sequences occur at the telomeres and centromeres of eukaryotic chromosomes.

Telomeres are specialized DNA sequences found at the ends of the chromosomes of eukaryotes which function in chromosome protection, positioning, and replication. Telomeres protect linear chromosomes from degradation and fusion to other chromosomes, and are thought to be a site of attachment to the nuclear matrix at times during the cell cycle. As chromosome caps they reduce the formation of damaged and rearranged chromosomes which arise as a consequence of recombination-mediated chromosome fusion events.

Generally, telomeres consist of tens to thousands of tandem repeats of a telomere motif sequence and associated proteins. The telomeres from all species show the same pattern: a short DNA sequence, one strand G-rich and one C-rich, that is tandemly repeated many times. The repeating telomeric unit found in Tetrahymena is $T_2G_4$, in the ciliated protozoan Oxytricha it is $T_4G_4$, and in *Saccharomyces cerevisiae* it is $T_{1-3}G_{1-3}$. In humans and other mammals this motif is 5'-d(TTAGGG)-3'. Sequences specific to other species such as plants may be found in Greider et al. (1990).

Telomeres of all human chromosomes are composed of variable length arrays of the TTAGGG repeat units with the G-rich strand oriented 5' to 3' towards the telomere. Variant telomere repeat units such as TTGGGG and TGAGGG have been identified but tend to be located at the proximal ends of human telomeres. Methods for detecting and quantitating multiple copies of a repeat sequence, such as a telomere (or centromere) repeat sequence, are provided in WO 97/14026. Methods for characterizing variability in telomere DNA by Polymerase Chain Reaction (PCR) are provided in WO 96/12821.

Telomerase

The maintenance of telomeres is required for cells to avoid replicative senescence and to continue to multiply. Chromosomes lose about 50–200 nucleotides of telomeric sequence from their ends per cell division, and the shortening of telomeres may act as a mitotic clock shortening with age both in vitro and in vivo in a replication dependent manner (Harley, 1991). Telomeric sequences can be added back to the chromosome ends, by telomere terminal transferase, also known as telomerase enzyme or simply as telomerase. Methods and compositions for increasing telomere length in normal cells to increase the proliferative capacity of cells and to delay the onset of senescence are provided in U.S. Pat. No. 5,686,306.

Telomerase is a ribonucleoprotein enzyme that elongates the G-rich strand of chromosomal termini by adding telomeric repeats. This elongation occurs by reverse transcription of a part of the telomerase RNA component, which contains a sequence complementary to the telomere repeat. Following telomerase-catalyzed extension of the G-rich strand, the complementary DNA strand of the telomere is presumably replicated by more conventional means.

Telomerase is a reverse transcriptase composed of both ribonucleotide acid (RNA) and protein, wherein the RNA molecule functions as the template for the telomeric repeat. The RNA moiety of human telomerase contains the 5'-CCCTAA-3' sequence that may act as the template for de novo synthesis. The enzyme also contains a region that recognizes the guanine rich single strands of a DNA substrate. Methods and compositions for the determination of telomere length and telomerase activity are provided in U.S. Pat. Nos. 5,489,508 and 5,707,795.

The RNA component of the telomerase enzymes of *Saccharomyces cerevisiae,* certain species of Tetrahymena, as well as that of other ciliates, such as Euplotes and Glaucoma, has been sequenced and reported in the scientific literature. See Singer and Gottschling, Oct. 21, 1994, Science 266:404–409; Lingner et al., 1994, Genes & Development 8:1984–1988; Greider and Blackburn, 1989, Nature 337:331–337; Romero and Blackburn, 1991, Cell 67:343–353; and Shippen-Lentz and Blackburn, 1990, Science 247:546–552; and U.S. Pat. No. 5,698,686, each of which is incorporated herein by reference.

The telomerase enzymes of these ciliates synthesize telomeric repeat units distinct from that in mammals. The nucleic acids comprising the RNA of a mammalian telomerase are provided in U.S. Pat. No. 5,583,016.

The functioning of telomerases seems to be activated in dividing embryonic cells and gametocytes. Telomerase activity has been identified in germ line cells and tumor cells but is repressed in differentiated somatic cells. It is now believed that the reactivation of telomerase is an essential step in tumor progression and in the immortalization of cells in culture. It is postulated that inhibition of telomerase in an immortalized cell line or in the malignant condition would cause senescence or cell death. The introduction of synthetic oligonucleotides which mimic telomere motifs has been shown to inhibit the proliferation of immortal cells or cells that express telomerase (U.S. Pat. No. 5,643,890). In fact, the single telomere motif TTAGGG exhibited greater cellular uptake and higher inhibition of proliferation than longer oligonucleotides. Methods for screening for agents which inhibit telomerase activity, including fungal telomerase activity, are provided in U.S. Pat. No. 5,645,986.

Comprehensive reviews of both telomeres and telomerase are provided in U.S. Pat. Nos. 5,643,890 and 5,707,795.

Telomere-Telomere Recombination

Telomere-telomere recombination provides an alternate pathway for telomere maintenance in at least some eukaryotes (Zakian, 1997). Wang et al. (1990) provided evidence for a telomere-telomere recombination process in yeast which involves a gene conversion event that requires little homology, occurs at or near the boundary of telomeric and non-telomeric DNA, and resembles the recombination process involved in bacteriophage T4 DNA replication.

Yeast cells which lack a functional est1 gene exhibit a continuous decline in the terminal $(G_{1-3} T)_n$ tract, a progressive increase in the frequency of chromosome loss, and a concomitant increase in the frequency of cell death (Lundblad et al., 1989). Although EST1 is not a catalytic component of telomerase (Cohn et al., 1995), the same phenotypes are produced by deleting the S. cerevisiae telomerase RNA gene, tlc1 (Singer and Gottschling, 1994). Although the majority of the cells in an EST1$^-$ culture die, late EST1$^-$ cultures give rise to derivatives that have survived the lethal consequences of the est1 mutation. By studying the survival of late cultures of S. cerevisiae cells, Lundblad et al. (1993) demonstrated that yeast cells have a RAD52-dependent bypass pathway by which cells can circumvent a defect in the EST1-mediated pathway for yeast telomere replication. Most of the surviving cells have very short telomeres but acquire long tandem arrays of subtelomeric repeats by gene conversion. The researchers concluded that "even when the primary pathway for telomer replication is defective, an alternative backup pathway exists that restores sufficient telomere function for continued cell viability."

Although deletion of the telomerase RNA gene, ter1, in the yeast Kluyveromyces lactis also results in the gradual loss of telomeric repeats and progressively declining cell growth capability, some cells are able to continuing growing without telomerase. McEachern et al. (1996) proposed that shortened, terminal telomeric repeat tracts become uncapped, promoting recombinational repair between them to regenerate lengthened telomeres in survivors. They termed this process telomere cap-prevented recombination (CPR).

The TERT Proteins of the Present Invention

The present invention provides isolated proteins, allelic variants of the proteins, and conservative amino acid substitutions of the proteins. As used herein, the proteins or polypeptides refers to a protein that has the amino acid sequence depicted in SEQ ID NO.2, SEQ ID NO.4, SEQ ID NO.6, SEQ ID NO.8 or SEQ ID NO.10. The invention includes naturally occurring allelic variants and proteins that have a slightly different amino acid sequence than that specifically recited for SEQ ID NO.2, SEQ ID NO.4, SEQ ID NO.6, SEQ ID NO.8 or SEQ ID NO.10. Allelic variants, though possessing a slightly different amino acid sequence than those recited above, will still have the same or similar biological functions associated with the TERT proteins specifically identified herein.

As used herein, the family of proteins related to the TERT proteins of SEQ ID NO.2, SEQ ID NO.4, SEQ ID NO.6, SEQ ID NO.8 or SEQ ID NO.10 refer to proteins that have been isolated from organisms in addition to P. falciparum, C. albicans or O. sativa, wherein such proteins display unique features associated with the proteins of the present invention. The methods used to identify and isolate other members of protein families related to each of the TERT proteins of the present invention are described below.

The proteins of the present invention are preferably in isolated form. As used herein, a protein is said to be isolated when physical, mechanical or chemical methods are employed to remove the protein from cellular constituents that are normally associated with the protein. A skilled artisan can readily employ standard purification methods to obtain an isolated protein.

The proteins of the present invention further include conservative variants of the proteins herein described. As used herein, a conservative variant refers to alterations in the amino acid sequence that do not adversely affect the biological functions of the protein. A substitution, insertion or deletion is said to adversely affect the protein when the altered sequence prevents or disrupts a biological function associated with the protein. For example, the overall charge, structure or hydrophobic/hydrophilic properties of the protein can be altered without adversely affecting a biological activity. Accordingly, the amino acid sequence can be altered, for example to render the peptide more hydrophobic or hydrophilic, without adversely affecting the biological activities of the protein. Ordinarily, the allelic variants, the conservative substitution variants, and the members of the protein family will have an amino acid sequence having at least 30% amino acid sequence identity with the sequences set forth in SEQ ID NO.2, SEQ ID NO.4, SEQ ID NO.6, SEQ ID NO.8 or SEQ ID NO.10, or at least 35%, or at least 40%, or at least 45%, or at least 50%, or at least 55%, or at least 60%, or at least 65%, or at least 70%, or at least 75%, preferably at least 80%, or more preferably at least 85%, even more preferably at least 90%, and most preferably at least 95%. Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity. In a related aspect, conservative substitution refers to a substitution of one amino acid for another with generally similar properties (size, hydrophobicity, charge, etc). N-terminal, C-terminal or internal extensions, deletions, or insertions into the peptide sequence shall not be construed as affecting homology.

Thus, the proteins of the present invention include molecules having the amino acid sequence disclosed in SEQ ID NO.2, SEQ ID NO.4, SEQ ID NO.6, SEQ ID NO.8 or SEQ ID NO.10; fragments thereof having a consecutive sequence of at least about 3, 4, 5, 6, 10, 15, 20, 25, 30, 35 or more amino acid residues of the newly identified TERT proteins; amino acid sequence variants of such sequence wherein an amino acid residue has been inserted N- or C-terminal to, or within, the disclosed sequence; and amino acid sequence variants of the disclosed sequence, or their fragments as defined above, that have been substituted by another residue. Contemplated variants further include those containing predetermined mutations by, e.g., homologous recombination, site-directed or PCR mutagenesis, and the corresponding TERT proteins of other eukaryotic species, and the alleles or other naturally occurring variants of the families of TERT proteins; and derivatives wherein the TERT proteins have been covalently modified by substitution, chemical, enzymatic, or other appropriate means with a moiety other than a naturally occurring amino acid (for example a detectable moiety such as an enzyme or radioisotope).

As described below, members of the families of TERT proteins can be used: 1) to identify agents which modulate at least one activity of the TERT proteins; 2) in methods of identifying binding partners for the TERT proteins, 3) as antigens to raise polyclonal or monoclonal antibodies, and 4) as therapeutic agents.

TERT Nucleic Acid Molecules of the Present Invention

The present invention further provides nucleic acid molecules that encode the proteins having SEQ ID NO.2, SEQ ID NO.4, SEQ ID NO.6, SEQ ID NO.8 or SEQ ID NO.10 and the related proteins herein described, preferably in isolated form. As used herein, "nucleic acid" is defined as RNA or DNA that encodes a protein or peptide as defined above, or is complementary to nucleic acid sequence encoding such peptides, or hybridizes to such nucleic acids and remains stably bound to it under appropriate stringency conditions, or encodes polypeptides sharing at least 30% sequence identity, or at least 35%, or at least 40%, or at least 45%, or at least 50%, or at least 55%, or at least 60%, or at least 65%, or at least 70%, or at least 75%, preferably at least 80%, or more preferably at least 85%, even more preferably at least 90%, and most preferably at least 95%, with the TERT peptide sequences. Specifically contemplated are genomic DNA, cDNA, mRNA and antisense molecules, as well as nucleic acids based on alternative backbones or including alternative bases whether derived from natural sources or synthesized. Such hybridizing or complementary nucleic acids, however, are defined further as being novel and unobvious over any prior art nucleic acid including that which encodes, hybridizes under appropriate stringency conditions, or is complementary to nucleic acid encoding a protein according to the present invention.

Homology or identity is determined by BLAST (Basic Local Alignment Search Tool) analysis using the algorithm employed by the programs blastp, blastn, blastx, tblastn and tblastx (Karlin, et al., *Proc Natl Acad Sci USA* 87: 2264–2268, 1990 and Altschul, S. F., *J Mol Evol* 36: 290–300, 1993, fully incorporated by reference) which are tailored for sequence similarity searching. The approach used by the BLAST program is to first consider similar segments between a query sequence and a database sequence, then to evaluate the statistical significance of all matches that are identified and finally to summarize only those matches which satisfy a preselected threshold of significance. For a discussion of basic issues in similarity searching of sequence databases, see Altschul et al. (*Nature Genetics* 6: 119–129, 1994) which is fully incorporated by reference. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff, et al., *Proc Natl Acad Sci USA* 89: 10915–10919, 1992 fully incorporated by reference). For blastn, the scoring matrix is set by the ratios of M (i.e., the reward score for a pair of matching residues) to N (i.e., the penalty score for mismatching residues), wherein the default values for M and N are 5 and −4, respectively.

"Stringent conditions" are those hybridization conditions that work for Southern blots: hybridization with 32P nick translated probe is done in 6×SSC, 5×Denhardt's solution, 0.5% SDS, 10 mM EDTA pH8, 100 mcg/ml sheared, denatured salmon sperm DNA at 65 C. Washes are at room temperature for 2×30 m in 2×SSC, 0.1% SDS, followed by 2×30 min at 65 C. in 0.1×SSC, 0.1% SDS.

These conditions work, for example, for both of the Candida genes discovered by the present invention. For other Candida strains this process will still successfully work at 60 C.

A skilled artisan can readily determine and vary the stringency conditions appropriately to obtain a clear and detectable hybridization signal. For example, sufficient stringency conditions are contemplated such that target (e.g., SEQ ID NO.1, SEQ ID NO.3, SEQ ID NO.5, SEQ ID NO.7 or SEQ ID NO.9) and closely related sequences can be distinguished and isolated (see Sambrook et al., *Molecular Cloning: A Laboratory Manual*, 2nd ed pp. 9.47–9.58; 11.1–11.19 and 11.45–11–57, Cold Spring Harbor Laboratory Press, Cold Spring Harbor, N.Y., 1989 and *Methods in Enzymology*, Vol.152, (Berger et al., eds), pp.399–407 and 620–622, Academic Press, Inc., New York 1987).

The present invention further provides synthetic polynucleotides which may be synthesized by well-known techniques as described in the technical literature. See, e.g., Carruthers et al., 1982, Cold Spring Harbor Symp. Quant. Biol. 47:411–418 and Adams et al., 1983, J. Am. Chem. Soc. 105:661. Double stranded DNA fragments may then be obtained either by synthesizing the complementary strand and annealing the strands together under appropriate conditions, or by adding the complementary strand using DNA polymerase with an appropriate primer sequence.

As used herein, a nucleic acid molecule is said to be "isolated" when the nucleic acid molecule is substantially separated from contaminant nucleic acid encoding other polypeptides from the source of nucleic acid.

The present invention further provides fragments of the encoding nucleic acid molecules. As used herein, a fragment of an encoding nucleic acid molecule refers to a small portion of the entire protein encoding sequence. The size of the fragment will be determined by the intended use. For example, if the fragment is chosen so as to encode an active portion of the proteins, the fragment will need to be large enough to encode the functional region(s) of the proteins. If the fragment is to be used as a nucleic acid probe or PCR primer, then the fragment length is chosen so as to obtain a relatively small number of false positives during probing/priming.

Fragments of the encoding nucleic acid molecules of the present invention (i.e., synthetic oligonucleotides) that are used as probes or specific primers for the polymerase chain reaction (PCR), or to synthesize gene sequences encoding proteins of the invention can easily be synthesized by chemical techniques, for example, the phosphotriester method of Matteucci, et al., (*J. Am. Chem. Soc.* 103:3185–3191, 1981) or using automated synthesis methods. In addition, larger DNA segments can readily be prepared by well known methods, such as synthesis of a group of oligonucleotides that define various modular segments of the gene, followed by ligation of oligonucleotides to build the complete modified gene.

The encoding nucleic acid molecules of the present invention may further be modified so as to contain a detectable label for diagnostic and probe purposes. A variety of such labels are known in the art and can readily be employed with the encoding molecules herein described. Suitable labels include, but are not limited to, biotin, radiolabeled nucleotides and the like. A skilled artisan can employ any of the art known labels to obtain a labeled encoding nucleic acid molecule.

Modifications to the primary structures themselves by deletion, addition, or alteration of the amino acids incorporated into the protein sequences during translation can be made without destroying the activity of the TERT proteins. Such substitutions or other alterations result in proteins having an amino acid sequence encoded by a nucleic acid falling within the contemplated scope of the present invention.

Isolation of Other Related Nucleic Acid Molecules

As described above, the identification of the TERT nucleic acid molecules having SEQ ID NO.1, SEQ ID NO.3, SEQ ID NO.5, SEQ ID NO.7 or SEQ ID NO.9 allows a skilled artisan to isolate nucleic acid molecules that encode other members of the protein families of each organism in addition to the specific sequences herein described. Further, the presently disclosed nucleic acid molecules allow a skilled artisan to isolate nucleic acid molecules that encode other members of the families of proteins in addition to the amino acid protein having SEQ ID NO.2, SEQ ID NO.4, SEQ ID NO.6, SEQ ID NO.8 or SEQ ID NO.10.

Essentially, a skilled artisan can readily use the amino acid sequence of SEQ ID NO.2, SEQ ID NO.4, SEQ ID NO.6, SEQ ID NO.8 or SEQ ID NO.10 to generate antibody probes to screen expression libraries prepared from appropriate cells. Typically, polyclonal antiserum from mammals such as rabbits immunized with the purified proteins (as described below) or monoclonal antibodies can be used to probe a cDNA or genomic expression library, such as lambda gt11 library, to obtain the appropriate coding sequence for other members of the protein families. The cloned cDNA sequence can be expressed as a fusion protein, expressed directly using its own control sequences, or expressed by constructions using control sequences appropriate to the particular host used for expression of the enzyme.

Alternately a portion of the coding sequences herein described can be synthesized and used as probes to retrieve DNA encoding a member of the protein families from any eukaryotic organism. Oligomers containing approximately 18–20 nucleotides (encoding about a 6–7 amino acid stretch) are prepared and used to screen genomic DNA or cDNA libraries to obtain hybridization under stringent conditions or conditions of sufficient stringency to eliminate an undue level of false positives.

Additionally, pairs of oligonucleotide primers can be prepared for use in a polymerase chain reaction (PCR) to selectively clone an encoding nucleic acid molecule. A PCR denature/anneal/extend cycle for using such PCR primers is well known in the art and can readily be adapted for use in isolating other encoding nucleic acid molecules.

Methods to Identify Pathogen Infection, Disease Progression and Success/Failure of Treatment U.S. Pat. No. 5,489,508 sets forth general methods useful for determining the telomere length and telomere activity of a cell based on elongating oligonucleotide primers that can serve as a substrate for telomerase-mediated primer extension under conditions which minimize interference from other genomic sequences. U.S. Pat. No. 5,695,932 sets forth telomerase activity assays for diagnosing pathogenic infections, including those of Candida and *P. falciparum.* These methods are based on detecting the telomeric nucleic acids particular to a specific pathogen. The telomeric nucleic acids utilized by these methods are the specific telomeric repeats which a particular telomerase adds to the ends of the chromosomes. The methods set forth in these patents do not directly utilize a TERT gene or a TERT protein specific to a pathogen.

TERT expression has been suggested as a useful marker in diagnosing human gastric carcinomas and bladder cancer (Yasui et al., 1998; Ito et al., 1998).

Until the present invention, the TERT genes and TERT proteins of *P. falciparum* and *C. albicans* were not available for use in methods which can more directly detect these pathogens.

Thus, another embodiment of the present invention provides methods for detecting the presence or absence of a pathogen in a cell, tissue, organ or organism by analyzing the cell, tissue, organ or organism for the TERT mRNA, TERT DNA or TERT protein particular to the pathogen of interest. The present invention also provides methods for diagnosing the status of an infection in a cell, tissue, organ or organism by analyzing the cell, tissue, organ or organism for the TERT mRNA, TERT DNA or TERT protein particular to the pathogen of interest. The TERT mRNA, TERT DNA or TERT protein can be isolated or assayed by methods well known to one skilled in the art of isolating and assaying for nucleic acids and proteins. The genus or species of the organism which can be analyzed by the methods of the present invention includes, but are not limited to, any mammal.

The detection and diagnosis methods encompassed by the present invention include those using fragments, segments or portions of the specific TERT nucleic acids or TERT proteins of the present invention, where such fragments, segments or portions are indicative of the TERT mRNA, TERT DNA or TERT protein particular to the organism of interest.

Particular embodiments of the present invention include methods of detecting the presence or absence of *C. albicans* or *P. falciparum* in a mammalian cell, tissue, organ or organism.

SEQ ID NO.1, SEQ ID NO.2, SEQ ID NO.3 or SEQ ID NO.4 can be used in methods for the detection and diagnosis of *C. albicans.* SEQ ID NO.5, SEQ ID NO.6, SEQ ID NO.7 or SEQ ID NO.8 can be used in methods for the detection and diagnosis of *P. falciparum.*

A further embodiment of the present invention provides methods for determining the presence or absence of a pathogen by measuring the level of telomerase activity of the pathogen within a cell, tissue, organ or organism. The level of the telomerase activity can be compared to that of normal cells in that tissue, organ or organism or compared to normal cells of organisms known not to be afflicted with the pathogen.

A still further embodiment of the present invention provides methods for determining the relative or actual amount of a pathogen in a cell, tissue, organ or organism by analyzing the cell, tissue organ or organism for TERT mRNA, TERT DNA or TERT protein of the pathogen. The methods encompassed by the present invention include using fragments, segments or portions of these nucleic acids or proteins in such detection methods, where such fragments, segments or portions are indicative of the pathogen. Particular embodiments of the present invention include methods of detecting the presence or absence of *C. albicans* or *P. falciparum* in a mammalian cell, tissue, organ or organism. SEQ ID NO.1, SEQ ID NO.2, SEQ ID NO.3 or SEQ ID NO.4 can be used in methods for determining the relative or actual amounts of *C. albicans* in a sample. SEQ ID NO.5, SEQ ID NO.6, SEQ ID NO.7 or SEQ ID NO.8 can be used in methods for determining the relative or actual amounts of *P. falciparum* in a sample.

Methods to Identify Binding Partners

Another embodiment of the present invention provides methods for use in isolating and identifying binding partners of proteins of the invention. In detail, a TERT protein or TERT protein fragment of the invention is mixed with a potential binding partner or an extract or fraction of a cell under conditions that allow the association of potential binding partners with the protein of the invention. After mixing, peptides, polypeptides, proteins or other molecules that have become associated with a proteins of the invention are separated from the mixture. The binding partner that binds to the proteins of the invention can then be removed and further analyzed. To identify and isolate a binding partner, the entire proteins, for instance the entire amino acid protein of SEQ ID NO.2, SEQ ID NO.4, SEQ ID NO.6, SEQ ID NO.8 or SEQ ID NO.10 can be used. Alternatively, a fragment of the proteins can be used. For example, the protein fragments encoded by SEQ ID NO.8 or SEQ ID NO.10 can be utilized in the present invention.

As used herein, a cellular extract refers to a preparation or fraction which is made from a lysed or disrupted cell of the organism of interest. The preferred source of cellular extracts will be cells derived from yeast, protozoan, human or plant tissue. Cells of interest include neoplastic cells and normal cells. Alternatively, cellular extracts may be prepared from available cell lines or newly-created cell lines, particularly transformed and proliferating cells.

A variety of methods can be used to obtain an extract of a cell. Cells can be disrupted using either physical or chemical disruption methods. Examples of physical disruption methods include, but are not limited to, sonication and mechanical shearing. Examples of chemical lysis methods include, but are not limited to, detergent lysis and enzyme lysis. A skilled artisan can readily adapt methods for preparing cellular extracts in order to obtain extracts for use in the present methods.

Once an extract of a cell is prepared, the extract is mixed with the proteins of the invention under conditions in which association of the proteins with the binding partners can occur. A variety of conditions can be used, the most preferred being conditions that closely resemble conditions found in the cytoplasm of a yeast, protozoan, human or plant cell. Features such as osmolarity, pH, temperature, and the concentration of cellular extract used, can be varied to optimize the association of the proteins with the binding partners.

After mixing under appropriate conditions, the bound complex is separated from the mixture. A variety of techniques can be utilized to separate the mixture. For example, antibodies specific to a proteins of the invention can be used to immunoprecipitate the binding partner complex. Alternatively, standard chemical separation techniques such as chromatography and density/sediment centrifugation can be used.

After removal of non-associated cellular constituents found in the extract, the binding partner can be dissociated from the complex using conventional methods. For example, dissociation can be accomplished by altering the salt concentration or pH of the mixture. To aid in separating associated binding partner pairs from the mixed extract, the proteins of the invention can be immobilized on a solid support. For example, the proteins can be attached to a nitrocellulose matrix or acrylic beads. Attachment of the proteins to a solid support aids in separating peptide/binding partner pairs from other constituents found in the extract. The identified binding partners can be either a single protein or a complex made up of two or more proteins. Alternatively, binding partners may be identified using a Far-Western assay according to the procedures of Takayama et al., *Methods Mol Biol* 69:171–84, 1997 or Sauder et al., *J GenVirol* 77(5):991–6, 1996 or identified through the use of epitope tagged proteins or GST fusion proteins.

Alternatively, the nucleic acid molecules of the invention can be used in a yeast two-hybrid system. The yeast two-hybrid system has been used to identify other protein partner pairs and can readily be adapted to employ the nucleic acid molecules herein described.

Methods to Identify Agents that Modulate the Expression of a Nucleic Acid Encoding the TERT Proteins of the Present Invention Methods of screening for agents which inhibit telomerase activity and more specifically methods of inhibiting human telomerase activity are set forth in U.S. Pat. No. 5,645,986. Such methods require combining a potential agent, an active telomerase, a substrate oligonucleotide for the telomerase and nucleotide triphosphates. These methods further require using an oligonucleotide probe which hybridizes to the specific telomere repeat sequences which are added. The telomeric nucleic acid probes utilized by these methods are specific for the telomeric repeats which a particular telomerase adds to the ends of the chromosomes. U.S. Pat. No. 5,830,644 sets forth methods of screening to identify an agent which increases telomerase activity in a cell by comparing the telomerase activity of treated and untreated cells. The methods set forth in these patents do not directly utilize a TERT gene or a TERT protein of a specific pathogen.

Until the present invention, the TERT genes and TERT proteins of *P. falciparum* and *C. albicans* were not available for use in methods of screening for agents which inhibit or promote the growth of these pathogens.

Thus, another embodiment of the present invention provides methods for identifying agents that modulate the expression of a nucleic acid encoding a protein of the invention such as a protein having the amino acid sequence of SEQ ID NO.2, SEQ ID NO.4, SEQ ID NO.6, SEQ ID NO.8 or SEQ ID NO.10. Such assays may utilize any available means of monitoring for changes in the expression level of the nucleic acids of the invention. As used herein, an agent is said to modulate the expression of a nucleic acid of the invention, for instance a nucleic acid encoding the protein having the sequence of SEQ ID NO.2, SEQ ID NO.4, SEQ ID NO.6, SEQ ID NO.8 or SEQ ID NO.10, if it is capable of up- or down-regulating expression of the nucleic acid in a cell.

In one assay format, cell lines that contain reporter gene fusions between the open reading frame defined by SEQ ID NO.1, SEQ ID NO.3, SEQ ID NO.5, SEQ ID NO.7 or SEQ ID NO.9 and any assayable fusion partner may be prepared. Numerous assayable fusion partners are known and readily available including the firefly luciferase gene and the gene encoding chloramphenicol acetyltransferase (Alam et al., (1990) *Anal Biochem* 188:245–254). Cell lines containing the reporter gene fusions are then exposed to the agent to be tested under appropriate conditions and time. Differential expression of the reporter gene between samples exposed to the agent and control samples identifies agents which modulate the expression of a nucleic acid encoding a protein having the sequence of SEQ ID NO.2, SEQ ID NO.4, SEQ ID NO.6, SEQ ID NO.8 or SEQ ID NO.10.

Additional assay formats may be used to monitor the ability of the agent to modulate the expression of a nucleic acid encoding a protein of the invention such as the protein having SEQ ID NO.2, SEQ ID NO.4, SEQ, ID NO.6, SEQ ID NO.8 or SEQ ID NO.10. For instance, mRNA expression may be monitored directly by hybridization to the nucleic acids of the invention. Cell lines are exposed to the agent to be tested under appropriate conditions and time and total RNA or mRNA is isolated by standard procedures such those disclosed in Sambrook et al. (*Molecular Cloning: A Laboratory Manual,* 2nd Ed. Cold Spring Harbor Laboratory Press, 1989).

In order to assay gene expression of the present invention in a physiologically relevant manner, tissues may be analyzed under conditions which model neoplastic or normal cell stages of proliferation and differentiation. Cells which express or fail to express a particular gene involved in the activation, inactivation or regulation of TERT transcription and expression may be particularly useful in the assays discussed herein. Such cells can exist naturally or be the result of genetic manipulation, such as specialized cells created via gene transformation or gene disruption. For example, cells with or without the MYC proto-oncogene may be of interest in methods used for identifying agents which modulate TERT gene expression. The MYC proto-oncogene encodes a ubiquitous transcription factor (c-MYC) involved in the control of cell proliferation and differentiation (Wu et al., 1999). TERT and c-MYC are expressed in normal and transformed proliferating cells, downregulated in quiescent and terminally differentiated cells, and can both induce immortalization when constitutively expressed in transfected cells. As another example, telomerase activity is suppressed during terminal differentiation of HL-60 promyelocytic leukaemic cells (Xu et al., 1999).

Probes to detect differences in RNA expression levels between cells exposed to the agent and control cells may be prepared from the nucleic acids of the invention. It is preferable, but not necessary, to design probes which hybridize only with target nucleic acids under conditions of high stringency. Only highly complementary nucleic acid hybrids form under conditions of high stringency. Accordingly, the stringency of the assay conditions determines the amount of complementarity which should exist between two nucleic acid strands in order to form a hybrid. Stringency should be chosen to maximize the difference in stability between the probe:target hybrid and potential probe:non-target hybrids.

Probes may be designed from the nucleic acids of the invention through methods known in the art. For instance, the G+C content of the probe and the probe length can affect probe binding to its target sequence. Methods to optimize probe specificity are commonly available in Sambrook et al. (*Molecular Cloning: A Laboratory Manual,* Cold Spring Harbor Press, N.Y., 1989) or Ausubel et al. (*Current Protocols in Molecular Biology* Greene Publishing Co., N.Y., 1995).

Hybridization conditions are modified using known methods, such as those described by Sambrook et al. and Ausubel et al. as required for each probe. Hybridization of total cellular RNA or RNA enriched for polyA RNA can be accomplished in any available format. For instance, total cellular RNA or RNA enriched for polyA RNA can be affixed to a solid support and the solid support exposed to at least one probe comprising at least one, or part of one of the sequences of the invention under conditions in which the probe will specifically hybridize. Alternatively, nucleic acid fragments comprising at least one, or part of one of the sequences of the invention can be affixed to a solid support, such as a a porous glass wafer. The glass wafer can then be exposed to total cellular RNA or polyA RNA from a sample under conditions in which the affixed sequences will specifically hybridize. Such glass wafers and hybridization methods are widely available, for example, those disclosed by Beattie (WO 95/11755). By examining for the ability of a given probe to specifically hybridize to an RNA sample from an untreated cell population and from a cell population exposed to the agent, agents which up or down regulate the expression of a nucleic acid encoding the protein having the sequence of SEQ ID NO.2, SEQ ID NO.4, SEQ ID NO.6, SEQ ID NO.8 or SEQ ID NO.10 are identified.

Hybridization for qualitative and quantitative analysis of mRNAs may also be carried out by using a RNase Protection Assay (i.e., RPA, see Ma et al., *Methods* 10: 273–238, 1996). Briefly, an expression vehicle comprising cDNA encoding the gene product and a phage specific DNA dependent RNA polymerase promoter (e.g., T7, T3 or SP6 RNA polymerase) is linearized at the 3' end of the cDNA molecule, downstream from the phage promoter, wherein such a linearized molecule is subsequently used as a template for synthesis of a labeled antisense transcript of the cDNA by in vitro transcription. The labeled transcript is then hybridized to a mixture of isolated RNA (i.e., total or fractionated mRNA) by incubation at 45° C. overnight in a buffer comprising 80% formamide, 40 mM Pipes, pH 6.4, 0.4 M NaCl and 1 mM EDTA. The resulting hybrids are then digested in a buffer comprising 40 $\mu$g/ml ribonuclease A and 2 $\mu$g/ml ribonuclease. After deactivation and extraction of extraneous proteins, the samples are loaded onto urea/polyacrylamide gels for analysis.

In another assay format, agents which effect the expression of the instant gene products, cells or cell lines would first be identified which express said gene products physiologically. Cell and/or cell lines so identified would be expected to comprise the necessary cellular machinery such that the fidelity of modulation of the transcriptional apparatus is maintained with regard to exogenous contact of agent with appropriate surface transduction mechanisms and/or the cytosolic cascades. Further, such cells or cell lines would be transduced or transfected with an expression vehicle (e.g., a plasmid or viral vector) construct comprising an operable non-translated 5'-promoter containing end of the structural gene encoding the instant gene products fused to one or more antigenic fragments, which are peculiar to the instant gene products, wherein said fragments are under the transcriptional control of said promoter and are expressed as polypeptides whose molecular weight can be distinguished from the naturally occurring polypeptides or may further comprise an immunologically distinct tag. Such a process is well known in the art (see Maniatis, 1982). Elements responsible for promoter activity of hTERT are known to be contained within a region extending from 330 bp upstream of the ATG to the second exon of the hTERT gene (Cong et al., 1999).

Cells or cell lines transduced or transfected as outlined above would then be contacted with agents under appropriate conditions; for example, the agent comprises a pharmaceutically acceptable excipient and is contacted with cells comprised in an aqueous physiological buffer such as phosphate buffered saline (PBS) at physiological pH, Eagles balanced salt solution (BSS) at physiological pH, PBS or BSS comprising serum or conditioned media comprising PBS or BSS and/or serum incubated at 37° C. Said conditions may be modulated as deemed necessary by one of skill in the art. Subsequent to contacting the cells with the agent, said cells will be disrupted and the polypeptides of the disruptate are fractionated such that a polypeptide fraction is pooled and contacted with an antibody to be further processed by immunological assay (e.g., ELISA, immunoprecipitation or Western blot). The pool of proteins isolated from the "agent contacted" sample will be compared with a control sample where only the excipient is contacted with the cells and an increase or decrease in the immunologically generated signal from the "agent contacted" sample compared to the control will be used to distinguish the effectiveness of the agent.

Methods to Identify Agents that Modulate at Least One Activity of the TERT Proteins Another embodiment of the present invention provides methods for identifying agents that modulate at least one activity of a protein of the invention such as the protein having the amino acid sequence of SEQ ID NO.2, SEQ ID NO.4, SEQ ID NO.6, SEQ ID NO.8 or SEQ ID NO.10. Such methods or assays may utilize any means of monitoring or detecting the desired activity, such as the synthesis of telomeric DNA, cell immortalization, tumorigenesis or cell proliferation.

In one format, an assay may involve comparing the relative amounts of a protein of the present invention between a cell population that has been exposed to the agent to be tested to that of an un-exposed control cell population. In this format, probes such as specific antibodies are used to monitor the differential expression of the protein in the different cell populations. Cell lines or populations are exposed to the agent to be tested under appropriate conditions and time. Cellular lysates may be prepared from the exposed cell line or population and a control, unexposed cell line or population. The cellular lysates are then analyzed with the probe.

Antibody probes are prepared by immunizing suitable mammalian hosts in appropriate immunization protocols using the peptides, polypeptides or proteins of the invention if they are of sufficient length, or, if desired, or if required to enhance immunogenicity, conjugated to suitable carriers. Methods for preparing immunogenic conjugates with carriers such as BSA, KLH, or other carrier proteins are well known in the art. In some circumstances, direct conjugation using, for example, carbodiimide reagents may be effective; in other instances linking reagents such as those supplied by Pierce Chemical Co., Rockford, Ill., may be desirable to provide accessibility to the hapten. The hapten peptides can be extended at either the amino or carboxy terminus with a Cys residue or interspersed with cysteine residues, for example, to facilitate linking to a carrier. Administration of the immunogens is conducted generally by injection over a suitable time period and with use of suitable adjuvants, as is generally understood in the art. During the immunization schedule, titers of antibodies are taken to determine adequacy of antibody formation.

While the polyclonal antisera produced in this way may be satisfactory for some applications, for pharmaceutical compositions, use of monoclonal preparations is preferred. Immortalized cell lines which secrete the desired monoclonal antibodies may be prepared using the standard method of Kohler and Milstein (*Nature* 256(5517):495–7, 1975; *Eur J Immunol* 6(7):511–9, 1976; and *Biotechnology* 24:524–6, 1992) or modifications which effect immortalization of lymphocytes or spleen cells, as is generally known. The immortalized cell lines secreting the desired antibodies are screened by immunoassay in which the antigen is the peptide hapten. polypeptide or protein. When the appropriate immortalized cell culture secreting the desired antibody is identified, the cells can be cultured either in vitro or by production in ascites fluid.

The desired monoclonal antibodies are then recovered from the culture supernatant or from the ascites supernatant. Fragments of the monoclonals or the polyclonal antisera which contain the immunologically significant portion can be used as antagonists, as well as the intact antibodies. Use of immunologically reactive fragments, such as the Fab, Fab', of F(ab')$_2$ fragments is often preferable, especially in a therapeutic context, as these fragments are generally less immunogenic than the whole immunoglobulin.

The antibodies or fragments may also be produced, using current technology, by recombinant means. Antibody regions that bind specifically to the desired regions of the protein can also be produced in the context of chimeras with multiple species origin, for instance, humanized antibodies.

Agents that are assayed in the above method can be randomly selected or rationally selected or designed. As used herein, an agent is said to be randomly selected when the agent is chosen randomly without considering the specific sequences involved in the association of the a protein of the invention alone or with its associated substrates, binding partners, etc. An example of randomly selected agents is the use a chemical library or a peptide combinatorial library, or a growth broth of an organism.

As used herein, an agent is said to be rationally selected or designed when the agent is chosen on a nonrandom basis which takes into account the sequence of the target site and/or its conformation in connection with the agent's action. Agents can be rationally selected or rationally designed by utilizing the peptide sequences that make up these sites.

The agents of the present invention can be, as examples, peptides, small molecules, vitamin derivatives, as well as carbohydrates. A skilled artisan can readily recognize that there is no limit as to the structural nature of the agents of the present invention.

The peptide agents of the invention can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if non-gene-encoded amino acids are to be included.

Another class of agents of the present invention are antibodies immunoreactive with critical positions of proteins of the invention. Antibody agents are obtained by immunization of suitable mammalian subjects with peptides, containing as antigenic regions, those portions of the protein intended to be targeted by the antibodies.

Uses for Agents that Modulate at Least One Activity of the TERT Proteins

Agents that modulate or down-regulate the expression of the protein or agents such as agonists or antagonists of at least one activity of the proteins may be used to modulate biological and pathologic processes associated with the protein's function and activity. As used herein, a subject can be any mammal, so long as the mammal is in need of modulation of a pathological or biological process mediated by a protein of the invention. The term "mammal" is meant to include an individual belonging to the class Mammalia. The invention is particularly useful in the treatment of human subjects with conditions or diseases such as cancer, such as stomach cancer, malaria or vaginal candidiasis.

Pathological processes refer to a category of biological processes which produce a deleterious effect. For example, expression of a protein of the invention may be associated with tumorigenesis, malaria or vaginal candidiasis. The pathological processes associated with malaria and a list of drugs currently used in the chemotherapy of protozoal infections are set forth in J. W. Tracy and L. T. Webster, Jr., 1996, Malaria, In Goodman & Gilman's The Pharmacological Basis of Therapeutics, Ninth Edition, Ch. 40:965–985.

As used herein, an agent is said to modulate a pathological process when the agent reduces the degree or severity of the process. For instance, malaria may be prevented or disease progression modulated by the administration of agents which reduce or modulate in some way the expression or at least one activity of a protein, a gene, or a gene product (RNA or DNA) of the invention.

The agents of the present invention can be provided alone, or in combination with other agents that modulate a particular pathological process. For example, an agent of the present invention can be administered in combination with other agents commonly used to treat cancers, protozoan infections and yeast infections. As used herein, two agents are said to be administered in combination when the two agents are administered simultaneously or are administered independently in a fashion such that the agents will act at the same time.

The agents of the present invention can be administered via parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

The present invention further provides compositions containing one or more agents which modulate expression or at least one activity of a protein of the invention. While individual needs vary, determination of optimal ranges of effective amounts of each component is within the skill of the art. Typical dosages comprise 0.1 to 100 µg/kg body wt. The preferred dosages comprise 0.1 to 10 µg/kg body wt. The most preferred dosages comprise 0.1 to 1 µg/kg body wt.

In addition to the pharmacologically active agent, the compositions of the present invention may contain suitable pharmaceutically acceptable carriers comprising excipients and auxiliaries which facilitate processing of the active compounds into preparations which can be used pharmaceutically for delivery to the site of action. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers. Liposomes can also be used to encapsulate the agent for delivery into the cell.

The pharmaceutical formulation for systemic administration according to the invention may be formulated for enteral, parenteral or topical administration. Indeed, all three types of formulations may be used simultaneously to achieve systemic administration of the active ingredient.

Suitable formulations for oral administration include hard or soft gelatin capsules, pills, tablets, including coated tablets, elixirs, suspensions, syrups or inhalations and controlled release forms thereof.

In practicing the methods of this invention, the compounds of this invention may be used alone or in combination, or in combination with other therapeutic or diagnostic agents. In certain preferred embodiments, the compounds of this invention may be coadministered along with other compounds typically prescribed for these conditions according to generally accepted medical practice, such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds of this invention can be utilized in vivo, ordinarily in mammals, such as humans, sheep, horses, cattle, pigs, dogs, cats, rats and mice, or in vitro.

rDNA Molecules Containing a Nucleic Acid Molecule

The present invention further provides recombinant DNA molecules (rDNAs) that contain coding sequences. As used herein, a rDNA molecule is a DNA molecule that has been subjected to molecular manipulation in situ. Methods for generating rDNA molecules are well known in the art, for example, see Sambrook et al., *Molecular Cloning* (1989). In the preferred rDNA molecules, a coding DNA sequence is operably linked to expression control sequences and/or vector sequences.

The choice of vector and/or expression control sequences to which one of the protein family encoding sequences of the present invention is operably linked depends directly, as is well known in the art, on the functional properties desired, e.g., protein expression, and the host cell to be transformed. A vector contemplated by the present invention is at least capable of directing the replication or insertion into the host chromosome, and preferably also expression, of the structural gene included in the rDNA molecule.

Expression control elements that are used for regulating the expression of an operably linked proteins encoding sequence are known in the art and include, but are not limited to, inducible promoters, constitutive promoters, secretion signals, and other regulatory elements. Preferably, the inducible promoter is readily controlled, such as being responsive to a nutrient in the host cell's medium.

In one embodiment, the vector containing a coding nucleic acid molecule will include a prokaryotic replicon, i.e., a DNA sequence having the ability to direct autonomous replication and maintenance of the recombinant DNA molecule extrachromosomally in a prokaryotic host cell, such as a bacterial host cell, transformed therewith. Such replicons are well known in the art. In addition, vectors that include a prokaryotic replicon may also include a gene whose expression confers a detectable marker such as a drug resistance. Typical bacterial drug resistance genes are those that confer resistance to ampicillin or tetracycline.

Vectors that include a prokaryotic replicon can further include a prokaryotic or bacteriophage promoter capable of directing the expression (transcription and translation) of the coding gene sequences in a bacterial host cell, such as *E. coli*. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmids are pUC8, pUC9, pBR322 and pBR329 available from Biorad Laboratories, (Richmond, Calif.), pPL and pKK223 available from Pharmacia, Piscataway, N.J.

Expression vectors compatible with eukaryotic cells can also be used to form a rDNA molecules that contains a coding sequence. Eukaryotic cell expression vectors are well known in the art and are available from several commercial sources. Typically, such vectors are provided containing convenient restriction sites for insertion of the desired DNA segment. Typical of such vectors are pSVL and pKSV-10 (Pharmacia), pBPV-1/pML2d (International Biotechnologies, Inc.), pTDT1 (ATCC, #31255), the vector pCDM8 described herein, and the like eukaryotic expression vectors.

Eukaryotic cell expression vectors used to construct the rDNA molecules of the present invention may further include a selectable marker that is effective in an eukaryotic cell, preferably a drug resistance selection marker. A preferred drug resistance marker is the gene whose expression results in neomycin resistance, i.e., the neomycin phosphotransferase (neo) gene. (Southern et al., *J Mol. Anal. Genet* 1:327–341, 1982.) Alternatively, the selectable marker can be present on a separate plasmid, and the two vectors are introduced by co-transfection of the host cell, and selected by culturing in the appropriate drug for the selectable marker.

Host Cells Containing an Exogenously Supplied Coding Nucleic Acid Molecule

The present invention further provides host cells transformed with nucleic acid molecules that encode the TERT proteins of the present invention. Eukaryotic cells useful for expression of a protein of the invention are not limited, so long as the cell line is compatible with cell culture methods and compatible with the propagation of the expression vector and expression of the gene product. Preferred eukaryotic host cells include, but are not limited to, yeast, protozoan, insect, plant and mammalian cells. Preferable vertebrate cells include those from a mouse, rat, monkey or human cell line. Preferred eukaryotic host cells include Chinese hamster ovary (CHO) cells available from the ATCC as CCL61, NIH Swiss mouse embryo cells NIH/3T3 available from the ATCC as CRL 1658, HL-60 promyelocytic cells, baby hamster kidney cells (BHK), and the like eukaryotic tissue culture cell lines. Various plant cells are also preferred hosts, including those of tomato, rice, wheat, corn, tobacco, Arabidopsis, soybean and alfalfa.

Any prokaryotic host can be used to express a rDNA molecule encoding a protein of the invention. The preferred prokaryotic host is *E. coli*.

Transformation of appropriate cell hosts with a rDNA molecule of the present invention is accomplished by well known methods that typically depend on the type of vector used and host system employed. With regard to transformation of prokaryotic host cells, electroporation and salt treatment methods are typically employed, see, for example, Cohen et al., *Proc. Natl. Acad. Sci. USA* 69:2110, 1972; and Maniatis et al., *Molecular Cloning, A Lab Manual,* Cold Spring Harbor Laboratory, Cold Spring Harbor, N.Y. (1982). With regard to transformation of vertebrate cells with vectors containing rDNAs, electroporation, cationic lipid or salt treatment methods are typically employed, see, for example, Graham et al., *Virol* 52:456, 1973; Wigler et al., *Proc Natl Acad Sci USA* 76:1373–76, 1979.

Successfully transformed cells, i.e., cells that contain a rDNA molecule of the present invention, can be identified by well known techniques including the selection for a selectable marker. For example, cells resulting from the introduction of an rDNA of the present invention can be cloned to produce single colonies. Cells from those colonies can be harvested, lysed and their DNA content examined for the presence of the rDNA using a method such as that described by Southern, *J Mol Biol* 98:503, 1975, or Berent et al., *Biotech.* 3:208, 198 or the proteins produced from the cell assayed via an immunological method.

Production of Recombinant Proteins Using a rDNA Molecule

The present invention further provides methods for producing a TERT protein of the invention using nucleic acid molecules herein described. In general terms, the production of a recombinant form of a protein typically involves the following steps:

First, a nucleic acid molecule is obtained that encodes a protein of the invention, such as the nucleic acid molecules depicted in SEQ ID NO.1, SEQ ID NO.3, SEQ ID NO.5, SEQ ID NO.7 or SEQ ID NO.9, or fragments of such sequences which encode an active TERT protein. If the encoding sequences are uninterrupted by introns, it is directly suitable for expression in any host.

The nucleic acid molecules are then preferably placed in operable linkage with suitable control sequences, as described above, to form an expression units containing the open reading frame of the TERT proteins or protein fragments. The expression unit is used to transform a suitable host and the transformed host is cultured under conditions that allow the production of the recombinant proteins. Optionally the recombinant proteins are isolated from the medium or from the cells; recovery and purification of the proteins may not be necessary in some instances where some impurities may be tolerated.

Each of the foregoing steps can be done in a variety of ways. For example, the desired coding sequences may be obtained from genomic fragments and used directly in appropriate hosts. The construction of expression vectors that are operable in a variety of hosts is accomplished using appropriate replicons and control sequences, as set forth herein. The control sequences, expression vectors, and transformation methods are dependent on the type of host cell used to express the gene and were discussed in detail herein. Suitable restriction sites can, if not normally available, be added to the ends of the coding sequence so as to provide an excisable gene to insert into these vectors. A skilled artisan can readily adapt any host/expression system known in the art for use with the nucleic acid molecules of the invention to produce recombinant proteins.

Genetic Transformation Methods

Production of Transgenic Protozoans

Transgenic protozoans, especially *P. falciparum,* clones containing recombinant genes corresponding to the DNA sequences of SEQ ID NO.1, SEQ ID NO.3, SEQ ID NO.5, SEQ ID NO.7 or SEQ ID NO.9 are a part of the invention.

Protozoans expressing heterologous genes can be produced by homologous recombination of circular plasmids into the corresponding chromosome loci. For a general discussion of the molecular biology of parasitic protozoans, see, D. F. Smith and M. Parsons, 1996, *Molecular Biology of Parasitic Protozoa* (Frontiers in Molecular Biology, 13).

Organisms such as *P. falciparum* (Yuda at al., 1999, *J. Exp. Med.,* 189(12):1947–1952; Menard et al., 1997, *Methods,* 13(2):148–157), *P. berghei* (van Dijk et al., 1995, *Science,* 268(5215):1358–1362) and *Toxoplasma gondii* (Black et al., 1998, *J. Biol. Chem.,* 273(7):3972–9) have been used.

Unlike yeast and bacterial recombinant systems, the purpose of which may be commercial production of heterologous proteins, these transformants usually are produced to provide a basis for studying the effects of gene alterations and knock-outs, as well as for studying the different stages in an organism's life cycle (Wu et al., 1996, PNAS, 93(3):1130–1134; Waters et al., 1997, *Methods,* 13(2):134–147).

Production of Transgenic Yeast

Transgenic yeast, especially *C. albicans,* clones containing recombinant genes corresponding to the DNA sequences of SEQ ID NO.1, SEQ ID NO.3, SEQ ID NO.5, SEQ ID NO.7 or SEQ ID NO.9 are a part of the invention.

For general discussion on producing transgenic yeasts, see, P. L. Bartel and S. Fields, 1997, *The Yeast Two-Hybrid System (Advances in Molecular Biology),* Oxford Univ. Press.; A. J. P. Brown et al., 1998, *Yeast Gene Analysis;* A. Adams et al., 1997, *Methods in Yeast Genetics,* 1997: A Cold Spring Harbor Laboratory Course Manual/With 1999 Biosupplynet Source Book; H. Heslot and C. Gaillardin, 1991, *Molecular Biology and Genetic Engineering of Yeasts.*

The production of recombinant yeasts and their use in the subsequent production of secreted and non-secreted heterologous proteins are well known and well characterized in the art (Russo et al., 1995, *J. Environ. Pathol. Toxicol. Oncol* 14(3–4):133–157; Buckholz et al., 1991, *Biotechnology,* 9(11):1067–1072; Tekamp-Olson et al., 1990, *Curr. Opinion Biotechnol.* 1:28–35; Brake et al., 1984, *PNAS* 81:4642–4646; Bitter et al., 1984, PNAS 81:5330–5334; Singh et al., 1984, Nucl. Acid. Res. 12:8927.

*C. albicans* can be transformed by traditional (biochemical) means (Datta et al., 1989, *Adv. Microb. Physiol.* 30:53–88 and U.S. Pat. Nos. 5,871,987 and 5,885,815) or by electroporation (U.S. Pat. No. 5,908,753).

In addition to *C. albicans* and *S. cerevisiae,* other transgenic yeasts can be created by transforming, with suitable vectors and promoters, organisms such as: *Pichia pastoris* (U.S. Pat. No. 4,879,231); *Kluyveromyces lactis* (U.S. Pat. Nos. 4,806,472 and 5,633,146); *Hansenula polymorpha* (U.S. Pat. Nos. 5,240,838 and 5,741,674); *Schizosaccharomyces pombe* (U.S. Pat. No. 5,663,061), *Schwanniomyces occidentalis* U.S. Pat. No. 5,100,794) and *Yarrowia lipolytica* (U.S. Pat. No. 4,880,741).

Recombinant proteins which have been successfully produced by yeast systems include, but are not limited to, alpha-interferon (U.S. Pat. No. 4,615,974); human growth hormone and human insulin (U.S. Pat. No. 4,775,622); platelet derived growth factor (U.S. Pat. No. 4,801,542); a herpes simplex virus gene (U.S. Pat. No. 5,059,538); epidermal growth factor (U.S. Pat. No. 5,102,789); desulphatohirudin, a protease inhibitor (U.S. Pat. No. 5,726,043); alpha, beta and gamma-globin (U.S. Pat. No. 5,827,693); and human serum albumin (U.S. Pat. No. 5,879,907).

Production of Transgenic Animals

Transgenic animals containing mutant, knock-out or modified genes corresponding to the DNA sequence of SEQ ID NO.1, SEQ ID NO.3, SEQ ID NO.5, SEQ ID NO.7 or SEQ ID NO.9 are also included in the invention.

Transgenic animals are genetically modified animals into which recombinant, exogenous or cloned genetic material has been experimentally transferred. Such genetic material is often referred to as a transgene. The nucleic acid sequence of the transgene, in this case an active form, fragment or segment of SEQ ID NO.1, SEQ ID NO.3, SEQ ID NO.5, SEQ ID NO.7 or SEQ ID NO.9, may be integrated either at a locus of a genome where that particular nucleic acid sequence is not otherwise normally found or at the normal locus for the transgene. The transgene may consist of nucleic acid sequences derived from the genome of the same species or of a different species, including non-animal species, than the species of the target animal.

The term "germ cell line transgenic animal" refers to a transgenic animal in which the genetic alteration or genetic information was introduced into a germ line cell, thereby conferring the ability of the transgenic animal to transfer the genetic information to offspring. If such offspring in fact possess some or all of that alteration or genetic information, then they too are transgenic animals.

The alteration or genetic information may be foreign to the species of animal to which the recipient belongs, foreign only to the particular individual recipient, or may be genetic information already possessed by the recipient. In the last case, the altered or introduced gene may be expressed differently than the native gene.

The development of transgenic technology allows investigators to create mammals of virtually any genotype and to assess the consequences of introducing specific exogenous nucleic acid sequences on the physiological and morphological characteristics of the transformed animals. The availability of transgenic animals permits cellular processes to be influenced and examined in a systematic and specific manner not achievable with most other test systems. For example, the development of transgenic animals provides biological and medical scientists with models that are useful in the study of disease. Such animals are also useful for the testing and development of new pharmaceutically active substances. Gene therapy can be used to ameliorate or cure the symptoms of genetically-based diseases.

Transgenic animals can be produced by a variety of different methods including transfection, electroporation, microinjection, biolistics (also called gene particle acceleration or microprojectile bombardment), gene targeting in embryonic stem cells and recombinant viral and retro viral infection (see, e.g., U.S. Pat. Nos. 4,736,866; 5,602,307; Mullins et al., *Hypertension* 22(4):630–633 (1993); Brenin et al., *Surg. Oncol.* 6(2)99–110 (1997); Tuan (ed.), *Recombinant Gene Expression Protocols,* Methods in Molecular Biology No.62, Humana Press (1997)).

The term "knock-out" generally refers to mutant organisms which contain a null allele of a specific gene. The term "knock-in" generally refers to mutant organisms into which a gene has been inserted through homologous recombination. The knock-in gene may be a mutant form of a gene which replaces the endogenous, wild-type gene.

A number of recombinant rodents have been produced, including those which express an activated oncogene sequence (U.S. Pat. No. 4,736,866); express simian SV 40 T-antigen (U.S. Pat. No. 5,728,915); lack the expression of interferon regulatory factor 1 (IRF-1) (U.S. Pat. No. 5,731,490); exhibit dopaminergic dysfunction (U.S. Pat. No. 5,723,719); express at least one human gene which participates in blood pressure control (U.S. Pat. No. 5,731,489); display greater similarity to the conditions existing in naturally occurring Alzheimer's disease (U.S. Pat. No. 5,720,936); have a reduced capacity to mediate cellular adhesion (U.S. Pat. No. 5,602,307); possess an bovine growth hormone gene (Clutter et al., *Genetics* 143(4):1753–1760 (1996)); and are capable of generating a fully human antibody response (McCarthy, *The Lancet* 349(9049):40(1997)).

While rodents, especially mice and rats, remain the animals of choice for most transgenic experimentation, in some instances it is preferable or even necessary to use alternative animal species. Transgenic procedures have been successfully utilized in a variety of non-murine animals, including sheep, goats, pigs, dogs, cats, monkeys, chimpanzees, hamsters, rabbits, cows and guinea pigs (see, e.g., Kim et al., *Mol. Reprod. Dev.* 46(4(:515–526 (1997); Houdebine, *Reprod. Nutr. Dev.* 35(6):609–617 (1995); Petters, *Reprod. Fertil. Dev.* 6(5):643–645 (1994); Schnieke et al., *Science* 278(5346):2130–2133 (1997); and Amoah, *J. Animal Science* 75(2):578–585 (1997)).

The method of introduction of nucleic acid fragments into recombination competent mammalian cells can be by any method which favors co-transformation of multiple nucleic acid molecules. Detailed procedures for producing transgenic animals are readily available to one skilled in the art, including the recitations in U.S. Pat. Nos. 5,489,743 and 5,602,307.

Production of Transgenic Plants

Transgenic plants can be produced by a variety of different transformation methods including, but not limited to, electroporation; microinjection; microprojectile bombardment, also known as particle acceleration or biolistic bombardment; viral-mediated transformation; and Agrobacterium-mediated transformation (see, e.g., U.S. Pat. Nos. 5,405,765, 5,472,869, 5,538,877, 5,538,880, 5,550,318, 5,641,664, 5,736,369 and 5,736,369; Watson et al., *Recombinant DNA*, Scientific American Books (1992); Hinchee et al., *Bio/Tech.* 6:915–922 (1988); McCabe et al., Bio/Tech. 6:923–926 (1988); Toriyama et al., *Bio/Tech* 6:1072–1074 (1988); Fromm et al., *Bio/Tech* 8:833–839 (1990); Mullins et al., *Bio/Tech* 8:833–839 (1990); and Raineri et al., *Bio/Tech.* 8:33–38 (1990)).

Methods of producing transgenic rice plants are well known to those skilled in the art of plant transformation. See, e.g., Hiei et al., 1994, *Plant J.* 6:271–282; Christou et al., 1992, *Trends in Biotechnology* 10:239; Lee et al., *Proc. Nat'l Acad. Sci. USA* 88:6389, U.S. Pat. Nos. 5,859,326, 5,861, 542, 5,952,485, and 5,952,553.

Genes successfully introduced into plants using recombinant DNA methodologies include, but are not limited to, those coding for the following traits: seed storage proteins, including modified 7S legume seed storage proteins (U.S. Pat. Nos. 5,508,468, 5,559,223 and 5,576,203); herbicide tolerance or resistance (U.S. Pat. Nos. 5,498,544 and 5,554, 798; Powell et al., *Science* 232:738–743 (1986); Kaniewski et al., *Bio/Tech* 8:750–754 (1990); Day et al., *Proc. Natl. Acad. Sci. USA* 88:6721–6725 (1991)); phytase (U.S. Pat. No. 5,593,963); resistance to bacterial, fungal, nematode and insect pests, including resistance to the lepidoptera insects conferred by the Bt gene (U.S. Pat. Nos. 5,597,945 and 5,597,946; Hilder et al., *Nature* 330:160–163; Johnson et al., *Proc. Natl. Acad. Sci. USA,* 86:9871–9875 (1989); Perlak et al., *Bio/Tech.* 8:939–943 (1990)); lectins (U.S. Pat. No. 5,276,269); and flower color (Meyer et al., *Nature* 330:677–678 (1987); Napoli et al., *Plant Cell* 2:279–289 (1990); van der Krol et al., *Plant Cell* 2:291–299 (1990)).

Homologous Recombination

Genes can be introduced in a site directed fashion using homologous recombination. This can be used in the creation of a transgenic animal, wherein the animal would be mutated, and the phenotype of the mutation could be studied for purposes of drug screening, investigating physiologic processes, developing new products and the like. Papers discussing homologous recombination are discussed in U.S. Pat. No. 5,413,923.

Homologous recombination permits site-specific modifications in endogenous genes and thus inherited or acquired mutations may be corrected, and/or novel alterations may be engineered into the genome. The application of homologous recombination to gene therapy depends on the ability to carry out homologous recombination or gene targeting in normal, somatic cells for transplantation.

To prepare cells for homologous recombination, embryonic stem cells or a stem cell line may be obtained. Cells other than embryonic stem cells can be utilized (e.g. hematopoietic stem cells etc.) (See U.S. Pat. No. 5,589,369 for more examples). The cells may be grown on an appropriate fibroblast fetal layer or grown in the presence of leukemia inhibiting factor (LIF) and then used. The embryonic stem cells may be injected into a blastocyst, that has been previously obtained, to provide a chimeric animal. The main advantage of the embryonic stem cell technique is that the cells transfected with the "transgene" can be tested prior to reimplantation into a female animal for gestation for integration and the effect of the transgenes. By subsequent cross-breeding experiments, animals can be bred which carry the transgene on both chromosomes. If mutations are incorporated into the transgenes which block expression of the normal gene production, the endogenous genes can be eliminated by this technique and functional studies can thus be performed.

Methods for intracellularly producing DNA segments by homologous recombination of smaller overlapping DNA fragments and transgenic mammalian cells and whole animals produced by such methods are disclosed in U.S. Pat. No. 5,612,205. Cell lines useful for analysis of human homologous interchromosomal recombination are provided in U.S. Pat. application Ser. No. 5,554,529.

Homologous recombination can also proceed extrachromasomally, which may be of benefit when handling large gene sequences (e.g., larger than 50 kb). Methods of performing extrachromosomal homologous recombination are described in U.S. Pat. No. 5,721,367.

Homologous recombination and site-directed integration in plants are discussed in U.S. Pat. Nos. 5,451,513, 5,501, 967 and 5,527,695.

Artificial Chromosomes

Components of Artificial Chromosomes

Artificial chromosomes are man-made linear DNA molecules constructed from essential DNA sequence elements that are responsible for the proper replication and partitioning of natural chromosomes (Murray et al., 1983). The essential elements necessary to construct artificial chromosomes include:

1) a centromere, which is the site of kinetochore assembly and is responsible for the proper distribution of replicated chromosomes at cell division (i.e., mitosis and meiosis);
2) two telomeres, the structures at the ends of a chromosome, which are needed to prevent the chromosome from being nibbled away by exonucleases;
3) an origin of replication, also known as Autonomous Replication Sequences (ARS), which are the positions along the chromosome at which DNA replication initiates.

The construction of functional artificial chromosomes provides an alternate method for transforming cells. Artificial chromosome vectors can be constructed to include gene sequences capable of producing specific polypeptides, wherein the gene sequences can include extremely long stretches of exogenous DNA. Of course, selectable marker genes can also be included in such artificial chromosomes to aid in the selection of transformed cells.

Use of artificial chromosome recombinant molecules as vectors solves many of the problems associated with alternative transformation technologies which are used to introduce new DNA into higher eukaryotic cells. Since artificial chromosomes are maintained in the cell nucleus as independently replicating DNA molecules, sequences introduced on such vectors are not subject to the variable expression due to integration position effects. In addition, the delivery of artificial chromosomes to the nucleus of a cell as intact, unbroken, double-stranded DNA molecules with telomeric ends ensures that the introduced DNA can be maintained stably in that form and that rearrangements should not occur. Furthermore, artificial chromosome vectors will be stably maintained in the nucleus through meiosis and will be available to participate in homology-dependent meiotic recombination. Exogenous DNA introduced via artificial chromosome vectors can be delivered to practically any cell without host range limitations, in contrast to some other transformation methods such as the Agrobacterium-mediated DNA transfer systems.

Yeast Artificial Chromosomes

Yeast artificial chromosomes (YACs) are genetically engineered chromosomes that contain the essential DNA sequence elements of Saccharomyces and segments of exogenous DNAs that are much larger than those accepted by conventional cloning vectors.

YACs are generated from synthetic minichromosomes that contain a yeast centromere, a replication origin, and fused telomeres. The circular chromosome also contains three marker genes (m1, m2, and m3), which when expressed, allow selection of the cells carrying the plasmid and two specific sites (Burke et al, 1987). These two sites allow specific restriction endonucleases to break the molecule. Cleavage at one site opens the ring, while cleavage at the second site generates centric and acentric fragments with ends that will accept exogenous DNA fragments. Once these ends are ligated, an artificial chromosome is generated with a short and a long arm, with the long arm containing the spliced segment of exogenous DNA to be cloned. Such artificial chromosomes are distributed normally during subsequent yeast divisions creating colonies containing the YACs. In cells possessing the insert, the m1 and m3 markers are expressed, but the damaged M2 is not, allowing religated YACs to be distinguished from unbroken plasmids. For further descriptions of this process, see T. A. Brown, Gene Cloning, Second Edition, Chapman & Hall (1990), U.S. Pat. Nos. 4,889,806 and 5,270,201.

Telomeric fragments of human DNA, including the sequence for the human telomere, ranging in size from 50 to 250 kilobases have been cloned into *Saccharomyces cerevisiae* using YAC vectors (see, e.g., Riethman et al., 1989; Guerrini et al., 1990).

YAC vectors can be constructed according to the methods detailed in U.S. Pat. Nos. 4,889,806 and 5,270,201.

Yeast ARSs have not been found to replicate in filamentous fungi (Fincham, 1989).

Mammalian Artificial Chromosomes

The controlled construction of mammalian artificial chromosomes (MACs) has been difficult because, with the exception of telomeres, the corresponding essential elements in mammals have not been fully defined. Higher eukaryotes (e.g., mammals), in contrast to yeast, contain repetitive DNA sequences which form a boundary at both sides of the centromere. This highly repetitive DNA interacting with certain proteins, especially in animal chromosomes, creates a genetically inactive zone (heterochromatin) around the centromere. This pericentric heterochromatin keeps any selectable marker gene at a considerable distance, and thus repetitive DNA prevents the isolation of centromere sequences by chromosome "walking." Alpha-satellite (alphoid) DNA forms a family of repeated DNA sequences found in amounts varying from 500 kb to 5 mb at the centromeres of human chromosomes. Alphoid sequences consist of a repeated 171 bp monomer that exhibits chromosome-specific variation in nucleotide sequence and higher order repeat arrangement.

U.S. Pat. No. 5,288,625 reports that a cell line which contains a dicentric chromosome, one of the centromeres of which contains a segment of human DNA, can be treated so as to isolate the centromere which contains the human DNA on a chromosome away from other mammalian chromosomes. Using a mouse lung fibroblast cell which contains such a dicentric chromosome wherein the centromere is linked to a dominant selectable marker (e.g., aminoglycoside-3' phosphotransferease-II), the inventor was able to isolate derivative cell lines which stably replicated a chromosome containing only centromeres comprising cloned human DNA.

Harrington et al. (1997) have constructed stable human artificial chromosomes by cotransfecting large synthetic arrays of alphoid repeats, telomere repeats, and random genomic DNA fragments into human cultured cells. In general, the resultant minichromosomes acquired host sequences by means of either a chromosome truncation event or rescue of an acentric fragment, but in one case minichromosome formation was by a de novo mechanism. The inclusion of uncharacterized genomic DNA in the transfection mixture raises the possibility that sequences other than the transfected alphoid and telomere DNA contributed to chromosome formation.

To construct YAC-based mammalian artificial chromosomes, Ikeno et al. (1998) introduced telomere repeats and selectable markers into a 100 kb YAC containing human centromeric DNA. The resultant YAC, which has regular repeat sequences of alpha-satellite DNA and centromere protein B (CENP-B) boxes, efficiently formed MACs that segregated accurately and bound CENP-B, CENP-C, and CENP-E. The MACs appear to be about 1–5 Mb in size and contain YAC multimers. It is not known whether the MACs are linear or circular. The data from structural analyses of the MACs by FISH and Southern blot hybridization suggest that the introduced YAC DNA itself must have been multimerized by recombination and/or amplification.

EXAMPLES

Example 1

Identification of a TERT Gene in *Plasmodium falciparum*

Three segments of DNA containing portions of the putative *P. falciparum* TERT gene were identified by searching the Unfinished Microbial Genomes database (at the National Center for Biotechnology Information) via the "BLAST" algorithm.

Initially, the search utilized the following segment of the *Schizosaccharomyces pombe* TERT protein sequence in the region identified as the "T motif": FFYITESSDLRNRTVY-FRKDIW (SEQ ID NO.11) (Linger et al., 1997).

Two matches were found (FIG. 1):
1. *P. falciparum* 3D7 unfinished sequence from chromosome 13 contig ID 41294 (3201 bp) from the Sanger Centre sequencing project; and
2. *P. falciparum* unfinished sequence from chromosome 14 contig 5560 (8833 bp) at The Institute for Genomic Research (TIGR).

A third match was found by searching the database using the following portion of the *S. pombe* C motif: LLRVVD-DFLFITVNKKDAKKFLNLSLR (SEQ ID NO.12). The third clone was a 4190 bp contig from the Sanger Centre (*P. falciparum* 3D7 unfinished sequence from chromosome 13 contig 56572 (mal31p$_{13}$ 02341) (FIG. 1).

We discovered that the *P. falciparum* TERT gene was embedded in larger segments of chromosomal sequence which had not in any way been recognized or identified by the sequencing projects that deposited the data.

The first two contigs (nos. 13-41294 and 14-5560) overlap to create ~10600 bp sequence including the entire putative *P. falciparum* TERT gene. The nucleotide sequence and corresponding amino acid sequence of the *P. falciparum* gene are presented in SEQ ID NO.5. The TERT protein sequence is provided in SEQ ID NO.6. The third contig (no. 13-56572) is a gene fragment that represents a second TERT gene in *P. falciparum*. Similarly, its nucleotide sequence and corresponding amino acid sequence appear in SEQ ID NOS. 7 and 8.

Sequence alignment of this ORF to TERT protein sequences of other organisms using Clustal® identified multiple regions of sequence similarity, showing that this protein is the *P. falciparum* TERT homolog (FIG. 2).

The Plasmodium protein sequence contains the canonical reverse transcriptase motifs 1, 2, A, B', C, D and E, as well as the T motif possessed by all TERT proteins identified to date. The T motif in combination with the reverse transcriptase motifs has not been observed in any other proteins.

Variability exists for the amino acid sequence of the *P. falciparum* TERT gene. For example, we have found that residue 330 of SEQ ID NO.6 can also be Ile (ie., CTA=Leu in contig 5560 and ATA=Ile in contig 41294). Additionally, we have found that residue 335 can also be Gly (ie., GAT=Asp in contig 5560 and CTT=Gly in contig 41294). Other variations of SEQ ID NO.6 are certainly likely based on our findings and this invention encompasses all such natural and artificial variations in amino acid sequences as discussed herein.

Example 2
Reverse Transcription-PCR for Identified *P. falciparum* TERT Gene

Figure 3:
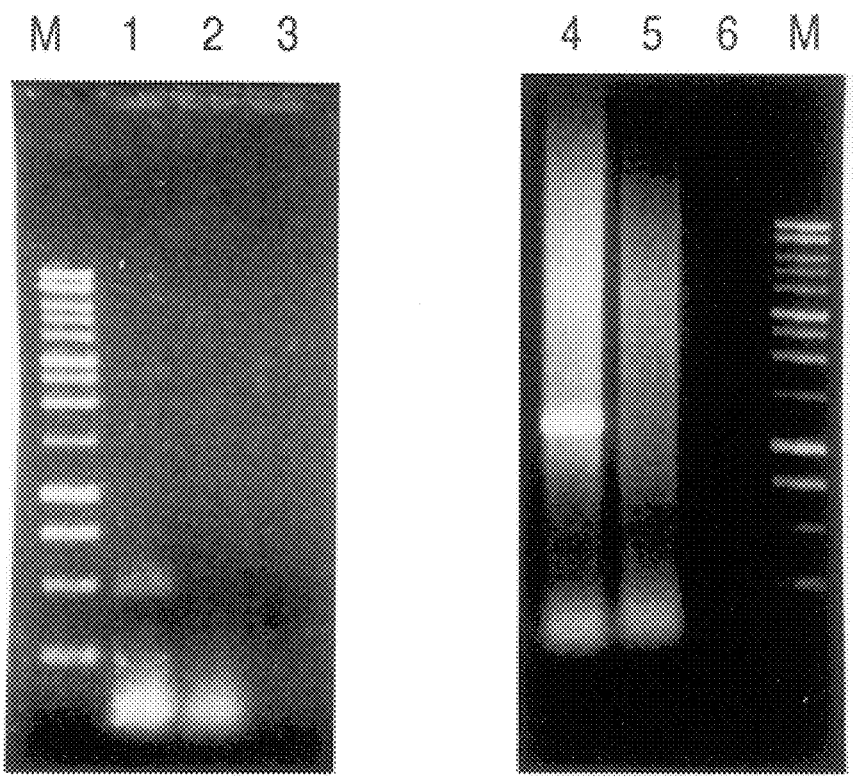
FIG. 3. TERT RT-PCR on Total RNA of *P. falciparum*.
M 1 kb ladder (Promega®).
Lane 1 RT-PCR of 4 µg *P. falciparum* total RNA with primers pfRT and pfTELfor (45 min at 48 C. followed by 40 cycles of 1 min at 94 C., 1 min at 52 C., 4 min at 68 C.), followed by nested PCR of 3 µl product with primers pfBREV and pfTELfor (20 cycles of 1 min at 94 C., 1 min at 52 C., 4 min at 68 C.). 25 µl product electrophoresed on 0.8% agarose gel. Arrow indicates signal for TERT MRNA.
Lane 2 No AMV-reverse transcriptase control. All other conditions same as Lane 1.
Lane 3 No template control. All other conditions same as Lane 1.
Lane 4 RT-PCR of 4 µg *P. falciparum* total RNA with pfRT2 and pf2160, followed by nested PCR with primers pfREV2 and pf2160. 10 µl product electrophoresed on 0.8% agarose gel.
Lane 5 No AMV-reverse transcriptase control. All other conditions same as Lane 4.
Lane 6 No template control. All other conditions same as Lane 4.

Total RNA prepared from *P. falciparum* was analyzed using reverse transcription coupled with the polymerase chain reaction (RT-PCR). DNA primers specific to the identified Plasmodium TERT gene were used to amplify two separate portions of the putative TERT mRNA. Control reactions were performed where reverse transcriptase was left out of the reaction to ensure signal did not arise from amplification of contaminating genomic DNA. See FIG. 3 and accompanying text for electrophoresis methods and results.

*P. falciparum* RT-PCR primers are as follows:
PfRT 5' GTC ATC AAT AAA TCG GAG TAT GAG TG (SEQ ID NO.32);
pfTELfor 5' TTC TAA CCA AAT CTG AGC (SEQ ID NO.33);
pfBREV 5' TGC ATA ATA TAG GGA GCA C (SEQ ID NO.34);
pfT2 5' CTTTTGCCATTCTCATATGAATATAC (SEQ ID NO.35);
pfREV2 5' ATTATTATGACGTGTGATG (SEQ ID NO.36);
pf2160 5' CATATAATTACATCGAGG (SEQ ID NO.37).

The RT-PCR process was repeated with two different primer sets amplifying different parts of the TERT gene. Results show that the TERT gene is indeed functional and not a pseudogene, as most transcribed protein genes are also translated into functional proteins.

Example 3
Identification of a Gene Fragment for a *P. falciparum* TERT Gene

In addition to the full length *P. falciparum* TERT gene of SEQ ID NO.5, we have identified a TERT gene fragment which represents a second TERT gene in *P. falciparum* (SEQ ID NO.7).

Protein translation of the second TERT gene (794 amino acids, corresponding to amino acids 1392 to 2184 of full length *P. falciparum* TERT) shows that there are 9 base changes as compared to the full length TERT sequence, resulting in 7 amino acid changes (amino acid numbers refer to the full length sequence):

1398 Ser to Gly
1399 Val to Ala
1614 Phe to Ser
1777 Ile to Asn
1870 Ser to Thr
1884 Leu to Val
1928 His to Gln.

Example 4
Identification of TERT Genes in *Candida albicans*

A segment of DNA containing a potential *Candida albicans* TERT gene was identified by searching the Unfinished Microbial Genomes database (at the National Center for Biotechnology Information) via the "BLAST" algorithm. The search utilized a segment of the *S. pombe* TERT protein sequence in the region identified as the "T motif" (Nakamura et al., 1997) [sequence WLYNS . . . CRPFIT, SEQ ID NO.11] compared to the eukaryotes database with the Expect parameter at 100.

The third match, with a match score of 34, was contig 3-3463 from the *C. albicans* sequencing project at the Stanford Sequencing and Technology Center. Contig 3-3463 is a 11961 base pair genomic fragment.

By taking the complement of the strand as obtained from the database, base pairs 144–2747 of the contig form an open reading frame (ORF) of 867 amino acids.

Additional work demonstrated that there were two different genes within a single *C. albicans* cell that both coded for TERT genes. This is the first such report of two TERT genes within a single cell or for two different TERT genes identified in a single organism. The existence of two TERT genes suggests that they different functions.

The two *C. albicans* TERT genes differ at 12 base pairs, 7 that are silent, and 5 that cause amino acid changes. Additionally, there are 7 residues in each gene (amino acid positions #114, 452, 487, 538, 634, 735, and 856) that are encoded by a CTG (CUG) codon that would normally be Leu, but are Ser in Candida. *C. albicans* is one of several Candida species that have an unusual tRNA that charges Ser onto the tRNA that reads CUG codons.

The nucleotide sequences and corresponding amino acid sequences of the two *C. albicans* genes are presented in SEQ ID NOs: 1 and 3. The corresponding TERT protein sequences are provided in SEQ ID NOs: 2 and 4, respectively.

Sequence alignment of this ORF to TERT protein sequences of other organisms using Clustal® identified multiple regions of sequence similarity, showing that this protein is the Candida TERT homolog (FIG. 2).

The Candida protein sequence contains the canonical reverse transcriptase motifs 1,2, A, B', C, D and E, as well as the T motif possessed by all TERT proteins identified to date. Besides these motifs, many other regions of sequence similarity are present between this and other TERT genes. The T motif in combination with the reverse transcriptase motifs has not been observed in any other proteins.

Example 5

Reverse Transcription-PCR for Identified *C. albicans* TERT Genes

Total RNA prepared from log phase *C. albicans* cells was analyzed using reverse transcription coupled with the polymerase chain reaction (RT-PCR). DNA primers specific to the identified Candida TERT genes were used to amplify four separate portions of the TERT mRNA.

The QIAGEN® Genomic Tip-100 Kit was used for the genomic DNA isolation procedure. The protocol for yeast was utilized as set forth in the QIAGEN® handbooks and protocols for the use of the kits (http://www/qiagen.com/literature/handbooks/index.html; QIAGEN® Genomic DNA Handbook September 1997 (PDF version, 224 KB)).

Briefly, *C. albicans* is inoculated into 50 ml GYEP media (glucose 2%, peptone 1%, yeast extract 0.3%) and grown overnight at 37 C. with shaking. Cells are washed with buffer Y1 (1M sorbitol, 0.1 M EDTA, pH 7.4) and incubated with buffer Y1 plus 0.1% beta mercaptoethanol, 50 units lyticase (zymolase) per $10^7$ cells for 1 h at 30 C. to break down cell walls. Spheroplasts are harvested by centrifigation at 300×g. The spheroplasts are then lysed, and run over the DNA binding columns, and the genomic DNA is washed on the column and eluted according to the manufacturer's instructions using the buffers provided by the manufacturer. *C. albicans* RTPCR primers:

CaRT1 CAGGGGGTATTGAAGAGATAGAAGCAGCG (SEQ ID NO.13);
CaFor1 TCGTTGTTATTCACGCGTATCG (SEQ ID NO.14);
CaNEST1 GCGACAATTGAGAGATATCGAG (SEQ ID NO.15);
CaRT2 GCACTTGATCATAAATATTCGAATCGGGCG (SEQ ID NO.16);
CaFOR2 TTATGGAAAGAGCTATACG (SEQ ID NO.17);
CaNEST2 TGAGAATCCCTGAAACACG (SEQ ID NO.18);
CaRT3 CAATTTATGTGAACGCGTCCAACTGAGCGTAG (SEQ ID NO.19);
CaFOR3 GATACGACATTCTATATGC (SEQ ID NO.20);
CaNEST3 TCAATACAGGTTGGCTGAG (SEQ ID NO.21).

We also used custom primers for sequencing the internal regions of the gene. They include the RTPCR primers listed above as well as the following:

CaFor480 5' TATTTCTGTTACTCGGACCA (SEQ ID NO.22);
CaFor1620 5' AGAGACTCCTTGTTAACC (SEQ ID NO.23);
CaFor1980 5' CAGTTAAAGATGCACGAGG (SEQ ID NO.24);
CaFor2310 5' TGAATAACAACAGATCTAAGC (SEQ ID NO.25);
CaFor2630 5' CAGCGACTGGGATGGTGC (SEQ ID NO.26);
CaRev290 5' ATTCTTGTGGTCGAATCGC (SEQ ID NO.27);
CaRev630 5' TAAAGCACATTGAATTTGG (SEQ ID NO.28);
CaRev1030 5' TAAATCATCCATATGTATC (SEQ ID NO.29);
CaRev1380 5' TAACACGAAAGCTCGAGCG (SEQ ID NO.30);
CaRev2340 5' AAACTTATCAGACCGGAG (SEQ ID NO.31).

Control reactions were performed where reverse transcriptase was left out of the reaction to ensure signal did not arise from amplification of contaminating genomic DNA. See FIG. 4 and accompanying text for electrophoresis methods and results.

A second RT-PCR was conducted using four *C. albicans* RT-PCR reactions, controls, and the same reactions done in genomic DNA described above. See FIG. 5 for overview of the procedures and the resultant gel.

Results show that the TERT gene is indeed functional and not a pseudogene, as most tanscribed protein genes are also translated into functional proteins.

Example 6

Identification of Two TERT Genes in Strain 3153 of *C. albicans*

Two overlapping PCR products, P1 and P2, representing the entire coding region of the TERT gene, were amplified from genomic DNA from *C. albicans* strain 3153 (serotype A). P1 was amplified using primers CaRTfor1 and CaRT3, and P2 was amplified using primers CaFor2 and CaRT. The reaction conditions were 40 cycles of 1 min. at 94 C., 1 min. at 52 C. and 3 min. at 68 C., followed by a final 6 min incubation at 68 C. The resulting PCR products were gel purified and sequenced on both strands using internal primers specific to *C. albicans* strain 3153 (serotype A).

RT-PCR was used to produce four overlapping PCR products, P1, P2, P3 and P4. These are the same four products described in the RT-PCR experiment used to determine if the TERT gene is transcribed (see above). RT-PCR was performed using the Access RT-PCR kit (Promega®). For all RT-PCR reactions, a negative control was done (no reverse transcriptase added) to ensure that products were indeed amplified from RNA and not potential contaminating genomic DNA. The resulting PCR products were gel purified and sequenced on both strands using internal primers specific to the *Candida albicans* TERT twelve sites on the gene where the data was ambiguous. At these locations, electropherogram data from both strands showed two overlapping peaks, making identification of the proper nucleotide at that position impossible. This did not appear to be an artifact of the sequencing reactions, as data on both sides of the nucleotide in question was of high quality and unambiguous, with data on both strands in agreement as to the nucleotide sequence. Additionally, the same sites were identified as ambiguous in sequencing the genomic DNA PCR products and the RT-PCR products derived from the RNA.

Comparison of the PCR products derived from the genomic DNA and the total cellular RNA also proves that there are no intron sequences in the Candida TERT gene. To prove that the overlapping peaks on the sequencing electropherograms were due to simultaneous amplification of multiple sequences, three RT-PCR products, P1, P2 and P5 (amplified with primers Ca480For and CaRT2) were cloned into the pGEM-T vector and individual clones were sequenced. The three overlapping pieces were utilized because the entire gene could not be amplified by PCR in one piece. The three pieces, however, overlap significantly. Of the 2601 base pairs that comprise the coding region, P1 spans bases 1–1659, P2 spans bases 1108–2601 and P5 spans bases 335–2047. Since only one amplicon is ligated into each vector, individual amplicons could be sequenced. Five P1, six P2 and two P5 clones were sequenced. At sites that had showed two overlapping base peaks on the electropherograms when PCR products were sequenced, clones would have either one or the other of the two bases. In this manner, the clones sorted into two classes, which when overlapped, generate the entire coding sequence of two genes, CaTERT1 and CaTERT2. These two genes differ at twelve positions, resulting in seven silent changes (that is, the two triplet codons designate the same amino acid) and five amino acid differences between the two proteins.

Example 7
Identification of Two TERT Genes in Strain 3153 of *C. albicans*

The TERT gene of another *Candida albicans* strain, 9938, was also amplified in two overlapping PCR products, P1 and P2, as was done with strain 3153(A). The PCR products were sequenced on both strands in the same manner as strain 3153(A). The sequence data clearly indicates that this strain also has two TERT genes, which are different from the two TERT genes found in strain 3153(A) (SEQ ID NOs.1 and 3, respectively).

Of the twelve differing sites in 3153(A), three are unambiguous in the sequencing data for strain 9938, while four sites that are identical in both genes of strain 3153(A) appear to differ in the two genes of strain 99938.

The sequences of strain 99938 match those of SEQ ID NOs.1 and 3 for *C. strain* 3153(A) except for the following changes as indicated below:

1. Position 1131 is always C, thus always Ser for the amino acid (rather than C or T in 3153A);
2. Position 2185 is always A, thus always Thr for the amino acid (rather than A or C in 3153A);
3. Position 2209 is always T (rather than T or C in 3153A). Amino acid is identical either way;
4. Position 2445, is either T or C (rather than always T in 3153A). Amino acid is Val or Asp (rather than always Val in 3153A);
5. Position 2485, is either T or C (only T in 3153A). Amino acid is Phe either way;
6. Position 1927 is either T or C (only C in 3153A), amino acid is identical; and
7. Position 2036 is either A or G (only G (Val) in 3153A). Amino acid is thus either Ile or Val.

Example 8
Identification of a TERT Gene Fragment in *Oryza sativa*

A segment of DNA containing a potential *Oryza sativa* TERT gene was identified by first searching the *Arabidopsis thaliana* database (at the Stanford University DNA Sequence and Technology Development Center homepage, www-sequence.stanford.edu) via the "BLAST" algorithm. The search utilized a segment of the Arabidopsis TERT protein sequence in the region identified as the "T" motif (Nakamura et al., 1997) (sequence WLYNS . . . CRPFIT, SEQ ID NO: 11) compared to the higher plant sequence database with the Expect parameter at 100.

The second match, with a match score of 74, was accession number AQ510589 from the *O. sativa* sequencing project at Clemson University. AQ510589 is a 531 base pair genomic fragment.

The BAC containing the sequence fragment of interest was obtained from Clemson University and resequenced. The sequences of the primers used for this process are (Note: K is G+T):
Rice ep-2for: 5'CCT KAA TAT TTK TTA ATK AKK (SEQ ID NO.38);
Rice er-rev 5' KTC ATA CCT CKT ATA ATC AKC (SEQ ID NO.39).
These primers are degenerate because they can also be used for Arabidopsis.

The nucleotide sequence and corresponding amino acid sequence of the *O. sativa* gene is presented in SEQ ID NO.9. The TERT protein sequence is provided in SEQ ID NO.10.

Sequence alignment of this ORF to the TERT nucleotide sequence of *Arabidopsis thaliana* (SEQ ID NO:48) identified multiple regions of sequence similarity, showing that this protein is the *O sativa* TERT homolog (FIG. 6). The *O. sativa* protein sequence contains the canonical reverse transcriptase motifs C, D and E.

Example 9
Reverse Transcription-PCR for Identified *O. sativa* TERT Gene Fragment Total RNA prepared from *O sativa* was analyzed using reverse transcription coupled with the polymerase chain reaction (RT-PCR) using the methods described above. DNA primers specific to the identified Oryza TERT gene were used to amplify separate portions of the putative TERT mRNA. Control reactions were performed where reverse transcriptase was left out of the reaction to ensure signal did not arise from amplification of contaminating genomic DNA.

Results show that the TERT gene fragment is indeed functional and not a pseudogene, as most transcribed protein genes are also translated into functional proteins.

Example 10
Use of the *O. sativa* TERT Gene Fragment as a Probe to Isolate TERT Genes from Plants The isolation of *O. sativa* TERT genes, TERT genes from other plant species, and related genes, such as TERT promoters, may be accomplished by a number of techniques. For instance, oligonucleotide probes based on the sequences disclosed herein can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. cDNA may be prepared from mRNA extracted from any rice cells in which TERT genes or homologs are expressed.

The cDNA or genomic library can then be screened using a probe based upon the rice TERT gene fragment of SEQ ID NO.9. Such a probe may include the entire sequence of SEQ ID NO.9 or a portion or fragment of this sequence. The probe may be used to hybridize with genomic DNA or cDNA sequences to isolate homologous genes in the same or different plant species.

Alternatively, the nucleic acids of interest can be amplified from nucleic acid samples using amplification techniques. For instance, polymerase chain reaction (PCR) technology to amplify the sequences of the TERT gene and related genes directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying TERT sequences from plant tissues are generated from comparisons of the sequences provided herein for rice. For a general review of PCR see Gelfand et al., 1990, *PCR Protocals: A Guide to Methods and Applications* (Academic Press, San Diego).

The foregoing detailed description has been given for clearness of understanding only and no unnecessary limitations should be understood therefrom as modifications will be obvious to skilled in the art.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

REFERENCES

All references, articles, texts and patents referred to above and below are hereby incorporated by reference in their entirety.

Aldous, W. K., et al. Sep. 15, 1998. Stage specific detection and inhibition studies of *Plasmodium falciparum* telomerase. (Madigan Army Medical Center, Tacoma Wash.). *Mol. Biochem. Parasitol.* 95(2):281–5.

Ausubel et al. 1995. *Current Protocols in Molecular Biology*, Greene Publishing Co., NY.

Benito, E. P., Campuzano, V., Lopez-Matas, M. A., De Vicente, J. I., and Eslava, A. P. 1995. Isolation, characterization and transformation, by autonomous replication, of *Mucor circinelloides* OMPdecase-deficient mutants. *Mol. Gen. Genet.* 248: 126–135.

Blackburn, E. H. 1995. Developmentally Programmed Healing of Chromosomes. In *Telomeres* (E. H. Blackburn and C. W. Greider, Eds.). Cold Spring Harbor Laboratory Press. Cold Spring Harbor, N.Y.

Broach, J. R, Li, Y.-Y., Feldman, J., Jayaram, M., Abraham, J., Nasmyth, K. A., and Hicks, J. B. 1982. Localization and sequence analysis of yeast origins of DNA replication. *Cold Spring Harbor Symp. Quant. Biol.* 47: 1165–1174.

Burke et al. 1987. Construction of Large Linear Plasmid Library From Higher Eucaryote Genomes. *J. Cell Biochem.* Supp. 11B.

Bryan, T. M. et al. Jul. 21, 1998. Telomerase reverse transcriptase genes identified in *Tetrahymena thermophila* and *Oxytricha trifallax*. *Proc. Natl. Acad. Sci. USA* 95(15): 8479–84.

Bryan, T. M. and Cech, T. R. June 1999. Telomerase and the maintenance of chromosome ends. *Curr. Opin. Cell Biol.* 11(3):318–14.

Cohn, M. and E. H. Blackburn. 1995. Telomerase in yeast. *Science.* 269:396–400.

Cooke, H. 1995. Non-programmed and Engineered Chromosome Breakage. In *Telomeres* (E. H. Blackburn and C. W. Greider, Eds.). Cold Spring Harbor Laboratory Press. Cold Spring Harbor, N.Y.

Fang, G. and Cech, T. R. 1995. Telomere Proteins. In *Telomeres* (E. H. Blackburn and C. W. Greider, Eds.). Cold Spring Harbor Laboratory Press. Cold Spring Harbor, N.Y.

Fincham, J. R. S. 1989. Transformation in fungi. *Microbiol. Rev.* 53:148–170.

Gall, J. G. 1995. Beginning of the End: Origins of the Telomere Concept. In *Telomeres* (E. H. Blackburn and C. W. Greider, Eds.). Cold Spring Harbor Laboratory Press. Cold Spring Harbor, N.Y.

Greenberg, R. A. et al. Feb. 4, 1999. Telomerase reverse transcriptase gene is direct target of c-Myc but is not functionally equivalent in cellular transformation. *Oncogene* 18(5):1219–26, Greider et al. 1990. Telomeres Telomerase and Senescence. *Bio. Assays.* 12(8):363–369.

Guerrini A. M., F. Ascenzioni, G. Pisani, G. Rappazzo, G. Della Valle, and P. Donini. 1990. Cloning a fragment from the telomere of the long arm of human chromosome 9 in a YAC vector. *Chromosoma.* 99(2):138–142.

Harrington, J. J., G. Van Bokkelen, R. W. Mays, K. Gustashaw, and H. F. Willard. 1997 . Formation of de novo centromeres and construction of first-generation human artificial microchromosomes. *Nat. Genet.* 4:345–355.

Harley. 1991. Mutation Research. 256:271.

Henderson, E. 1995. Telomere DNA Structure. In *Telomeres* (Blackburn, E. H. and Greider, C. W., Eds.). Cold Spring Harbor Laboratory Press, Cold Spring Harbor, N.Y.

Holt S. E. and Shay, J. W. July 1999. Role of telomerase in cellular proliferation and cancer. *J. Cell Physiol.* 180(1): 10–18.

Ikeno, M. B. Grimes, T. Okazaki, M. Nakano, K. Saitoh, H. Hoshino, N. McGill, H. Cooke, and H. Masumoto. 1998. Construction of YAC-based mammalian artificial chromosomes. *Nature Biotechnology.* 16:431–439.

Isaac, S. 1992. *Fungal-Plant Interactions.* Chapman & Hall, London, UK.

Ito, H., S. Kyo, T. Kanaya, M. Takakura, K. Koshida, M. Namiki and M. Inoue. 1998. Detection of human telomerase reverse transcriptase messenger RNA in voided urine samples as a useful diagnostic tool for bladder cancer. *Clin. Cancer Res.* 4(11):2807–10.

Kim, N. W. et al. 1994. Specific association of human telomerase activity with immortal cells and cancer. *Science.* 266:2011.

Kwon-Chun, K. August 1998. Gene disruption to evaluate the role of fungal candidate virulence genes. *Curr. Opin. Microbiol.* 1(4):381–9.

Ligner J. et al. Apr. 25, 1997. Reverse transcriptase motifs in the catalytic subunit of telomerase. Science 276(5312) :561–7.

Lundblad et al. 1990. RNA-dependent polymerase motifs in EST1: tentative identification of a protein component of an essential yeast telomere. *Cell.* 60:529–530.

Lundblad et al. 1993. An alternative pathway for yeast telomere maintenance rescues est1⁻ senescence. *Cell.* 73:347–360.

Maniatis et al. 1982. *Molecular Cloning,* Cold Spring Harbor Laboratory, Cold Spring Harbor, N.Y.

McCullough, M. J. et al. April 1996. *Candida albicans:* a review of its history, taxonomy, epidemiology, virulence attributes, and methods of strain differentiation. *Int. J. Oral Maxillofac. Surg.* 25(2):136–44.

McEachern et al. 1996. Cap-prevented recombination between terminal telomeric repeat arrays (telomere CPR) maintains telomeres in *Kluyveromyces lactis* lacking telomeres. *Genes & Development.* 10:1822–1834.

Murray et al. 1983. Nature. 301:189–193.

Nag Raj, T. R. 1993. Coelomycetous Anamorphs with Appendage-bearing Conidia. pp. 618–671. Mycologue Publications, Waterloo, Ontario.

Nakamura, T. M. et al. Aug. 15, 1997. Telomerase catalytic subunit homologs from fission yeast and human. *Science* 299(5328):955–9.

Raymond, E. et al. December 1996. Agents that target telomerase and telomeres. *Curr. Opin. Biotechnol.* 7(6) :583–91.

Reithman H. C., R. K. Moyzis, J. Meyne, D. T. Burke, and M. V. Olson. 1989. Cloning human telomeric DNA fragments into *Saccharomyces cerevisiae* using a yeast-artificial-chromosome vector. *Proc. Natl. Acad. Sci.* 86(16):6240–6244.

Sambrook, J., Fritsch, E. F., and Maniatis, T. 1989. *Molecular Cloning: a Laboratory Manual,* 2nd ed. Cold Spring Harbor Laboratory Press. Cold Spring Harbor, N.Y.

Smith, T. L., Gaskell, J., Berka, R. M., Yang, M., Henner, D. J., and Cullen, D. 1990. The promoter of the glucoamylase-encoding gene of *Aspergillus niger* functions in *Ustilago maydis. Gene* 88: 259–262.

Tsao, D. A., C. W. Wu and Y. S. Lin. 1998. Molecular cloning of bovine telomerase RNA. *Gene* 221(1):51–8.

Wang et al., 1990. Telomere-telomere recombination provides an express pathway for telomere acquisition. *Nature.* 345:455–460.

Williamson, J. R., Raghuraman, M. K., and Cech, T. R. 1989. Monovalent cation-induced structure of telomeric DNA: The G-quartet model. *Cell* 59: 871–880.

Cong, Y. S., J. Wen and S. Bacchetti. 1999. The human telomerase catalytic subunit hTERT: organization of the gene and characterization of the promoter. *Hum. Mol. Genet.* 8(1):137–42.

Woods, J. P. and Goldman, W. E. 1992. In vivo generation of linear plasmids with addition of telomeric sequences by *Histoplasma capsulatum. Mol. Microbiol.* 6: 3603–3610.

Woods, J. P. and Goldman, W. E. 1993. Autonomous replication of foreign DNA in *Histoplasma capsulatum:* role of native telomeric sequences. *J. Bacteriol.* 175: 636–641.

World Health Organization. Revised October 1998. Fact Sheet No 94. *Malaria.*

Wu, K. J., C. Grandori, M. Amacker, N. Simon-Vermot, A. Polack, J. Lingner and R. Dalla-Favera. 1999. Direct activation of TERT transcription by c-MYC. *Nat. Genet.* 21(2):220–4.

Yasui, W., H. Tahara, E. Tahara, J. Fujimoto, J. Nakayama, F. Ishikawa, T. Ide and E. Tahara. 1998. Expression of telomerase catalytic component, telomerase reverse transcriptase, in human gastric carcinomas. *Jpn. J. Cancer Res.* 89(11):1099–103.

Zakian, V. A. 1997. Life and cancer without telomerase. *Cell.* 91:1–3.

What is claimed is:

1. An isolated nucleic acid molecule having at least 80% identity to a polynucleotide molecule that encodes the amino acid sequence of SEQ ID NO:2 or SEQ ID NO: 4, wherein said nucleic acid molecule encodes an amino acid sequence having telomerase reverse transcriptase activity.

2. An isolated nucleic acid molecule having at least 90% identity to a polynucleotide molecule that encodes the amino acid sequence of SEQ ID NO:2 or SEQ ID NO: 4, wherein said nucleic acid molecule encodes an amino acid sequence having telomerase reverse transcriptase activity.

3. An isolated nucleic acid molecule that hybridizes to a polynucleotide molecule that encodes SEQ ID NO:2 or SEQ ID NO:4 under the following conditions: 6×SSC, 5×Denhardt's solution, 0.5% SDS, 10 mM EDTA pH 8, and 100 mg/ml sheared and denatured salmon sperm DNA at 65° C., wherein said nucleic acid molecule encodes an amino acid sequence which has telomerase reverse transcriptase activity.

4. An isolated nucleic acid molecule encoding a fragment of at least 25 amino acids of SEQ ID NO. 2 or SEQ ID NO: 4, wherein the fragment has telomerase reverse transcriptase activity.

5. An isolated nucleic acid molecule encoding the amino acid sequence of SEQ ID NO: 2 or SEQ ID NO: 4.

6. The isolated nucleic acid molecule of any one of claims 1–5, wherein the nucleic acid molecule comprises the sequence of SEQ ID NO.1 or SEQ ID NO.3.

7. The isolated nucleic acid molecule of claim 6, wherein the nucleic acid molecule consists of the sequence of SEQ ID NO.1 or SEQ ID NO.3.

8. The isolated nucleic acid molecule of any one of claims 1–5, wherein said nucleic acid molecule is operably linked to one or more expression control elements.

9. A vector comprising an isolated nucleic acid molecule of any one of claims 1–5.

10. A host cell transformed with the nucleic acid molecule of any one claims 1–5.

11. A host cell comprising a vector of claim 9.

12. A method for producing a polypeptide comprising the step of culturing a host cell transformed with a nucleic acid molecule of any one of claims 1–5 under conditions in which the encoded telomerase reverse transcriptase is expressed.

13. A method of identifying an agent which modulates the expression of a nucleic acid encoding the protein having the sequence of SEQ ID NO.2, or SEQ ID NO.4 comprising the steps of:

exposing cells which express the nucleic acid to the agent; and determining whether the agent modulates expression of said nucleic acid, thereby identifying an agent which modulates the expression of a nucleic acid encoding the protein having the sequence of SEQ ID NO.2 or SEQ ID NO.4.

14. A method of modulating the expression of a nucleic acid encoding the protein having the sequence of SEQ ID NO.2 or SEQ ID NO.4 comprising the step of:

administering an effective amount of an agent which modulates the expression of a nucleic acid encoding the protein having the sequence of SEQ ID NO.2 or SEQ ID NO.4.

15. A method for diagnosing *Candida albicans* infection in a patient comprising the steps of:

obtaining a cell sample from the patient;

determining whether the nucleic acid of SEQ ID NO.1 or SEQ ID NO.3 is present within the cell sample; and correlating the presence of the nucleic acid of SEQ ID NO.1 or SEQ ID NO.3 with the presence of *Candida albicans*.

* * * * *